(12) United States Patent
Tanzi et al.

(10) Patent No.: US 6,248,555 B1
(45) Date of Patent: *Jun. 19, 2001

(54) GENETIC ALTERATIONS RELATED TO FAMILIAL ALZHEIMER'S DISEASE

(75) Inventors: Rudolph Tanzi, Canton; Wilma Wasco, Cambridge, both of MA (US)

(73) Assignee: The General Hospital Corporation, Boston, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/706,344

(22) Filed: Aug. 30, 1996

Related U.S. Application Data
(60) Provisional application No. 60/003,054, filed on Aug. 31, 1995.

(51) Int. Cl.$^7$ ............................ C12N 15/12; C12N 15/63; C12N 15/85

(52) U.S. Cl. .................. 435/69.1; 435/325; 435/320.1; 435/252.3; 536/23.5; 536/23.1

(58) Field of Search ............................... 536/23.1, 23.5; 435/69.1, 325, 320.1, 252.3

(56) References Cited

U.S. PATENT DOCUMENTS

| | | | |
|---|---|---|---|
| Re. 32,011 | 10/1985 | Zimmerman et al. | 260/112 B |
| 4,411,993 | 10/1983 | Gillis | 435/68 |
| 4,543,439 | 9/1985 | Frackleton, Jr. et al. | 935/92 |
| 4,579,821 | 4/1986 | Palmiter et al. | 435/172.3 |
| 4,683,195 | 7/1987 | Mullis et al. | 435/6 |
| 4,683,202 | 7/1987 | Mullis | 435/91 |
| 4,736,866 | 4/1988 | Leder et al. | 800/1 |
| 4,786,600 | 11/1988 | Kramer et al. | 435/235 |
| 4,800,159 | 1/1989 | Mullis et al. | 435/172.3 |
| 4,876,187 | 10/1989 | Duck et al. | 435/6 |
| 5,011,769 | 4/1991 | Duck et al. | 435/6 |
| 5,087,571 | 2/1992 | Leder et al. | 435/240.1 |
| 5,175,383 | 12/1992 | Leder et al. | 800/2 |
| 5,175,384 | 12/1992 | Krimpenfort et al. | 800/2 |
| 5,221,778 | 6/1993 | Byrne et al. | 800/2 |
| 5,347,075 | 9/1994 | Sorge | 800/2 |
| 5,387,742 | 2/1995 | Cordell | 800/2 |

FOREIGN PATENT DOCUMENTS

| | | |
|---|---|---|
| 0 125 023 | 11/1984 | (EP). |
| 0 171 496 | 2/1986 | (EP). |
| 0 173 494 | 5/1986 | (EP). |
| 0 184 187 | 6/1986 | (EP). |
| 0 415 731 | 6/1991 | (EP). |
| WO 86/01533 | 3/1986 | (WO). |
| WO 87/02671 | 5/1987 | (WO). |
| WO 90/07936 | 7/1990 | (WO). |
| WO 91/02805 | 3/1991 | (WO). |
| WO 94/21683 | 9/1994 | (WO). |
| WO 96/34099 | 10/1996 | (WO). |

OTHER PUBLICATIONS

Lebo et al, Cold Spring Harbor Symp. Quant. Biol., 51: 169–176 (1986).*

Sambrook et al, "Molecular Cloning, A Laboratory Manual, $2^{nd}$ Edition"; Cold Spring Harbor Laboratory Press, USA (1989) pp 16.3–16.4, 17.2, 15.81–15.84.*

Kovacs et al, Nature Medicine 2(2) pp 224–229 (1996).*

Elder et al, J of Neuroscience Research 45: 308–320 (1996).*

Cook et al, PNAS 93 pp 9223–9228 (1996).*

Sahara et al, FEBS Letters 381 (1996) 7–11.*

Gomez–Isla et al, Annals of Neurology 41(6) 809–812 (1997).*

Baumann et al, Eur J. Biochemistry 52 pp 521–529 (1975).* van Bogaert, L. et al., "Sur les formes familiales précoces de la maladie d'Alzheimer," *Mschr. Psych. Neurol.* 102:249–301 (1940).

Walder, R.Y. and J.A. Walder, "Oligodeoxynucleotide–directed mutagenesis using the yeast transformation system," *Gene* 42(2):133–139 (1986).

Boteva, K., et al., "Mutation analysis of presenilin 1 gene in Alzheimer's disease," *Lancet* 347(8994):130–131 (Jan., 1996).

Clark, R.F., et al., "The structure of the presenilin 1 (S182) gene and identification of six novel mutations in early onset AD families," *Nature Gen.* 11(2):219–222 (Oct., 1995).

Sherrington, R., et al., "Cloning of a gene bearing missense mutations in early–onset familial Alzheimer's disease," *Nature* 375(6534):754–760 (Jun., 1995).

Abraham, C.R. et al., "Immunochemical Identification of the Serine Protease Inhibitor $\alpha_1$–Antichymotrypsin in the Brain Amyloid Deposits of Alzheimer's Disease," *Cell* 52(4):487–501 (1988).

Acsadi, G. et al., "Human dystrophin expression in mdx mice after intramuscular injection of DNA constructs," *Nature* 352:815–818 (1991).

Alber, T. and G. Kawasaki, "Nucleotide Sequence of the Trisoe Phosphate Isomerase Gene of *Sacharomyces cerevisiae*," *J. Mol. Appl. Genet.* 1(5):419–434 (1982).

Ammer, G., "Expression of Genes in Yeast Using the ADCI Promoter," *Meth. Enzymol.* 101:192–201 (1983).

(List continued on next page.)

Primary Examiner—Gary L. Kunz
Assistant Examiner—Robert C. Hayes
(74) Attorney, Agent, or Firm—Sterne, Kessler, Goldstein & Fox P.L.L.C.

(57) ABSTRACT

Isolated nucleic acid molecules are provided encoding human PS1 gene products. Mutant PS1 polypeptides are also provided, as are vectors, host cells and recombinant methods for producing the same. The invention further relates to screening methods for identifying agonists and antagonists of the activity of the PS1 polypeptide and mutants thereof. Also provided are diagnostic methods for detecting Alzheimer's disease and therapeutic methods for treating the same.

52 Claims, 12 Drawing Sheets

Atkinson, A.E. et al., "Baculoviruses as Vectors for Foreign Gene Expression in Insect Cells," *Pestic. Sci.* 28:215–224 (1990).

OTHER PUBLICATIONS

Bauer, C.E. et al., "A genetic enrichment for mutations constructed by oligodeoxynucleotide–directed mutagenesis," *Gene* 37:73–81 (1985).

Beggs, J.D., "Transformation of yeast by a replicating hybrid plasmid," *Nature* 275:104–109 (1978).

Beidler, C.B. et al., "Cloning and High Level Expression of a Chimeric Antibody with Specificity for Human Carcinoembryonic Antigen," *J. Immunol.* 141911);4053–4060 (1988).

Bej, A.K. et al., "Polymerase Chain Reaction–Gene Probe Detection of Microorganisms by Using Filter–Concentrated Samples," *Appl. Environ. Microbiol.* 57(12):3529–3534 (1991).

Benjamin, R. et al., "Protective effect of apoE ε2 in Alzheimer's disease," *Lancet* 344:473 (Aug. 1994).

Bergman, Y. et al., "Two regulatory elements for immunoglobulin κ light chain gene expression," *Proc. Natl. Acad. Sci.* 81(22):7041–7045 (1984).

Better, M. et al., "*Escherichia coli* Secretion of an Active Chimeric Antibody Fragment," *Science* 240:1041–1043 (1988).

Bird, R.E. et al., "Single–Chain Antigen–Binding Proteins," *Science* 242: 423–426 (1988).

Bird, T.D. et al., "Familial Alzheimer's Disease in American Descendants of the Volga Germans: Probable Genetic Founder Effect," *Ann. Neurol.* 23(1):25–31 (1988).

Bird, T.D. et al., "Phenotypic Heterogeneity in Familial Alzheimer's Disease: A Study of 24 Kindreds," *Ann. Neurol.* 25(1):12–25 (1989).

Blais, B.W., "Transcriptional Enhancement of the *Listeria monocytogenes* PCR and Simple Immunoenzymatic Assay of the Product Using Anti–RNA:DNA Antibodies," *Appl. Environ. Microbiol.* 60(1):348–352 (Jan. 1994).

Bolivar, F. et al., "Construction and Characterization of New Cloning Vehicles. II. A Multipurpose Cloning System," *Gene* 2:95–113 (1977).

Boshart, M. et al., "A Very Strong Enhancer Is Located Upstream of an Immediate Early Gene of Human Cytomegalovirus," *Cell* 41(2):521–530 (1985).

Botstein, D. et al., "Sterile Host Yeasts (SHY): A Eukaryotic System of Biological Containment for Recombinant DNA Experiments," *Gene* 8(1):17–24 (1979).

Brinster, R.L. et al., "Factors affecting the efficiency of introducing foreign DNA into mice by microinjecting eggs," *Proc. Natl. Acad. Sci. USA* 82(13):4438–4442 (1985).

Brito, G.N.O. et al., "Behavioral Characteristics of Vasopressin–Deficient Rats (Brattleboro Strain)," *Brain Res. Bull.* 6(1):71–75 (1981).

Broach, J.R. et al., "Transformation in Yeast: Development of a Hybrid Cloning Vector and Isolation of the CAN1 gene," *Gene* 8(1):121–133 (1979).

Brousseau, T. et al., "Confirmation of the ε4 allele of the apolipoprotein E gene as a risk factor for late onset Alzheimer's disease," *Neurol.*44(2):342–344 (Feb. 1994).

Casadaban, M.J. et al., "In Vitro Gene Fusions That Join an Enzymatically Active β–Galactosidase Segment to Amino–Terminal Fragments of Exogenous Proteins: *Escherichia coli* Plasmid Vectors for the Detection and Cloning of Translational Initiation Signals," *J. Bacteriol.* 143(2):971–980 (1980).

Cataldo, A.M. et al., "Lysosomal proteinase antigens are prominently located within senile plaques of Alzheimer's disease: evidence for a neuronal origin," *Brain Res.* 513(2):181–192 (1990).

Chang, A.C.Y. et al., "Phenotypic expression in *E. coli* of a DNA sequence coding for mouse dihydrofolate reductase," *Nature* 275:617–624 (1978).

Choi–Miura, N.–H. et al., "SP–40,40 is a constituent of Alzheimer's Amyloid," *Acta Neuropathol.* 83(3):260–264 (1992).

Cook, R.H. et al., "Studies in aging of the brain: IV. Familial Alzheimer disease: Relation to transmissible dementia, aneuploidy, and microtubular defects," *Neurol.* 29(10):1402–1412 (1979).

Corder, E.H. et al., "Gene Dose of Apolipoprotein E Type 4 Allele and the Risk of Alzheimer's Disease in Late Onset Families," *Science* 261:921–923 (1993).

Corder, E.H. et al., "Protective effect of apolipoprotein E type 2 allele for late onset Alzheimer Disease," *Nature Genet.* 7(2):180–184 (Jun. 1994).

Coria, F. et al., "Isolation and Characterization of Amyloid P Component from Alzheimer's Disease and Other Types of Cerebral Amyloidosis," *Lab. Invest.* 58(4):454–458 (1988).

Corsaro, C.M. and M.L. Pearson, "Enhancing the Efficiency of DNA–Mediated Gene Transfer in Mammalian Cells," *Somatic Cell Genet.* 7(5):603–616 (1981).

Craik, C.S., "Use of Oligonucleotides for Site–Specific Mutagenesis," *BioTech.* 3(1):12–19 (1985).

Cristiano, R.J. et al., "Hepatic gene therapy: Adenovirus enhancement of receptor–mediated gene delivery and expression in primary hepatocytes," *Proc. Natl. Acad. Sci. USA* 90(6):2122–2126 (1993).

Cullen, D. et al., "Controlled Expression and Secretion of Bovine Chymosin in *Aspergillus nidulans*," *Bio/technol.* 5:369–376 (1987).

Curiel, D.T. et al., "High–Efficiency Gene Transfer Mediated by Adenovirus Coupled to DNA–Polylysine Complexes," *Hum. Gene Ther.* 3(2):147–154 (1992).

Czakó, M. and L. Màrton, "The Herpes Simplex Virus Thymidine Kinase Gene as a Conditional Negative–Selection Marker Gene in *Arabidopsis thaliana*," *Plant Physiol.* 104(3):1067–1071 (Mar. 1994).

DeNoto, F.M. et al., "Human growth hormone DNA sequence and mRNA structure: possible alternative splicing," *Nucl. Acids Res.* 9(15):3719–3730 (1981).

Drinkwater, N.R. and D.K. Klinedinst, "Chemically induced mutagenesis in a shuttle vector with a low–background mutant frequency," *Proc. Natl. Acad. Sci. USA* 83(10):3402–3406 (1986).

Duplàa, C. et al., "Quantitative Analysis of Polymerase Chain Reaction Products Using Biotinylated DuTP Incorporation," *Analyt. Biochem.* 212(1):229–236 (1993).

Elvin, C.M. et al., "Modified bacteriophage lambda promoter vectors for overproduction of proteins in *Escherichia coli*," *Gene* 87(1):123–126 (1990).

Feldman, R.G. et al., "Familial Alzheimer's Disease," *Neurol.* 13(10):811–824 (1963).

Felgner, P.L. et al., "Lipofection: A highly efficient, Lipid–mediated DNA–transfection procedure," *Proc. Natl. Acad. Sci. USA* 84(21):7413–7417 (1987).

Gershon, S. et al., "Methods for the Evaluation of Pharmacologic Agents in the Treatment of Cognitive and Other Defects in Dementia," in: *Clinical Evaluation of Psychotropic Drugs: Principles and Guidelines*, Prien, R.F. and D.S. Robinson, eds., Raven Press, Ltd., New York, NY, pp. 467–499 (Sep. 1994).

Gillies, S.D. et al., "A Tissue–specific Transcription Enhancer Element Is Located in the Major Intron of a Rearranged Immunoglobulin Heavy Chain Gene," *Cell* 33(3):717–728 (1983).

Glasky, M.S. and C.L. Reading, "Stability of Specific Immunoglobulin Secretion by EBV–Transformed Lymphoblastoid Cells and Human–Murine Heterohybridomas," *Hybridoma* 8(4):377–389 (1989).

Goate, A. et al., "Segregation of a missense mutation in the amyloid precursor protein gene with familial Alzheimer's disease," *Nature* 349:704–706 (1991).

Gold, L. et al., "Translational Initiation in Prokaryotes," *Ann. Rev. Microbiol.* 35:365–403 (1981).

Goudsmit, J. et al., "Familial Alzheimer's Disease in Two Kindreds of the Same Geographic and Ethnic Origin: A Clinical and Genetic Study," *J. Neurolog. Sci.* 49(1):79–89 (1981).

Graham, F.L. et al., "Characteristics of a Human Cell Line Transformed by DNA from Human Adenovirus Type 5," *J. Gen. Virol.* 36(1):59–72 (1977).

Graham, F.L. and A.J. Van der Eb, "A New Technique for the Assay of Infectivity of Human Adenovirus 5 DNA," *Virol.* 52(2):456–467 (1973).

Grant, F.J. et al., "Improved RNA sequencing method to determine immunoglobulin mRNA sequence," *Nucl. Acids Res.* 15(13):5496 (1987).

Hammer, R.E. et al., "Production of transgenic rabits, sheep and pigs by microinjection," *Nature* 315:680–683 (1985).

Hamos, J.E. et al., "Expression of heat shock proteins in Alzheimer's disease," *Neurol.* 41(2):345–350 (1991).

Heston, L.L. and J. White, "Pedigrees of 30 Families with Alzheimer Disease: Associations with Defective Organization of Microfilaments and Microtubules," *Behaviol Genet.* 8(4):315–331 (1978).

Hinnen, A. et al., "Transformation of yeast," *Proc. Natl. Acad. Sci. USA* 75(4):1929–1933 (1978).

Hitzeman, R.A. et al., "Isolation and Characterization of the Yeast 3–Phosphoglycerokinase Gene (PGK) by an Immunological Screening Technique," *J. Biol. Chem.* 255(24):12073–12080 (1980).

Horwitz, M.S.Z. et al., "Selection of new biological activities from random nucleotide sequences: evolutionary and practical considerations," *Genome* 31(1):112–117 (1989).

Hurby, V.J. et al., "Application of Synthetic Peptides: Antisense Peptides," in: *Synthetic Peptides: A User's Guide*, Grant, G.A., ed., W.H. Freeman, New York, NY, pp. 289–307 (1992).

Iida, K. et al., "Rapid and sensitive method for detection of Salmonella strains using a combination of polymerase chain reaction and reverse dot–blot hybridization," *FEMS Microbiol. Letts.* 114(2):167–172 (1993).

Ito, H. et al., "Transformation of Intact Yeast Cells Treated with Alkali Cations," *J. Bacteriol.* 153(1):163–168 (1983).

Jasny, B.R., "Insect Viruses Invade Biotechnology," *Science* 238:1653 (1987).

Jones, P.T. et al., "Replacing the complementarity–determining regions in a human antibody with those from a mouse," *Nature* 321:522–525 (1986).

Kamino, K. et al., "Linkage and Mutational Analysis of Familial Alzheimer Disease Kindreds for the APP Gene Region," *Am. J. Hum. Genet.* 51(5):998–1014 (1992).

Kasprzak, A.A. et al., "Location of a Contact Site between Actin and Myosin in the Three–Dimentional Structure of the Acto–S1 Complex," *Biochem.* 28:9230–9238 (1989).

Koering, C.E. et al., "Induced Expression of the Conditionally Cytotoxic Herpes Simplex Virus thymidine kinase Gene by Means of a Parvoviral Regulatory Circuit," *Hum. Gene Ther.* 5(4): 457–463 (Apr. 1994).

Kramer, F.R. and P.M. Lizardi, "Replicatable RNA reporters," *Nature* 339:401–402 (1989).

Kuusisto, J. et al., "Association of apolipoprotein E phenotypes with late onset Alzheimer's disease: population dased study," *British Med. J.* 309:636–638 (Sep. 1994).

Kyte, J. and R.F. Doolittle, "A Simple Method for Displaying the Hydropathic Character of a Protein," *J. Mol. Biol.* 157(1):105–132 (1982).

Lannfelt, L. et al., "No linkage to chromosome 14 in Swedish Alzheimer's disease families," *Nature Genet.* 4(3):218–219 (1993).

Levy–Lahad, E. et al., "Candidate Gene for the Chromosome 1 Familial Alzheimer's Disease Locus," *Science* 269:973–977 (Aug. 1995).

Liao, X. and J.A. Wise, "A simple high–efficiency method for random mutagenesis of cloned genes using forced nucleotide misincorporation," *Gene* 88(1):107–111 (1990)

Liddell, M. et al., "Confirmation of association between the e4 allele of apolipoprotein E and Alzheimer's disease," *J. Med. Genet.* 31(3):197–200 (Mar. 1994).

Liu, A.Y. et al., "Production of a Mouse–Human Chimeric Monoclonal Antibody to CD20 with Potent Fc–Dependent Biologic Activity," *J. Immunol.* 139(10):3521–3526 (1987).

Liu, A.Y. et al., "Chimeric mouse–human IgG1 antibody that can mediate lysis of cancer cells," *Proc. Natl. Acad. Sci. USA* 84(10):3439–3443 (1987).

Lizardi, P.M. et al., "Exponential Amplification of Recombinant–RNA Hybridization Probes," *Bio/Technol.* 6:1197–1202 (1988).

Loh, D.Y. et al., "Molecular Basis of a Mouse Strain–Specific Anti–Hapten Response," *Cell* 33(1):85–93 (1983).

Lomeli, H. et al., "Quantitative Assays Based on the Use of Replicatable Hybridization Probes," *Clin. Chem.* 59(9):1826–1831 (1989).

Martin, J.J. et al., "Early–onset Alzheimer's disease in 12 large Belgian families," *Neurol.* 41(1):62–68 (1991).

McGeer, P.L. et al., "Distribution of clusterin in Alzheimer brain tissue," *Brain Res.* 579(2):337–341 (1992).

McGeer, P.L. and J. Rogers, "Anti–inflammatory agents as a therapeutic approach to Alzheimer's disease," *Neurol.* 42(2):447–449 (1992).

McKnight, G.L. et al., "Identification and molecular analysis of a third *Aspergillus nidulans* alcohol dehydrogenase gene," *EMBO J.* 4(8):2093–2099 (1985).

Messing, J., "New M13 Vectors for Cloning," *Meth. Enzymol.* 101:20–78 (1983).

Miller, D.W. et al., "An Insect Baculovirus Host–Vector System for High–Level Expression of Foreign Genes," in: *Genetic Engineering Principles and Methods vol. 8*, Setlow, J.K. and A. Hollaender, eds., Plenum Press, New York, NY, 277–298 (1986).

Morrison, S.L., "Transfectomas Provide Novel Chimeric Antibodies," *Science* 229:1202–1207 (1985).

Namba, Y. et al., "Apolipoprotein E immunoreactivity in cerebral amyloid deposits and neurofibrillary tangles in Alzheimer's disease and kuru plaque amyloid in Creutzfeldt–Jakob disease," *Brain Res.* 541(1):163–166 (1991).

Nee, L.E. et al., "Dememtia of the Alzheimer type: Clinical and family study of 22 twin pairs," *Neurol.* 37:359–363 (1987).

Nee, L.E. et al., "A Family With Histologically Confirmed Alzheimer's Disease," *Arch. Neurol.* 40(4):203–208 (1983).

Neumann, E. et al., "Gene transfer into mouse lyoma cells by electroporation in high electric fields," *EMBO J.* 1(7):841–845 (1982).

Nichols, B.P. and C. Yanofsky, "Plasmids Containing the trp Promoters of *Escherichia coli* and *Serratia marcescens* and Their Use in Expressing Cloned Genes," *Meth. Enzymol.* 101:155–164 (1983).

Nickerson, D.A. et al., "Automated DNA diagnostics using an ELISA–based oligonucleotide ligation assay," *Proc. Natl. Acad. Sci. USA* 87(22):8923–8927 (1990).

Nishimura, Y. et al., "Recombinant Human–Mouse Chimeric Monoclonal Antibody Specific for Common Acute Lymphocytic Leukemia Antigen," *Cancer Res.* 47:999–1005 (1987).

Ohno, T. et al., "Gene Therapy for Vascular Smooth Muscle Cell Proliferation After Arterial Injury," *Science* 265:781–784 (Aug. 1994).

Oi, V.T. and S.L. Morrison, "Chimeric Antibodies," *BioTechniques* 4(3):214–221 (1986).

Ørskov, C. and J.H. Nielsen, "Truncated glucagon–like peptide–1 (proglucagon 78–107 amide), an intestinal insulin–releasing peptide, has specific receptors on rat insulinoma cells (RIN 5AH)," *FEBS Letts.* 229(1):175–178 (1988).

Palmiter, R.D. et al., "Metallothionein–Human GH Fusion Genes Stimulate Growth of Mice," *Science* 222:809–814 (1983).

Palmiter, R.D. and R.L. Brinster, "Transgenic Mice," *Cell* 41(2):343–345 (1985).

Paszkowski, J. et al., "Direct Gene Transfer to Plants," *EMBO J.* 3:2717–2722 (1984).

Pericak–Vance, M.A. et al., "Genetic Linkage Studies in Alzheimer's Disease Families," *Exper. Neurol.* 102(3):271–279 (1988).

Pickering, J.G. et al., "Liposome–Mediated Gene Transfer into Human Vascular Smooth Muscle Cells," *Circulation* 89(1):13–21 (Jan. 1994).

Queen, C., "A Vector That Uses Phage Signals for Efficient Synthesis of Proteins in *Escherichia coli*," *J. Mol. Appl. Genet.* 2(1):1–10 (1983).

Rapoport, S.I. et al., "Discordance and concordance of dementia of the Alzheimer type (DAT) in monozygotic twins indicate heritable and sporadic forms of Alzheimer's disease," *Neurol.* 41(10):1549–1553 (1991).

Rubin, G.M., "*Drosophila melanogaster* as an Experimental Organism," *Science* 240:1453–1459 (1988).

Russell, D.R. and G.N. Bennett, "Construction and analysis of in vivo activity of *E. coli* promoter hybrids and promoter mutants that alter the −35 to −10 spacing," *Gene* 20(2):231–243 (1982).

Russell, P.R., "Evolutionary divergence of the mRNA transcription initiation mechanism in yeast," *Nature* 301:167–169 (1983).

Schellenberg, G.D. et al., "Absence of Linkage of Chromosome 21q21 Markers to Familial Alzheimer's Disease," *Science* 241:1507–1510 (1988).

Schellenberg, G.D. et al., "Linkage Analysis of Familial Alzheimer Disease, Using Chromosome 21 Markers," *Am. J. Hum. Genet.* 48:563–583 (1991).

Schellenberg, G.D. et al., "$APP_{717}$, $APP_{693}$, and PRIP Gene Mutations Are Rare in Alzheimer Disease," *Am. J. Hum. Genet.* 49:511–517 (1991).

Schellenberg, G.D. et al., "Genetic Linkage Evidence for a Familial Alzheimer's Disease Locus on Chromosome 14," *Science* 258:668–671 (1992).

Schellenberg, G.D. et al., "Genetic Association and Linkage Analysis of the Apolipoprotein CII Locus and Familial Alzheimer's Disease," *Ann. Neurol.* 31:223–227 (1992).

Schellenberg, G.D. et al., "Chromosome 14 and Late–Onset Familial Alzheimer Disease (FAD)," *Am. J. Hum. Genet.* 53:619–628 (1993).

Shaw, D.R. et al., "Mouse/Human Chimeric Antibodies to a Tumor–Associated Antigen: Biologic Activity of the Four Human IgG Subclasses," *J. Natl. Cancer Inst.* 80(19):1553–1559 (1988).

Smith, A.D. et al., "Protective effect of apoE $\epsilon 2$ in Alzheimer's disease," *Lancet* 344:473–474 (Aug. 1994).

Stewart, C.A. and R.G.M. Morris, "The watermaze," in: *Behavioral Neuroscience, A Practical Approach*, vol. I, Sahgal, A., ed. IRL Press, Oxford, pp. 107–122 (1993).

Strauss, S. et al., "Detection of Interleukin–6 and $\alpha_2$–Macroglobulin Immunoreactivity in Cortex and Hippocampus of Alzheimer's Disease Patients," *Lab. Invest.* 66(2):223–230 (1992).

Struhl, K. et al., "High–frequency transformation of yeast: Autonomous replication of hybrid DNA molecules," *Proc. Natl. Acad. Sci. USA* 76(3):1035–1039 (1979).

Studier, F.W. et al., "Use of T7 RNA Polymerase to Direct Expression of Cloned Genes," *Meth. Enzymol.* 185:60–89 (1990).

Subramani, S. et al., "Expression of the Mouse Dihydrofolate Reductase Complementary Deoxyribonucleic Acid in Simian Virus 40 Vectors," *Mol. Cell. Biol.* 1(9):854–864 (1981).

Sun, L.K. et al., "Chimeric antibody with human constant regions and mouse variable regions directed against carcinoma–associated antigen 17–1A," *Proc. Natl. Acad. Sci. USA* 84(1):214–218, (1987).

Tsai, M.–S. et al., "Apolipoprotein E: Risk Factor for Alzheimer Disease," *Am. J. Hum. Genet.* 54:643–649 (Apr. 1994).

Turnbull, I.F. et al., "Expression of the *Escherichia coli* Entertoxin Subunit B Gene in *Aspergillus nidulans* Directed by the AMDS Promoter," *Bio/Technol.* 7:169–174 (1989).

Uéda, K. et al., "Molecular cloning of cDNA encoding an unrecognized component of amyloid in Alzheimer disease," *Proc. Natl. Acad. Sci. USA* 90(23):11282–11286 (1993).

van Duijn, C.M. et al., "A Population–based Study of Familial Alzheimer Disease: Linkage to Chromosomes 14, 19, and 21," *Am. J. Hum. Genet.* 55:714–727 (Oct. 1994).

Verhoeyen, M. et al., "Reshaping Human Antibodies: Grafting an Antilysozyme Activity," *Science* 239:1534–1536 (1988).

Vieira, J. and J. Messing, "The pUC plasmids, an M13mp7–derived system for insertion mutagenesis and sequencing with synthetic universal primers," *Gene* 19:259–268 (1982).

Vile, R.G. and I.R. Hart, "Use of Tissue–specific Expression of the Herpes Simplex Virus Thymiding Kinase Gene to Inhibit Growth of Established Murine Melanomas following Direct Intratumoral Injection of DNA," *Cancer Res.* 53(17):3860–3864 (1993).

Wang, C.-Y. and L. Huang, "pH–sensitive immunoliposomes mediate target–cell–specific delivery and controlled expression of a foreign gene in mouse," *Proc. Natl. Acad. Sci. USA* 84(22):7851–7855 (1987).

Wheelan, L., "Familiar Alzheimer's Disease," *Ann. Hum. Genet* 23(3):300–310 (1959).

Wigler, M. et al., "Biochemical Transfer of Single–Copy Eucaryotic Genes Using Total Cellular DNA as Donor," *Cell* 14(3):725–731 (1978).

Williams, R.S. et al. "Introduction of foreign genes into tissues of living mice by DNA–coated microprojectiles," *Proc. Natl. Acad. Sci. USA* 88(7):2726–2730 (1991).

Wisniewski, T. and B. Frangione, "Apolipoprotein E: a pathological chaperone protein in patients with cerebral and systemic amyloid," *Neurosci. Letts.* 135:235–238 (1992).

Wood, C.R. et al., "The synthesis and in vivo assembly of functional antibodies in yeast," *Nature* 314:446–449 (1985).

Wu, C.H. et al., "Targeting Genes: Delivery and Persistant Expression of a Foreign Gene Driven by Mammalian Regulatory Elements in vivo," *J. Biol. Chem* 264(29):16985–16987 (1989).

Yelton, M.M. et al., "Transformation of *Alpergillus nidulans* by using a trpC plasmid," *Proc. Natl. Acad. Sci. USA* 81(5):1470–1474 (1984).

Yu, C.-E. et al., "The Apolipoprotein E/CI/CII Gene Cluster and Late–Onset Alzheimer Disease," *Am. J. Hum. Genet.* 54:631–642 (Apr. 1994).

* cited by examiner

```
           ctaccattaagtcagtcagcttttatacccggaaggatgggcagctaatctatacccat
541        ---------+---------+---------+---------+---------+---------+   600
           gatggtaattcagtcagtcgaaaatatgggccttcctacccgtcgattagatatggggta
            T  I  K  S  V  S  F  Y  T  R  K  D  G  Q  L  I  Y  T  P  F  - tcacagaagataccgagactgtgggccagagagccctgcactcaattctgaatgctgcca
601        ---------+---------+---------+---------+---------+---------+   660
           agtgtcttctatggctctgacacccggtctctcgggacgtgagttaagacttacgacggt
            T  E  D  T  E  T  V  G  Q  R  A  L  H  S  I  L  N  A  A  I  - tcatgatcagtgtcattgttgtcatgactatcctcctggtggttctgtataaatacaggt
661        ---------+---------+---------+---------+---------+---------+   720
           agtactagtcacagtaacaacagtactgataggaggaccaccaagacatatttatgtcca
            M  I  S  V  I  V  V  M  T  I  L  L  V  V  L  Y  K  Y  R  C  - gctataaggtcatccatgcctggcttattatatcatctctattgttgctgttctttttt
721        ---------+---------+---------+---------+---------+---------+   780
           cgatattccagtaggtacggaccgaataatatagtagagataacaacgacaagaaaaaaa
            Y  K  V  I  H  A  W  L  I  I  S  S  L  L  L  F  F  F  S  - cattcatttacttgggggaagtgtttaaaacctataacgttgctgtggactacattactg
781        ---------+---------+---------+---------+---------+---------+   840
           gtaagtaaatgaaccccccttcacaaattttggatattgcaacgacacctgatgtaatgac
            F  I  Y  L  G  E  V  F  K  T  Y  N  V  A  V  D  Y  I  T  V  - ttgcactcctgatctggaattttggtgtggtgggaatgatttccattcactggaaaggtc
841        ---------+---------+---------+---------+---------+---------+   900
           aacgtgaggactagaccttaaaaccacaccacccttactaaaggtaagtgacctttccag
            A  L  L  I  W  N  F  G  V  V  F  M  I  S  I  H  W  K  G  P  - cacttcgactccagcaggcatatctcattatgattagtgccctcatggccctggtgttta
901        ---------+---------+---------+---------+---------+---------+   960
           gtgaagctgaggtcgtccgtatagagtaatactaatcacgggagtaccgggaccacaaat
            L  R  L  Q  Q  A  Y  L  I  M  I  S  A  L  M  A  L  V  F  I  - tcaagtacctccctgaatggactgcgtggctcatcttggctgtgatttcagtatatgatt
961        ---------+---------+---------+---------+---------+---------+   1020
           agttcatggagggacttacctgacgcaccgagtagaaccgacactaaagtcatatactaa
            K  Y  L  P  E  W  T  A  W  L  I  L  A  V  I  S  V  Y  D  L  -
                          ↓  ↓              ↓ tagtggctgttttgtgtccgaaaggtccacttcgtatgctggttgaaacagctcaggaga
1021       ---------+---------+---------+---------+---------+---------+   1080
           atcaccgacaaaacacaggctttccaggtgaagcatacgaccaactttgtcgagtcctct
            V  A  V  L  C  P  K  G  P  L  R  M  L  V  E  T  A  Q  E  R  -
                        ⎯ ⎯              ⎯
```

FIG.1B

```
        gaaatgaaacgcttttttccagctctcatttactcctcaacaatggtgtggttggtgaata
1081    ---------+---------+---------+---------+---------+---------+  1140
        ctttactttgcgaaaaaggtcgagagtaaatgaggagttgttaccacaccaaccacttat
         N  E  T  L  F  P  A  L  I  Y  S  S  T  M  V  W  L  V  N  M - tggcagaaggagacccggaagctcaaaggagagtatccaaaaattccaagtataatgcag
1141    ---------+---------+---------+---------+---------+---------+  1200
        accgtcttcctctgggccttcgagtttcctctcataggttttttaaggttcatattacgtc
         A  E  G  D  P  E  A  Q  R  R  V  S  K  N  S  K  Y  N  A  E - aaagcacagaaagggagtcacaagacactgttgcagagaatgatgatggcgggttcagtg
1201    ---------+---------+---------+---------+---------+---------+  1260
        tttcgtgtctttccctcagtgttctgtgacaacgtctcttactactaccgcccaagtcac
         S  T  E  R  E  S  Q  D  T  V  A  E  N  D  D  G  G  F  S  E - aggaatgggaagcccagagggacagtcatctagggcctcatcgctctacacctgagtcac
1261    ---------+---------+---------+---------+---------+---------+  1320
        tccttacccttcgggtctccctgtcagtagatcccggagtagcgagatgtggactcagtg
         E  W  E  A  Q  R  D  S  H  L  G  P  H  R  S  T  P  E  S  R - gagctgctgtccaggaactttccagcagtatcctcgctggtgaagacccagaggaaaggg
1321    ---------+---------+---------+---------+---------+---------+  1380
        ctcgacgacaggtccttgaaaggtcgtcataggagcgaccacttctgggtctcctttccc
         A  A  V  Q  E  L  S  S  S  I  L  A  G  E  D  P  E  E  R  G - gagtaaaacttggattgggagatttcattttctacagtgttctggttggtaaagcctcag
1381    ---------+---------+---------+---------+---------+---------+  1440
        ctcattttgaacctaaccctctaaagtaaaagatgtcacaagaccaaccatttcggagtc
         V  K  L  G  L  G  D  F  I  F  Y  S  V  L  V  G  K  A  S  A - caacagccagtggagactggaacacaaccatagcctgtttcgtagccatattaattggtt
1441    ---------+---------+---------+---------+---------+---------+  1500
        gttgtcggtcacctctgaccttgtgttggtatcggacaaagcatcggtataattaaccaa
         T  A  S  G  D  W  N  T  T  I  A  C  F  V  A  I  L  I  G  L - tgtgccttacattattactccttgccattttcaagaaagcattgccagctcttccaatct
1501    ---------+---------+---------+---------+---------+---------+  1560
        acacggaatgtaataatgaggaacggtaaaagttctttcgtaacggtcgagaaggttaga
         C  L  T  L  L  L  A  I  F  K  K  A  L  P  A  L  P  I  S  - ccatcacctttgggcttgttttctactttgccacagattatcttgtacagccttttatgg
1561    ---------+---------+---------+---------+---------+---------+  1620
        ggtagtggaaacccgaacaaaagatgaaacggtgtctaatagaacatgtcggaaaatacc
         I  T  F  G  L  V  F  Y  F  A  T  D  Y  L  V  Q  P  F  M  D -
```

FIG.1C

```
         accaattagcattccatcaattttatatctagcatatttgcggttagaatcccatggatg
1621     ---------+---------+---------+---------+---------+---------+   1680
         tggttaatcgtaaggtagttaaaatatagatcgtataaacgccaatcttagggtacctac
          Q  L  A  F  H  Q  F  Y  I  *  H  I  C  G  *  N  P  M  D  V - tttcttctttgactataaccaaatctggggaggacaaaggtgattttcctgtgtccacat
1681     ---------+---------+---------+---------+---------+---------+   1740
         aaagaagaaactgatattggtttagacccctcctgtttccactaaaaggacacaggtgta
          S  S  L  T  I  T  K  S  G  E  D  K  G  D  F  P  V  S  T  S - ctaacaaagtcaagattcccggctggacttttgcagcttccttccaagtcttcctgacca
1741     ---------+---------+---------+---------+---------+---------+   1800
         gattgtttcagttctaagggccgacctgaaaacgtcgaaggaaggttcagaaggactggt
          N  K  V  K  I  P  G  W  T  F  A  A  S  F  Q  V  F  L  T  T - ccttgcactattggactttggaaggaggtgcctatagaaaacgattttgaacatacttca
1801     ---------+---------+---------+---------+---------+---------+   1860
         ggaacgtgataacctgaaaccttcctccacggatatcttttgctaaaacttgtatgaagt
          L  H  Y  W  T  L  E  G  G  A  Y  R  K  R  F  *  T  Y  F  I - tcgcagtggactgtgtccctcggtgcagaaactaccagatttgagggacgaggtcaagga
1861     ---------+---------+---------+---------+---------+---------+   1920
         agcgtcacctgacacagggagccacgtctttgatggtctaaactccctgctccagttcct
          A  V  D  C  V  P  R  C  R  N  Y  Q  I  *  G  T  R  S  R  R - gatatgataggcccggaagttgctgtgccccatcagcagcttgacgcgtggtcacaggac
1921     ---------+---------+---------+---------+---------+---------+   1980
         ctatactatccgggccttcaacgacacggggtagtcgtcgaactgcgcaccagtgtcctg
          Y  D  R  P  G  S  C  C  A  P  S  A  A  *  R  V  V  T  G  R - gatttcactgacactgcgaactctcaggactaccggttaccaagaggttaggtgaagtgg
1981     ---------+---------+---------+---------+---------+---------+   2040
         ctaaagtgactgtgacgcttgagagtcctgatggccaatggttctccaatccacttcacc
          F  H  *  H  C  E  L  S  G  L  P  V  T  K  R  L  G  E  V  V - tttaaaccaaacggaactcttcatcttaaactacacgttgaaaatcaacccaataattct
2041     ---------+---------+---------+---------+---------+---------+   2100
         aaatttggtttgccttgagaagtagaatttgatgtgcaacttttagttgggttattaaga
          *  T  K  R  N  S  S  S  *  T  T  R  *  K  S  T  Q  *  F  C - gtattaactgaattctgaacttttcaggaggtactgtgaggaagagcaggcaccagcagc
2101     ---------+---------+---------+---------+---------+---------+   2160
         cataattgacttaagacttgaaaagtcctccatgacactccttctcgtccgtggtcgtcg
          I  N  *  I  L  N  F  S  G  G  T  V  R  K  S  R  H  Q  Q  Q -
```

FIG.1D

```
       agaatggggaatggagaggtgggcaggggttccagcttcccttttgattttttgctgcaga
2161   ---------+---------+---------+---------+---------+---------+ 2220
       tcttaccccttacctctccacccgtccccaaggtcgaagggaaactaaaaaacgacgtct
        N  G  E  W  R  G  G  Q  G  F  Q  L  P  F  D  F  L  L  Q  T  - ctcatccttttaaatgagacttgttttcccctctctttgagtcaagtcaaatatgtaga
2221   ---------+---------+---------+---------+---------+---------+ 2280
       gagtaggaaaaatttactctgaacaaaaggggagagaaactcagttcagtttatacatct
        H  P  F  *  M  R  L  V  F  P  S  L  *  V  K  S  N  M  *  I  - ttgcctttggcaattcttcttctcaagcactgacactcattaccgtctgtgattgccatt
2281   ---------+---------+---------+---------+---------+---------+ 2340
       aacggaaaccgttaagaagaagagttcgtgactgtgagtaatggcagacactaacggtaa
        A  F  G  N  S  S  S  Q  A  L  T  L  I  T  V  C  D  C  H  F  - tcttcccaaggccagtctgaacctgaggttgctttatcctaaaagttttaacctcaggtt
2341   ---------+---------+---------+---------+---------+---------+ 2400
       agaagggttccggtcagacttggactccaacgaaataggattttcaaaattggagtccaa
        F  P  R  P  V  *  T  *  G  C  F  I  L  K  V  L  T  S  G  S  - ccaaattcagtaaattttggaaacagtacagctatttctcatcaattctctatcatgttg
2401   ---------+---------+---------+---------+---------+---------+ 2460
       ggtttaagtcatttaaaacctttgtcatgtcgataaagagtagttaagagatagtacaac
        K  F  S  K  F  W  K  Q  Y  S  Y  F  S  S  I  L  Y  H  V  E  - aagtcaaatttggattttccaccaaattctgaatttgtagacatacttgtacgctcactt
2461   ---------+---------+---------+---------+---------+---------+ 2520
       ttcagtttaaacctaaaaggtggtttaagacttaaacatctgtatgaacatgcgagtgaa
        V  K  F  G  F  S  T  K  F  *  I  C  R  H  T  C  T  L  T  C  - gcccccagatgcctcctctgtcctcattcttctctcccacacaagcagtcttttttctaca
2521   ---------+---------+---------+---------+---------+---------+ 2580
       cgggggtctacggaggagacaggagtaagaagagagggtgtgttcgtcagaaaaagatgt
         P  Q  M  P  P  L  S  S  F  F  S  P  T  Q  A  V  F  F  Y  S  - gccagtaaggcagctctgtcrtggtagcagatggtcccattattctagggtcttactctt
2581   ---------+---------+---------+---------+---------+---------+ 2640
       cggtcattccgtcgagacagyaccatcgtctaccagggtaataagatcccagaatgagaa
         Q  *  G  S  S  V  ?  V  A  D  G  P  I  I  L  G  S  Y  S  L  - tgtatgatgaaaagaatgtgttatgaatcggtgctgtcagccctgctgtcagaccttctt
2641   ---------+---------+---------+---------+---------+---------+ 2700
       acatactacttttcttacacaatacttagccacgacagtcgggacgacagtctggaagaa
        Y  D  E  K  N  V  L  *  I  G  A  V  S  P  A  V  R  P  S  S  -
```

FIG.1E

```
         ccacagcaaatgagatgtatgcccaaagcggtagaattaaagaagagtaaaatggctgtt
2701     ----------+---------+---------+---------+---------+---------+ 2760
         ggtgtcgtttactctacatacgggtttcgccatcttaatttcttctcattttaccgacaa
           T  A  N  E  M  Y  A  Q  S  G  R  I  K  E  E  *  N  G  C  * - gaagc
2761     ----- 2765
         cttcg
           S -
```

FIG.1F

```
     ctaccattaagtcagtcagcttttatacccggaaggatgggcagctaatctatacccat
541  ---------+---------+---------+---------+---------+---------+  600
     gatggtaattcagtcagtcgaaaatatgggccttcctacccgtcgattagatatggggta
      T  I  K  S  V  S  F  Y  T  R  K  D  G  Q  L  I  Y  T  P  F - tcacagaagataccgagactgtgggccagagagccctgcactcaattctgaatgctgcca
601  ---------+---------+---------+---------+---------+---------+  660
     agtgtcttctatggctctgacacccggtctctcgggacgtgagttaagacttacgacggt
      T  E  D  T  E  T  V  G  Q  R  A  L  H  S  I  L  N  A  A  I - tcatgatcagtgtcattgttgtcatgactatcctcctggtggttctgtataaatacaggt
661  ---------+---------+---------+---------+---------+---------+  720
     agtactagtcacagtaacaacagtactgataggaggaccaccaagacatatttatgtcca
      M  I  S  V  I  V  V  M  T  I  L  L  V  V  L  Y  K  Y  R  C - gctataaggtcatccatgcctggcttattatatcatctctattgttgctgttcttttttt
721  ---------+---------+---------+---------+---------+---------+  780
     cgatattccagtaggtacggaccgaataatatagtagagataacaacgacaagaaaaaaa
      Y  K  V  I  H  A  W  L  I  I  S  S  L  L  L  L  F  F  F  S - cattcatttacttgggggaagtgtttaaaacctataacgttgctgtggactacattactg
781  ---------+---------+---------+---------+---------+---------+  840
     gtaagtaaatgaaccccccttcacaaattttggatattgcaacgacacctgatgtaatgac
      F  I  Y  L  G  E  V  F  K  T  Y  N  V  A  V  D  Y  I  T  V - ttgcactcctgatctggaattttggtgtggtgggaatgatttccattcactggaaaggtc
841  ---------+---------+---------+---------+---------+---------+  900
     aacgtgaggactagaccttaaaaccacaccacccttactaaaggtaagtgaccttttccag
      A  L  L  I  W  N  F  G  V  V  F  M  I  S  I  H  W  K  G  P - cacttcgactccagcaggcatatctcattatgattagtgccctcatggccctggtgttta
901  ---------+---------+---------+---------+---------+---------+  960
     gtgaagctgaggtcgtccgtatagagtaatactaatcacgggagtaccgggaccacaaat
      L  R  L  Q  Q  A  Y  L  I  M  I  S  A  L  M  A  L  V  F  I - tcaagtacctccctgaatggactgcgtggctcatcttggctgtgatttcagtatatgatt
961  ---------+---------+---------+---------+---------+---------+  1020
     agttcatggagggacttacctgacgcaccgagtagaaccgacactaaagtcatatactaa
      K  Y  L  P  E  W  T  A  W  L  I  L  A  V  I  S  V  Y  D  L -
                   ↓     ↓         ↓
     tagtggctgttttgCgtcTgaaaggtccacttcAtatgctggttgaaacagctcaggaga
1021 ---------+---------+---------+---------+---------+---------+  1080
     atcaccgacaaaacacaggctttccaggtgaagcatacgaccaactttgtcgagtcctct
      V  A  V  L  R  L  K  G  P  L  H  M  L  V  E  T  A  Q  E  R -
```

FIG.2B

```
      gaaatgaaacgcttttttccagctctcatttactcctcaacaatggtgtggttggtgaata
1081  ---------+---------+---------+---------+---------+---------+  1140
      ctttactttgcgaaaaaggtcgagagtaaatgaggagttgttaccacaccaaccacttat
       N  E  T  L  F  P  A  L  I  Y  S  S  T  M  V  W  L  V  N  M - tggcagaaggagacccggaagctcaaaggagagtatccaaaaattccaagtataatgcag
1141  ---------+---------+---------+---------+---------+---------+  1200
      accgtcttcctctgggccttcgagtttcctctcataggttttaaggttcatattacgtc
       A  E  G  D  P  E  A  Q  R  R  V  S  K  N  S  K  Y  N  A  E - aaagcacagaaagggagtcacaagacactgttgcagagaatgatgatggcgggttcagtg
1201  ---------+---------+---------+---------+---------+---------+  1260
      tttcgtgtctttccctcagtgttctgtgacaacgtctcttactactaccgcccaagtcac
       S  T  E  R  E  S  Q  D  T  V  A  E  N  D  D  G  G  F  S  E - aggaatggggaagcccagagggacagtcatctagggcctcatcgctctacacctgagtcac
1261  ---------+---------+---------+---------+---------+---------+  1320
      tccttacccttcgggtctccctgtcagtagatcccggagtagcgagatgtggactcagtg
       E  W  E  A  Q  R  D  S  H  L  G  P  H  R  S  T  P  E  S  R - gagctgctgtccaggaactttccagcagtatcctcgctggtgaagacccagaggaaaggg
1321  ---------+---------+---------+---------+---------+---------+  1380
      ctcgacgacaggtccttgaaaggtcgtcataggagcgaccacttctgggtctcctttccc
       A  A  V  Q  E  L  S  S  S  I  L  A  G  E  D  P  E  E  R  G - gagtaaaacttggattgggagatttcattttctacagtgttctggttggtaaagcctcag
1381  ---------+---------+---------+---------+---------+---------+  1440
      ctcattttgaacctaaccctctaaagtaaaagatgtcacaagaccaaccatttcggagtc
       V  K  L  G  L  G  D  F  I  F  Y  S  V  L  V  G  K  A  S  A - caacagccagtggagactggaacacaaccatagcctgtttcgtagccatattaattggtt
1441  ---------+---------+---------+---------+---------+---------+  1500
      gttgtcggtcacctctgaccttgtgttggtatcggacaaagcatcggtataattaaccaa
       T  A  S  G  D  W  N  T  T  I  A  C  F  V  A  I  L  I  G  L - tgtgccttacattattactccttgccattttcaagaaagcattgccagctcttccaatct
1501  ---------+---------+---------+---------+---------+---------+  1560
      acacggaatgtaataatgaggaacggtaaaagttctttcgtaacggtcgagaaggttaga
       C  L  T  L  L  L  A  I  F  K  K  A  L  P  A  L  P  I  S  - ccatcacctttgggcttgttttctactttgccacagattatcttgtacagccttttatgg
1561  ---------+---------+---------+---------+---------+---------+  1620
      ggtagtggaaacccgaacaaaagatgaaacggtgtctaatagaacatgtcggaaaatacc
       I  T  F  G  L  V  F  Y  F  A  T  D  Y  L  V  Q  P  F  M  D -
```

FIG.2C

```
       accaattagcattccatcaattttatatctagcatatttgcggttagaatcccatggatg
1621   ------------------------------------------------------------  1680
       tggttaatcgtaaggtagttaaaatatagatcgtataaacgccaatcttagggtacctac
        Q  L  A  F  H  Q  F  Y  I  *  H  I  C  G  *  N  P  M  D  V -
                                 ← tttcttctttgactataaccaaatctggggaggacaaaggtgattttcctgtgtccacat
1681   ------------------------------------------------------------  1740
       aaagaagaaactgatattggtttagacccctcctgtttccactaaaaggacacaggtgta
        S  S  L  T  I  T  K  S  G  E  D  K  G  D  F  P  V  S  T  S - ctaacaaagtcaagattcccggctggacttttgcagcttccttccaagtcttcctgacca
1741   ------------------------------------------------------------  1800
       gattgtttcagttctaagggccgacctgaaaacgtcgaaggaaggttcagaaggactggt
        N  K  V  K  I  P  G  W  T  F  A  A  S  F  Q  V  F  L  T  T - ccttgcactattggactttggaaggaggtgcctatagaaaacgattttgaacatacttca
1801   ------------------------------------------------------------  1860
       ggaacgtgataacctgaaaccttcctccacggatatcttttgctaaaacttgtatgaagt
        L  H  Y  W  T  L  E  G  G  A  Y  R  K  R  F  *  T  Y  F  I - tcgcagtggactgtgtccctcggtgcagaaactaccagatttgagggacgaggtcaagga
1861   ------------------------------------------------------------  1920
       agcgtcacctgacacagggagccacgtctttgatggtctaaactccctgctccagttcct
        A  V  D  C  V  P  R  C  R  N  Y  Q  I  *  G  T  R  S  R  R - gatatgataggcccggaagttgctgtgccccatcagcagcttgacgcgtggtcacaggac
1921   ------------------------------------------------------------  1980
       ctatactatccgggccttcaacgacacggggtagtcgtcgaactgcgcaccagtgtcctg
        Y  D  R  P  G  S  C  C  A  P  S  A  A  *  R  V  V  T  G  R - gatttcactgacactgcgaactctcaggactaccggttaccaagaggttaggtgaagtgg
1981   ------------------------------------------------------------  2040
       ctaaagtgactgtgacgcttgagagtcctgatggccaatggttctccaatccacttcacc
        F  H  *  H  C  E  L  S  G  L  P  V  T  K  R  L  G  E  V  V - tttaaaccaaacggaactcttcatcttaaactacacgttgaaaatcaacccaataattct
2041   ------------------------------------------------------------  2100
       aaatttggtttgccttgagaagtagaatttgatgtgcaacttttagttgggttattaaga
        *  T  K  R  N  S  S  *  T  T  R  *  K  S  T  Q  *  F  C - gtattaactgaattctgaacttttcaggaggtactgtgaggaagagcaggcaccagcagc
2101   ------------------------------------------------------------  2160
       cataattgacttaagacttgaaaagtcctccatgacactccttctcgtccgtggtcgtcg
        I  N  *  I  L  N  F  S  G  G  T  V  R  K  S  R  H  Q  Q -
```

FIG.2D

```
       agaatggggaatggagaggtgggcaggggttccagcttcccttttgattttttgctgcaga
2161   ---------+---------+---------+---------+---------+---------+ 2220
       tcttaccccttacctctccacccgtcccaaggtcgaagggaaactaaaaaacgacgtct
        N  G  E  W  R  G  G  Q  G  F  Q  L  P  F  D  F  L  L  Q  T - ctcatccttttaaatgagacttgttttcccctctctttgagtcaagtcaaatatgtaga
2221   ---------+---------+---------+---------+---------+---------+ 2280
       gagtaggaaaaatttactctgaacaaaaggggagagaaactcagttcagtttatacatct
        H  P  F  *  M  R  L  V  F  P  S  L  *  V  K  S  N  M  *  I - ttgcctttggcaattcttcttctcaagcactgacactcattaccgtctgtgattgccatt
2281   ---------+---------+---------+---------+---------+---------+ 2340
       aacggaaaccgttaagaagaagagttcgtgactgtgagtaatggcagacactaacggtaa
        A  F  G  N  S  S  S  Q  A  L  T  L  I  T  V  C  D  C  H  F - tcttcccaaggccagtctgaacctgaggttgctttatcctaaaagttttaacctcaggtt
2341   ---------+---------+---------+---------+---------+---------+ 2400
       agaagggttccggtcagacttggactccaacgaaataggattttcaaaattggagtccaa
        F  P  R  P  V  *  T  *  G  C  F  I  L  K  V  L  T  S  G  S - ccaaattcagtaaattttggaaacagtacagctatttctcatcaattctctatcatgttg
2401   ---------+---------+---------+---------+---------+---------+ 2460
       ggtttaagtcatttaaaacctttgtcatgtcgataaagagtagttaagagatagtacaac
        K  F  S  K  F  W  K  Q  Y  S  Y  F  S  S  I  L  Y  H  V  E - aagtcaaatttggattttccaccaaattctgaatttgtagacatacttgtacgctcactt
2461   ---------+---------+---------+---------+---------+---------+ 2520
       ttcagtttaaacctaaaaggtggtttaagacttaaacatctgtatgaacatgcgagtgaa
        V  K  F  G  F  S  T  K  F  *  I  C  R  H  T  C  T  L  T  C - gcccccagatgcctcctctgtcctcattcttctctcccacacaagcagtcttttttctaca
2521   ---------+---------+---------+---------+---------+---------+ 2580
       cgggggtctacggaggagacaggagtaagaagagagggtgtgttcgtcagaaaaagatgt
        P  Q  M  P  P  L  S  S  F  F  S  P  T  Q  A  V  F  F  Y  S - gccagtaaggcagctctgtcrtggtagcagatggtcccattattctagggtcttactctt
2581   ---------+---------+---------+---------+---------+---------+ 2640
       cggtcattccgtcgagacagyaccatcgtctaccagggtaataagatcccagaatgagaa
        Q  *  G  S  S  V  ?  V  A  D  G  P  I  I  L  G  S  Y  S  L - tgtatgatgaaaagaatgtgttatgaatcggtgctgtcagccctgctgtcagaccttctt
2641   ---------+---------+---------+---------+---------+---------+ 2700
       acatactacttttcttacacaatacttagccacgacagtcgggacgacagtctggaagaa
        Y  D  E  K  N  V  L  *  I  G  A  V  S  P  A  V  R  P  S  S -
```

FIG.2E

```
     ccacagcaaatgagatgtatgcccaaagcggtagaattaaagaagagtaaaatggctgtt
2701 ----------+---------+---------+---------+---------+---------+ 2760
     ggtgtcgtttactctacatacgggtttcgccatcttaatttcttctcattttaccgacaa
       T  A  N  E  M  Y  A  Q  S  G  R  I  K  E  E  *  N  G  C  *  - gaagc
2761 ----- 2765
     cttcg
       S  -
```

FIG.2F

GENETIC ALTERATIONS RELATED TO FAMILIAL ALZHEIMER'S DISEASE

This application claims the benefit of the filing date of provisional application No. 60/003,054, filed Aug. 31, 1995.

STATEMENT OF GOVERNMENT RIGHTS IN THE INVENTION

Part of the work performed during development of this invention utilized United States Government funds. Accordingly, the U.S. Government may have certain rights in this invention.

FIELD OF THE INVENTION

The present invention relates generally to Alzheimer's disease, and more specifically to methods and compositions for use in diagnosis and treatment of Alzheimer's Disease.

BACKGROUND OF THE INVENTION

Alzheimer's disease (AD) is a devastating neurodegenerative progressive disorder, which is the predominant cause of dementia in people over 65 years of age. The prevalence of AD is estimated to be as high as 18.7% among 75–84 year-olds and 47.2% among the ≧85 year age groups, affecting a significant portion of the population in most countries of the world.

Clinical symptoms of the disease typically begin with subtle short term memory problems. As the disease progresses, difficulty with memory, language, and orientation worsen to the point of interfering with the ability of the person to function independently. Other symptoms, which are variable, include myoclonus and seizures. Duration of AD from the first symptoms of memory loss until death is 10 years on average, but may range from 6–8 years to more than 20 years. AD always results in death, often from respiratory-related illness.

The pathology in AD is confined exclusively to the central nervous system (CNS). The AD brain is characterized by the presence of amyloid deposits and neurofibrillary tangles (NFT).

Amyloid deposits are found associated with the vascular system of the CNS and as focal deposits in the parenchyma. The major molecular component of an amyloid deposit is a highly hydrophobic peptide called the A$\beta$ peptide. This peptide aggregates into filaments in an anti-$\beta$-pleated sheet structure resulting in the birefringent nature of the AD amyloid. Although A$\beta$ is the major component of AD amyloid, other proteins have also found associated with the amyloid, e.g., $\alpha$-1-anti-chymotrypsin (Abraham, et al., *Cell* 52:487–501 (1988)), cathepsin D (Cataldo et al., *Brain Res.* 513:181–192 (1990)), non-amyloid component protein (Ueda et al., *Proc. Natl. Acad. Sci. USA* 90:11282–11286 (1993)), apolipoprotein E (apoE) (Namba et al., *Brain Res.* 541:163–166 (1991); Wisniewski & Frangione, *Neurosci. Lett.* 135:235–238 (1992); Strittmatter et al., *Proc. Natl. Acad. Sci. USA* 90:1977–1981 (1993)), apolipoprotein J (Choi-Mura et al., *Acta Neuropathol.* 83:260–264 (1992); McGeer et al., *Brain Res.* 579:337–341 (1992)), heat shock protein 70 (Hamos et al., *Neurology* 41:345–350 (1991)), complement components (McGeer & Rogers, *Neurology* 43:447–449 (1992)), $\alpha_2$-macroglobin (Strauss et al., *Lab. Invest.* 66:223–230 (1992)), interleukin-6 (Strauss et al., *Lab. Invest.* 66:223–230 (1992)), proteoglycans (Snow et al., *Lab. Invest.* 58:454–458 (1987)), and serum amyloid P (Coria et al., *Lab. Invest.* 58:454–458 (1988)).

Plaques are often surrounded by astrocytes and activated microglial cells expressing immune-related proteins, such as the MHC class II glycoproteins HLA-DR, HLA-DP, and HLA-DQ, as well as MHC class I glycoproteins, interleukin-2 (IL-2) receptors, and IL-1. Also surrounding many plaques are dystrophic neurites, which are nerve endings containing abnormal filamentous structures.

The characteristic Alzheimer's NFTs consist of abnormal filaments bundled together in neuronal cell bodies. "Ghost" NFTs are also observed in AD brains, which presumably mark the location of dead neurons. Other neuropathological features include granulovacular changes, neuronal loss, gliosis and the variable presence of Lewy bodies.

The destructive process of the disease is evident on a gross level in the AD brain to the extent that in late-stage AD, ventricular enlargement and shrinkage of the brain can be observed by magnetic resonance imaging. The cells remaining at autopsy, however, are grossly different from those of a normal brain, characterized by extensive gliosis and neuronal loss. Neurons which were possibly involved in initiating events, are absent; and other cell types, such as the activated microglial cells and astrocytes, have gene expression patterns not observed in the normal brain. Thus, the amyloid plaque structures and NFTs observed at autopsy are most likely the end-products of a lengthy disease process, far removed from the initiating events of AD.

Accordingly, attempts to use biochemical methods to identify key proteins and genes in the initiating steps of the disease are hampered by the fact that it is not possible to actually observe these critical initiating events. Rather, biochemical dissection of the AD brain at autopsy is akin to molecular archeology, attempting to reconstruct the pathogenic pathway by comparing the normal brain to the end-stage disease brain.

Substantial evidence has suggested that inherited genetic defects are involved in AD. Numerous kindreds have been described in the literature as having early-onset AD (defined as onset before age 65). Bird et al., *Ann. Neurol.* 23:25–31 (1988); Bird et al., *Ann. Neurol*, 25:12–25 (1989); Cook et al., *Neurology* 29:1402–1412 (1979); Feldman et al., *Neurology* 13:811–824 (1960); Goudsmit, *J. Neurol. Sci.* 49:79 (1981); Heston & White, *Behavior Genet.* 8:315–331 (1978); Martin et al., *Neurology* 41:62–68 (1991); Nee et al., *Arch. Neurol.* 40:203–208 (1983); van Bogaeert et al., *Mschr. Psych. Neurol.* 102:249–301 (1940); Wheelan, *Ann. Hum. Genet.* 23:300–309 (1959)). Families with multiple late-onset AD cases have also been described (Bird et al., *Ann. Neurol.* (1989), supra; Heston & White, *Behavior Genet.* (1978), supra; Pericak-Vance et al., *Exp. Neurol.* 102:271–279 (1988)). In addition, twin studies have documented that monozygotic twins are more concordant in their AD phenotype than dizygotic twins (Nee et al., *Neurology* 37:359–363 (1987). Also, the families of concordant twins have more secondary cases of AD than families of discordant twins (Rapoport et al., *Neurology* 41:1549–1553 (1991)).

Genetic dissection of AD has been complicated by the complexity and overall accuracy of its diagnosis. Because AD is relatively common in the elderly, clustering of cases in a family may occur by chance, representing possible confounding non-allelic genetic heterogeneity, or etiologic heterogeneity with genetic and non-genetic cases co-existing in the same kindred. In addition, the clinical diagnosis of AD is confounded with other dementing diseases common in the elderly.

Despite these problems, mutations in the amyloid precursor protein (APP) gene on chromosome 21 have been associated with early-onset (<65 years) autosomal dominant AD (Goate et al., *Nature* 349:704 (1991)). Moreover, mutations in two recently identified genes, S182 on chromosome 14 and STM-2 on chromosome 1, which encode presenilin 1 (PS1) and presenilin 2 (PS2), respectively, have also been associated with early-onset autosomal dominant AD (Schellenberg et al., *Science* 258:668 (1992); Sherrington et al., *Nature* 375:754–760 (1995); Levy-Lahad/Wasco et al., *Science* 269:973–977 (1995)).

For late-onset AD, the APOE gene has been identified as a genetic modifying factor (Strittmatter et al., *Proc. Natl. Acad. Sci. USA* 90:1977 (1993); Corder et al., *Science* 261:921 (1993); Corder et al., *Nat. Genet.* 7:180–184 (1994); Benjamin et al., *Lancet* 344:473 (1994); Smith et al., *Lancet* 344:473–474 (1994)).

However, the known genetic loci for AD do not account for all cases of AD. For example, in late-onset AD approximately half of AD cases do not have the APOE ε4 allele found in several other families with high incidence of AD, including the Volga German (VG) kindreds. Brousseau et al., *Neurology* 342 (1994); Kuusisto et al., *Brit. Med. J.* 309:363 (1994); Tsai et al., *Am. J. Hum. Genet.* 54:643 (1994); Liddel et al., *J. Med. Genet.* 31:197 (1994); Cook et al., *Neurology* (1979), supra; Bird et al., *Ann. Neurol.* (1988), supra; Bird et al., *Ann. Neurol.* 25:12 (1989). The known AD loci have been excluded as possible causes of the discrepancy. Schellenberg et al., *Science* (1992), supra; Lannfelt et al., *Nat. Genet.* 4:218–219 (1993)); van Duijn et al., *Am. J Hum. Genet.* 55:714–727 (1994); Schellenberg et al., *Science* 241:1507 (1988); Schellenberg et al., *Am. J. Hum. Genet.* 48:563 (1991); Schellenberg et al., *Am. J. Hum. Genet.* 49:511–517 (1991); Kamino et al., *Am. J. Hum. Genet.* 51:998 (1992); Schellenberg et al., *Am J. Hum. Genet.* 53:619 (1993); Schellenberg et al., *Ann. Neurol.* 31:223 (1992); Yu et al., *Am. Hum. Genet.* 54:631 (1994)). Thus, identification of new genes and of risk-modifying alterations of existing genes will add considerably to an understanding of the genetic determinants of AD, and enable biochemical and genetic approaches to the diagnosis and therapeutic treatment.

The present invention provides novel, previously unidentified and apparently pathogenic mutations of the chromosomal loci for familial AD (FAD), methods and compositions for diagnosis and treatment of AD, and other related advantages.

SUMMARY OF THE INVENTION

Briefly stated, the present invention provides isolated nucleic acid molecules encoding a PS1 gene product. A representative nucleic acid molecule is provided in FIGS. 2A–2F, while in other embodiments, nucleic acid molecules are provided which encode a mutant PSi gene product that increases the probability of Alzheimer's disease (in a statistically significant manner). One representative illustration of such a mutant is an amino acid substitution at residue 263, wherein, for example, an arginine may be substituted for a cysteine (C263R) (SEQ ID NO:28). Another representative illustration of such a mutant is an amino acid substitution at residue 264, wherein, for example, a leucine may be substituted for a proline (P264L) (SEQ ID NO:30). A third representative illustration of such a mutant is an amino acid substitution at residue 269, wherein, for example, a histidine may be substituted for an arginine (R269H) (SEQ ID NO:32).

Other aspects of the present invention included isolated nucleic acid molecules, selected from the group consisting of: a) an isolated nucleic acid molecule as set forth in FIGS. 2A–2F, or complementary sequence thereof, b) an isolated nucleic acid molecule that specifically hybridizes to the nucleic acid molecule of (a) under conditions of high stringency, and c) an isolated nucleic acid that encodes a PS1 gene product. As utilized herein, it should be understood that a nucleic acid molecule hybridizes "specifically" to a PS1 gene (or related sequence) if it hybridizes detectably to such a sequence, but does not usually hybridize to the PS2 gene sequence under the same conditions. The invention also provides methods of obtaining said nucleic acid molecules, fragments thereof, or functional derivatives thereof.

The present invention also provides expression vectors comprising a promoter operably linked to one of the nucleic acid molecules described above. Within related aspects, viral vectors are provided that are capable of directing the expression of a nucleic acid molecule as described above. Also provided are host cells which carry the above-described vectors.

The present invention further provides isolated proteins comprising a PS1 gene product, as well as PS1 peptides of greater than 12, 13, or 20 amino acids. Within one embodiment, a protein is provided that has the amino acid sequence set forth in FIGS. 2A–2F. Within another embodiment, the protein is a mutant PS1 gene product that increases the probability of Alzheimer's disease. Such mutants include those with an amino acid substitution at residue 263 (e.g., an arginine:cysteine substitution), or at residue 264 (e.g., a leucine:proline substitution), or at residue 269 (e.g., a histidine:arginine substitution). In addition, PS1 peptides are provided which are composed of 13 to 20 amino acids derived or selected from the N-terminal, internal, or carboxyl-terminal hydrophilic regions.

Within yet another embodiment of the present invention, methods of treating or preventing Alzheimer's disease are provided, comprising the step of administering to a patient a vector containing or expressing a nucleic acid molecule, protein, or antibody specific for a PS1 protein as described above, thereby reducing the likelihood or delaying the onset of Alzheimer's disease in the patient. Within certain embodiments, the above methods may be accomplished by in vivo administration.

Also provided by the present invention are pharmaceutical compositions comprising a nucleic acid molecule, vector, host cell, protein, or antibody as described above, along with a pharmaceutically acceptable carrier or diluent.

In addition, the present invention provides antibodies which specifically bind to a PS1 protein, or to immunological equivalent, unique peptides derived from the N-terminal, internal, or carboxyl-terminal hydrophilic regions. As utilized herein, it should be understood that an antibody is specific for a PS1 protein if it binds detectably, and with a $K_A$ of $10^{-7}M$ or less, but does not bind detectably (or with an affinity of greater than $10^{-7}M$) to the PS2 protein. Also provided are hybridomas which are capable of producing such antibodies. The antibodies of the present invention include monoclonal and polyclonal antibodies, as well fragments of these antibodies, and humanized forms.

The present invention further provides nucleic acid probes which are capable of specifically hybridizing (as defined below) to a PS1 gene under conditions of high stringency. Within one related aspect, such probes comprise at least a portion of the nucleotide sequence shown in FIGS. 1A–1F or 2A–2F, or its complementary sequence, the probe being capable of specifically hybridizing to a mutant PS1 gene under conditions of high stringency. Within one particularly preferred aspect, probes are provided that are capable of specifically hybridizing to a mutant PS1 gene encoding a protein in which amino acid residue 263 is changed from cysteine to arginine, or in which amino acid 264 is changed from proline to leucine, or in which amino acid 269 is changed from arginine to histidine, each under conditions of very high stringency. Representative probes of the present invention are generally at least 12 nucleotide bases in length, although they may be longer. Also provided are primer pairs capable of specifically amplifying all, or a portion of, any of the nucleic acid molecules disclosed herein.

Moreover, in the present invention, methods and kits are provided for diagnosing a patient having an increased likelihood of contracting Alzheimer's disease comprising the steps of: a) obtaining from a patient a biological sample containing nucleic acid, b) incubating the nucleic acid with a probe which is capable of specifically hybridizing to a mutant PS1 gene under conditions and for time sufficient to allow hybridization to occur, and c) detecting the presence of hybridized probe, and thereby determining that said patient has an increased likelihood of contracting Alzheimer's disease.

Within another embodiment, methods are provided comprising the steps of: a) obtaining from a patient a biological sample containing nucleic acid, b) amplifying selected nucleic acid sequence associated with a mutant PS1 gene, and c) detecting the presence of an amplified nucleic acid sequence, and thereby determining that the patient has an increased likelihood of contracting Alzheimer's disease.

Within yet another embodiment, methods are provided comprising the steps of: a) contacting a biological sample obtained from a patient with an antibody that specifically binds to a mutant PS1 protein under conditions and for a time sufficient to allow binding of the antibody to the protein and b) detecting the presence of the bound antibody.

The invention also extends to products useful for carrying out a method of detection, such as DNA probes (labeled or unlabeled), kits and the like. And, the invention also provides a method of detecting a DNA segment within the Alzheimer's disease region of chromosome 14.

This invention further provides a diagnostic kit for the detection of the expression of PS1, or its immunological equivalents, which contains all the necessary reagents to carry out the previously described methods of detection.

In addition, the invention provides an assay and method of detection of the expression product of a gene from the Alzheimer's disease region of chromosome 14, which can be used prenatally to screen a fetus, or presymptomatically to screen a subject who is genetically predisposed to Alzheimer's disease based on his family history. Accordingly, this invention provides a diagnostic kit for the detection of the expression of PS1, or its immunological equivalents.

Within another embodiment of the present invention, peptide vaccines are provided which comprises a portion of a mutant PS1 gene product containing a mutation, in combination with a pharmaceutically acceptable carrier or diluent.

Within yet another aspect of the invention, transgenic animals are provided whose germ cells and somatic cells contain a PS1 gene which is operably linked to a promoter effective for the expression of the gene, the gene being introduced into the animal, or an ancestor of the animal, at an embryonic stage.

In addition, other embodiments provide expression of the PS1 gene from a vector as described above. While in yet another embodiment, the PS1 gene encodes a mutant gene product.

These and other aspects of the present invention will become evident upon reference to the following detailed description and attached drawings. In addition, various references are set forth herein which describe in more detail certain procedures or compositions (e.g., plasmids, etc.), and are therefore incorporated by reference their entirety.

BRIEF DESCRIPTION OF THE FIGURES

FIGS. 1A–1F depicts the nucleotide sequence of the normal S182 gene, PS1 locus (SEQ ID NO:1). Within the coding region, beneath each line of nucleotide sequence are the corresponding putative amino acid residues (SEQ ID NOs:2 and 7–26).

FIGS. 2A–2F depicts identified mutations (shown by arrows) at nucleotide sequence positions 1035, 1039 and 1054 of the S182 gene, PS1 locus (SEQ ID NO:3). Within the coding region, beneath each line of nucleotide sequence are the corresponding putative amino acid residues (SEQ ID NOs:4 and 7–26).

DEFINITIONS

Figure 1A:

In the description that follows, a number of terms used in recombinant DNA (rDNA) technology are extensively utilized. In order to provide a clear and consistent understanding of the specification and claims, including the scope to be given such terms, the following definitions are provided.

Abbreviations: AD, Alzheimer's disease; APP, amyloid precursor protein gene; APLP1 and APLP2, amyloid precursor like proteins; DNA, deoxyribonucleic acid; DS, Down syndrome; EST, expression sequence tag; FAD, familial AD; PS1, the designation given to the chromosome 14 early-onset FAD gene (S182); PS2, the designation given to the chromosome 1 early-onset FAD gene at locus 14q24.31; NFTs, neurofibrillary tangles; PCR, polymerase chain reaction; RT-PCR, PCR process in which RNA is first transcribed into DNA at the first step using reverse transcriptase (RT); RNA, ribonucleic acid; SSCP, single strand conformation polymorphism analysis; STRP, short tandem repeat polymorphism; $\Theta$, recombination fraction; YAC, yeast artificial chromosome; $Z_{max}$, maximum LOD score.

A "DNA segment," refers to a molecule comprising a linear stretch of nucleotides wherein the nucleotides are present in a sequence that encodes, through the genetic code, a molecule comprising a linear sequence of amino acid residues that is referred to as a protein, a protein fragment or a polypeptide.

A "gene" is a DNA sequence related to a single polypeptide chain or protein, and as used herein includes the 5' and 3' ends. The polypeptide can be encoded by a fill-length sequence or any portion of the coding sequence, so long as the functional activity of the protein is retained.

A "complementary DNA" or "cDNA" gene includes recombinant genes synthesized by reverse transcription of messenger RNA ("mRNA") lacking intervening sequences (introns).

A "structural gene" is a DNA sequence that is transcribed into mRNA that is then translated into a sequence of amino acids characteristic of a specific polypeptide. Typically the first nucleotide of the first translated codon is numbered +1, and the nucleotides are numbered consecutively with positive integers through the translated region of the structural gene and into the 3' untranslated region. The numbering of the nucleotides in the promoter and regulatory region 5' to the translated region proceeds consecutively with negative integers with the 5' nucleotide next to the first translated nucleotide being numbered −1.

A "restriction endonuclease" (also "restriction enzyme") is an enzyme that has the capacity to recognize a specific base sequence (usually 4, 5, or 6 base pairs in length) in a double-stranded DNA molecule, and to cleave both strands of the DNA molecule at every place where this sequence appears. For example, EcoRI recognizes the base sequence GAATTC/CTTAAG.

A "restriction fragment" comprises the DNA molecules produced by digestion with a restriction endonuclease are referred to as restriction fragments. Any given genome will be digested by a particular restriction endonuclease into a discrete set of restriction fragments.

"Agarose gel electrophoresis" is an analytical method for fractionating double-stranded DNA molecules on the basis of size is required. The most commonly used technique (though not the only one) for achieving such a fractionation is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. The DNA fragments of genomes can be visualized successfully. However, most genomes, including the human genome, contain far too many DNA sequences to produce a simple pattern of restriction fragments. For example, the human genome is digested into approximately 1,000,000 different DNA fragments by EcoRI. In order to visualize a small subset of these fragments, a methodology referred to as the Southern hybridization procedure can be applied.

"Southern blotting" or "Southern transfer" is a technique for physically transferring DNA fractionated by agarose gel electrophoresis onto a nitrocellulose filter paper or another appropriate surface or method, while retaining the relative positions of DNA fragments resulting from the fractionation procedure. The methodology used to accomplish the transfer from agarose gel to nitrocellulose involves drawing the DNA from the gel into the nitrocellulose paper by capillary action.

"Nucleic acid hybridization" depends on the principle that two single-stranded nucleic acid molecules that have complementary base sequences will reform the thermodynamically favored double-stranded structure if they are mixed in solution under the proper conditions. The double-stranded structure will be formed between two complementary single-stranded nucleic acids even if one is immobilized on a nitro-cellulose filter. In the Southern hybridization procedure, the latter situation occurs. As noted previously, the DNA of the individual to be tested is digested with a restriction endonuclease, fractionated by agarose gel electrophoresis, converted to the single-stranded form, and transferred to nitrocellulose paper, making it available for reannealing to the hybridization probe.

A "hybridization probe" (or simply a "probe") is used to visualize a particular DNA sequence in the Southern hybridization procedure, a labeled DNA molecule or hybridization probe is reacted to the fractionated DNA bound to the nitrocellulose filter. The areas on the filter that carry DNA sequences complementary to the labeled DNA probe become labeled themselves as a consequence of the reannealing reaction. The areas of the filter that exhibit such labeling are visualized. The hybridization probe is generally produced by molecular cloning of a specific DNA sequence from the human genome.

"Oligonucleotide " or "oligomer" refers to a molecule comprised of two or more deoxyribonucleotides or ribonucleotides, preferably more than three. Its exact size will depend on many factors, which in turn depend on the ultimate function or use of the oligonucleotide. An oligonucleotide may be derived synthetically or by cloning.

"Sequence amplification" (or simply "amplification") is a method for generating large amounts of a target sequence. In general, one or more amplification primers are annealed to a nucleic acid sequence. Using appropriate enzymes, sequences found adjacent to, or in between the primers is amplified.

An "amplification primer" is an oligonucleotide capable of annealing adjacent to a target sequence and serving as an initiation point for DNA synthesis when placed under conditions in which synthesis of a primer extension product which is complementary to a nucleic acid strand is initiated.

A "vector" (also a "cloning vector" or "cloning vehicle") refers to an assembly which is capable of directing the expression of the PS1 gene, as well as any additional sequence(s) or gene(s) of interest. The vector must include transcriptional promoter elements which are operably linked to the genes of interest. The vector may be composed of a plasmid, phage DNA, or other DNA sequence, an RNA sequence, or a combination of the two (e.g., a DNA-RNA chimer), which is used to "carry" inserted foreign DNA for the purpose of producing more material or protein product. The vector may replicate autonomously in a host cell, and may be characterized by one or a small number of endonuclease recognition sites at which point the DNA sequence may be cut in a determinable fashion without loss of an essential biological function of the vehicle, and into which PS1 DNA may be spliced in order to bring about its replication and cloning.

"Expression" is the process by which a structural gene produces a polypeptide. It involves transcription of the gene into mRNA, and the translation of such mRNA into polypeptide(s).

An "expression vector" is a cloning vector or vehicle designed so that a cloned gene or coding sequence inserted at a particular site will be transcribed and translated into protein. The cloned gene is placed under the control of (i.e., "operably linked to") certain control sequences, such as promoter sequence(s), a polyadenylation sequence, one or more restriction sites, as well as one or more selectable markers, such as neomycin phosphotransferase, or proteins providing tetracycline or ampicillin resistance.

Expression control sequences will vary depending on whether the vector is designed to express the operably linked gene in a prokaryotic or eukaryotic host and may additionally contain an origin of replication, additional nucleic acid restriction sites, transcriptional elements, such as enhancer elements, termination sequences, tissue-specificity elements, and/or translational initiation and termination sites, sequences conferring inducibility of transcription, and other selectable markers.

The present invention pertains both to expression of a PS1 gene, and to the expression product of the gene, as well as to functional derivatives thereof.

A "functional derivative" of the PS1 sequence is a molecule that possesses a biological activity that is substantially similar to a biological activity of a the non-recombinant PS1 protein, or nucleic acid encoding it. The protein may or may not contain post-translational modifications such as a covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties may improve the molecule's solubility, absorption, biological half life, and the like. The moieties may alternatively decrease the toxicity of the molecule, eliminate or attenuate any undesirable side effect of the molecule, and the like. Moieties capable of mediating such effects are disclosed in *Remington's Pharmaceutical Sciences* (1980). Procedures for coupling such moieties to a molecule are well known in the art.

A "fragment" of a protein or nucleic acid molecule is meant to refer to any portion of a native PS1 amino acid or nucleotide genetic sequence.

A "variant" of a PS1 protein or nucleic acid is meant to refer to a molecule substantially similar in structure and biological activity to either a native PS1 protein, or to a fragment thereof. Thus, provided that two molecules possess a common activity and may substitute for each other, they are considered variants as that term is used herein even if the composition or secondary, tertiary, or quaternary structure of one of the molecules is not identical to that found in the other, or if the amino acid or nucleotide sequence is not identical.

An "analog" of a PS1 protein or genetic sequence is meant to refer to a protein or genetic sequence which is substantially similar in function to the PS1 sequence described herein. For example, analogs of a PS1 protein described herein include isozymes and analogs of the PS1 protein or genetic sequences described herein, including alleles of the PS1 protein molecule.

An "allele" is an alternative form of a gene. In most organisms there are two alleles of any one gene (one from each parent) which occupy the same relative position on homologous chromosomes. Homozygous organisms have two identical alleles controlling a particular feature (these may be either dominant or recessive). Heterozygous organisms have two different alleles controlling a particular feature. The aspect of the feature displayed by the organism will be that determined by the dominant allele.

A "substantially pure" PS1 protein is a preparation generally lacking other cellular components, especially other non-Alzheimer's disease-linked peptides or nucleic acids.

A "genetic marker" is any segment of a chromosome that is distinguishably unique in the genome, and polymorphic in the population so as to provide information about the inheritance of linked DNA sequences, genes and/or other markers.

"Autosomal dominant" means that a trait is encoded on one of the non-sex chromosomes (autosomes) and is dominant for the phenotype it dictates for an individual having a heterozygous state.

"LOD score" is a standard measure in genetics of the likelihood of a trait being localized in the interval being scored. It is the logarithm of a calculated probability.

"Early onset Alzheimer's disease" is commonly understood to mean onset (the patient displays recognized clinical symptoms indicating AD) before age 65. By comparison "familial Alzheimer's Disease" (FAD) is a subcategory of early-onset AD, in which the genetic relationship is established because at least two of the patient's first degree relatives have presented confirmed clinical symptoms of AD at approximately the same age of early onset as the patient.

DESCRIPTION OF THE PREFERRED EMBODIMENTS

The present invention relates to novel methods and compositions for the detection and treatment of Alzheimer's disease. These methods and compositions are based upon the discovery that certain mutations of the S182 gene for AD on chromosome 14 increases the probability of Alzheimer's Disease.

I. Isolated Nucleic Acid Molecules Coding for PS1 Polypeptides

At its broadest, the invention comprises a nucleic acid sequence encompassing at least one mutation of the PS1 (S182) gene for AD on human chromosome 14. In particular, the isolated DNA segment encodes expression products useful in determining the normal role of the PS1 (S182) gene, and for developing experimental and animal models addressing the mechanisms by which alterations of PS1 influence or cause AD.

A. Isolation of Nucleic Acid

Figure 2A:

Although one embodiment of the mutant PS1 gene is disclosed in FIGS. 2A–2F, it should be understood that the present invention is not so limited. In particular, within the context of the present invention reference to the PS1 gene should be understood to include derivatives, analogs, or allelic variants of the gene disclosed in FIGS. 1A–1F that are substantially similar. As used herein, a nucleic acid molecule is deemed to be "substantially similar" if (a) the nucleotide sequence is derived from the coding region of the described gene and includes portions of the sequence or allelic variations of the sequences discussed above; (b) the nucleotide sequence is capable of hybridization to nucleotide sequences of the present invention under high or very high stringency (see Sambrook et al., *Molecular Cloning: A Laboratory Manual*, 2nd ed., Cold Spring Harbor Laboratory Press, Cold Spring Harbor, N.Y. (1989)); or (c) the DNA sequences are degenerate as a result of the genetic code to the DNA sequences defined in (a) or (b).

Further, the PS1 gene includes both complementary and non-complementary sequences, provided the sequences otherwise meet the criteria set forth herein. Within the context of the present invention, high stringency means standard hybridization conditions (e.g., 5×SSPE, 0.5% SDS at 65° C., or the equivalent), such that an appropriate nucleotide sequence is able to electively hybridize to nucleotide sequences from the AD-related gene, and to mutant nucleotide sequences. Very high stringency means the nucleotide sequence is able to selectively hybridize to a single allele of the AD-related gene.

The PS1 gene is isolated from genomic DNA or cDNA. The DNA segment may be isolated from a biological sample, preferably a biological sample containing nucleated cells. Most preferably the nucleated cells are obtained from a human. Genomic DNA libraries constructed in vectors, such as YACs (yeast artificial chromosomes), bacteriophage vectors, such as λEMBL3, λgt10, cosmids or plasmids, are suitable for screening, as are cDNA libraries constructed in bacteriophage vectors, plasmids, or the like. Such libraries may be constructed using methods and techniques known in the art (see Sambrook et al., *Molecular Cloning: A Laboratory Manual*, Cold Spring Harbor Press, Cold Spring Harbor, N.Y. (1989)) or purchased from commercial sources (e.g., Clontech).

Alternately, the PS1 gene may be isolated by PCR methods from genomic DNA, cDNA or libraries, or by probe hybridization of genomic DNA or cDNA libraries. Primers for PCR and probes for hybridization screening may be designed based on the DNA sequence of PS1 presented herein. The DNA sequence of PS1 and the corresponding predicted amino acid sequence of PS1 is presented in FIGS. 1A–1F. Primers for PCR should be derived from sequences in the 5' and 3' untranslated region in order to isolate a full-length cDNA. The primers should not have self-complementary sequences nor have complementary sequences at their 3' end (to prevent primer-dimer formation). Preferably, the GC content of the primers is about 50% and contain restriction sites. The primers are annealed to cDNA and sufficient cycles of PCR are performed to yield a product readily visualized by gel electrophoresis and staining. Mutations can be visualized by single strand conformation polymorphism (SSCP) analysis. The amplified fragment is purified and inserted into a vector, such as λgt10 or pBS(M13+), and propagated.

Suitable biological samples having nucleated cells that may be used in this invention include, but are not limited to, peripheral blood, buccal swabs, or brain tissue. The method of obtaining the biological sample will vary depending upon the nature of the sample. Such cells may either be normal or neoplastic.

B. Synthesis of Nucleic Acid

The DNA segment of the present invention may also be chemically synthesized according to the methods and techniques known to those skilled in the art. For example, a DNA fragment with the nucleotide sequence which codes for the modified expression product of the PS1 gene may be designed and, if necessary, divided into appropriate smaller fragments. Then an oligomer which corresponds to the DNA fragment, or to each of the divided fragments, may be synthesized. Such synthetic oligonucleotides may be prepared, for example, by the triester method of Matteucci et al., *J. Am. Chem. Soc.* 103:3185–3191 (1981) or by using an automated DNA synthesizer.

An oligonucleotide hybridization probe suitable for screening genomic or cDNA libraries may be designed based on the sequence provided herein. Preferably, the oligonucleotide is 20–30 bases long. Such an oligonucleotide may be synthesized by automated synthesis. The oligonucleotide may be conveniently labeled at the 5' end with a reporter molecule, such as a radionuclide, (e.g., $^{32}P$) or biotin. The library is plated as colonies or phage, depending upon the vector, and the recombinant DNA is transferred to nylon or nitrocellulose membranes. Following denaturation, neutralization, and fixation of the DNA to the membrane, the membranes are hybridized with the labeled probe. The membranes are washed and the reporter molecule detected. The hybridizing colonies or phage are isolated and propagated. Candidate clones or PCR amplified fragments may be verified as containing PS1 DNA by any of various means. For example, mutations can be visualized by single strand conformation polymorphism (SSCP) analysis. Alternately, candidate clones may be hybridized with a second, nonoverlapping probe or subjected to DNA sequence analysis. In these ways, clones containing PS1 gene, which are suitable for use in the present invention, are isolated.

II. Substantially Pure PS1 Polypeptides

In another embodiment, the present invention relates to a substantially pure polypeptide having an amino acid sequence corresponding to PS1 or a mutant thereof. In a preferred embodiment, the polypeptide has specific mutation(s) in which amino acid residue 263 is changed from cysteine to arginine, or in which amino acid 264 is changed from proline to leucine, or in which amino acid 269 is changed from arginine to histidine. The present invention also relates to fragments of the PS1 polypeptide and mutants thereof that exhibit similar activity to that exhibited by PS1 as measured in a particular biological assay.

A variety of methodologies known in the art can be utilized to obtain the peptide of the present invention. The structure of the proteins encoded by the nucleic acid molecules described herein may be predicted from the primary translation products using the hydrophobicity plot function of, for example, P/C Gene or Intelligenetics Suite (Intelligenetics, Mountain View, Calif.), or according to the methods described by Kyte and Doolittle (*J. Mol. Biol* 157:105–132 (1982)).

There are a variety of sources encoding a peptide. The peptide can be isolated as described herein from any source having the PS1 peptide. Preferably, the peptide can be isolated from a mammalian source, most preferably from a human source. In the alternative, the sequence encoding the peptide can be synthesized by methods known in the art or expressed by methods disclosed herein.

As used herein, a cell is said to be "altered to express a desired peptide" when the cell, through genetic manipulation, is made to produce a protein which it normally does not produce or which the cell normally produces at low levels. One skilled in the art can readily adapt procedures for introducing and expressing either genomic, cDNA, or synthetic sequences into either eukaryotic or prokaryotic cells in order to generate a cell which produces the peptide, in particular the PS1 peptide.

PS1 proteins of the present invention may be in the form of acidic or basic salts, or in neutral form. In addition, individual amino acid residues may be modified by oxidation or reduction. Furthermore, various substitutions, deletions, or additions may be made to the amino acid or nucleic acid sequences, the net effect of which is to retain or further enhance or decrease the biological activity of the mutant or wild-type protein. Moreover, due to degeneracy in the genetic code, there may be considerable variation in nucleotide sequences encoding the same amino acid sequence.

Guidance as to how to make phenotypically silent amino acid substitutions is provided in J. U. Bowie et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein.

Other derivatives of the PS1 proteins disclosed herein include conjugates of the proteins along with other proteins or polypeptides. This may be accomplished, for example, by the synthesis of N-terminal or C-terminal fusion proteins which may be added to facilitate purification or identification of Alzheimer Disease Proteins (see U.S. Pat. No. 4,851,341; see also, Hopp et al., *Biotechnology* 6:1204 (1988). Alternatively, fusion proteins such as PS1-β-galactosidase or PS1-luciferase may be constructed in order to assist in the identification, expression, and analysis of the PS1 proteins.

PS1 proteins of the present invention may be constructed using a wide variety of techniques, including those set forth in the Examples. Further, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site-specific (or segment specific) mutagenesis procedures may be employed to provide an altered gene having particular codons altered according to the substitution, deletion, or insertion required. Exemplary methods of making the alterations set forth above are disclosed by Walder et al. (*Gene* 42:133 (1986)); Bauer et al. (*Gene* 37:73 (1985)); Craik (*BioTechniques*, January 1985, pp. 12–19); Smith et al. (*Genetic Engineering: Principles and Methods*, Plenum Press, New York, N.Y. (1981); and Sambrook et al., *Molecular Cloning: A Laboratory Manual*, supra. Deletion or truncation derivatives of PS1 proteins (e.g., a soluble extracellular portion) may also be constructed by utilizing convenient restriction endonuclease sites adjacent to the desired deletion. Subsequent to restriction, overhangs may be filled in, and the DNA relegated. Exemplary methods of making the alterations set forth above are disclosed by Sambrook et al., *Molecular Cloning: A Laboratory Manual*, supra.

Mutations which are made in the nucleic acid molecules of the present invention preferably preserve the reading frame of the coding sequences. Furthermore, the mutations will preferably not create complementary regions that could hybridize to produce secondary mRNA structures, such as loops or hairpins, that would adversely affect translation of the mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutants screened for indicative biological activity. Alternatively, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

PS1 proteins may also be constructed utilizing techniques of PCR mutagenesis, chemical mutagenesis (Drinkwater and Klinedinst, *Proc. Natl. Acad. Sci. USA* 83:3402–3406 (1986)), by forced nucleotide misincorporation (e.g., Liao and Wise, *Gene* 88:107–111 (1990)), or by use of randomly mutagenized oligonucleotides (Horwitz et al., *Genome* 3:112–117 (1989)). Particularly preferred methods for constructing Alzheimer's disease-related proteins are set forth in more detail in the Examples.

In another aspect, the present invention provides a peptide or polypeptide comprising an epitope-bearing portion of the PS2 polypeptide or a mutant thereof. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, e.g., Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, e.g., Sutcliffe, J. G., Shinnick, T. M., Green, N. and Learner, R. A., *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, e.g., Wilson et al., *Cell* 37:767–778 (1984). The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131–5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying apeptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

III. Recombinant Expression of PS1

The present invention also provides for the manipulation and expression of the above-described genes by culturing host cells containing a vector capable of expressing the above-described genes. Such vectors or vector constructs include either synthetic or cDNA-derived nucleic acid molecules encoding PS1 proteins, which are "operably linked" to suitable transcriptional or translational regulatory elements.

The precise nature of the regulatory regions needed for gene sequence expression may vary from organism to organism, but shall, in general, include a promoter region which, in prokaryotes, contains both the promoter (which directs the initiation of RNA transcription) and the DNA sequences, which when transcribed into RNA will signal synthesis initiation. Such regions will normally include those 5'-non-coding sequences involved with initiation of transcription and translation, such as the TATA box, capping sequence, CAAT sequence, and the like.

Proper expression in a prokaryotic cell also requires the presence of a ribosome binding site upstream of the gene sequence-encoding sequence. Such ribosome binding sites are disclosed, for example, by Gold et al. (*Ann. Rev. Microbiol.* 35:365–404 (1981)).

Suitable regulatory elements may be derived from a variety of sources, including bacterial, fungal, viral, mammalian, insect, or plant genes. Selection of appropriate regulatory elements is dependent on the host cell chosen, and may be readily accomplished by one of ordinary skill in the art. Examples of regulatory elements include: a transcriptional promoter and enhancer or RNA polymerase binding sequence, a transcriptional terminator, and a ribosomal binding sequence, including a translation initiation signal.

A PS1 protein encoded by any nucleic acid molecules described above may be readily expressed by a wide variety of prokaryotic and eukaryotic host cells, including bacterial, mammalian, insect, yeast or other fungi, viral, insect, or plant cells. Methods for transforming or transfecting such cells to express foreign DNA are well known in the art.

The genetic coding sequence, e.g., PS1, and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals.

If desired, the non-coding region 3' to the sequence encoding a PS1 gene may be included for its transcriptional termination regulatory sequences, such as termination and polyadenylation. Thus, by retaining the 3'-region naturally contiguous to the DNA sequence encoding the gene, the transcriptional termination signals may be provided. Where the transcriptional termination signals are not satisfactorily functional in the expression host cell, then a 3' region functional in the host cell may be substituted.

A. Vectors

Bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., *Nature* 275:615 (1978)), the T7 RNA polymerase promoter (Studier et al., *Meth. Enzymol.* 185:60–89 (1990)), the lambda promoter (Elvin et al., *Gene* 87:123–126 (1990)), the trp promoter (Nichols & Yanofsky, *Meth. in Enzymology* 101:155 (1983)) and the tac promoter (Russell et al., *Gene* 20:231 (1982)). Representative selectable markers include various antibiotic resistance markers such as the kanamycin or ampicillin resistance genes.

Many plasmids suitable for transforming host cells are well known in the art, including among others, pBR322 (see Bolivar et al., *Gene* 2:95 (1977)), the pUC plasmids pUC18, pUC19, pUC118, pUC119 (see Messing, *Meth. in Enzymology* 101:20–77, 1983) and Vieira & Messing, *Gene* 19:259–268 (1982)), and pNH8A, pNH16a, pNH18a, and Bluescript M13 (Stratagene, La Jolla, Calif).

Suitable expression vectors for yeast and fungi include, among others, YCp50(ATCC No. 37419) for yeast, and vectors pV3 (Turnbull, *Bio/Technology* 7:169 (1989)), YRp7 (Struhl et al., *Proc. Natl. Acad. Sci. USA* 76:1035–1039 (1978)), YEp13 (Broach et al., *Gene* 8:121–133 (1979)), pJDB249 and pJDB219 (Beggs, *Nature* 275:104–108 (1978)), and derivatives thereof.

Preferred promoters for use in yeast include promoters from yeast glycolytic genes (Hitzeman et al., *J. Biol. Chem.* 255:12073–12080 (1980); Alber & Kawasaki, *J. Mol. Appl. Genet.* 1:419–434 (1982)) or alcohol dehydrogenase genes (Ammerer, *Meth. Enzymol.* 101:192–201 (1983). Examples of useful promoters for fungi vectors include those derived from *Aspergillus nidulans* glycolytic genes, such as the adh3 promoter (McKnight et al., *EMBO J.* 4:2093–2099 (1985)). The expression units may also include a transcriptional terminator. An example of a suitable terminator is the adh3 terminator (McKnight et al., *EMBO J.* 4:2093–2099 (1985)).

As with bacterial vectors, the yeast vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include leu2 (Broach et al., *Gene* 8:121–133 (1979)), ura3 (Botstein et al., *Gene* 8:17 (1979)), or his3 (Struhl et al., *Proc. Natl. Acad. Sci. USA* 76:1035–1039 (1978)). Another suitable selectable marker is the gene conferring chloramphenicol resistance on yeast cells.

Techniques for transforming fungi are well known in the literature, and have been described, for instance, by Beggs (*Nature* 275:104–108 (1978)), Hinnen et al. (*Proc. Natl. Acad. Sci. USA* 75:1929–1933 (1978)), Yelton et al. (*Proc. Natl. Acad. Sci. USA* 81:1740–1747 (1984)), and Russell (*Nature* 301:167–169, 1983)). The genotype of the host cell may contain a genetic defect that is complemented by the selectable marker present on the expression vector. Choice of a particular host and selectable marker is well within the level of ordinary skill in the art.

Viral vectors include those which comprise a promoter that directs the expression of an isolated nucleic acid molecule that encodes an Alzheimer disease protein. A wide variety of promoters may be utilized within the context of the present invention, including for example, promoters such as MoMLV LTR, RSV LTR, Friend MuLV LTR, adenoviral promoter (Ohno et al., *Science* 265:781–784 (1994)), neomycin phosphotransferase promoter/enhancer, late parvovirus promoter (Koering et al., *Hum. Gene Therap.* 5:463 (1994)), herpes tk promoter, SV40 promoter, metallothionein enhancer/promoter, cytomegalovirus immediate early promoter, and the cytomegalovirus immediate late promoter.

Within particularly preferred embodiments of the invention, the promoter is a tissue-specific promoter (see e.g., WO 91/02805; EP 0,415,731; and WO 90/07936). Representative examples of suitable tissue specific promoters include neural specific enolase promoter, platelet derived growth factor β promoter, bone morphogenetic protein promoter, human α-1-chimaerin promoter, synapsin I promoter and synapsin II promoter.

In addition, other viral-specific promoters (e.g., retroviral promoters (including those noted above, and others, such as HIV promoters), hepatitis, herpes (e.g., EBV), and bacterial, fungal or parasitic (e.g., malarial)-specific promoters may be utilized in order to target a specific cell or tissue which is infected with a virus, bacteria, fungus or parasite. Thus, PS1 proteins of the present invention may be expressed from a variety of viral vectors. Within various embodiments, either the viral vector itself, or a viral particle which contains the viral vector may be utilized in the methods and compositions described below.

Mammalian expression vectors for use in carrying out the present invention will include a promoter capable of directing the transcription of a cloned gene or cDNA. Preferred promoters include viral promoters and cellular promoters. Viral promoters include the cytomegalovirus immediate early promoter (Boshart et al., *Cell* 41:521–530 (1985)), cytomegalovirus immediate late promoter, SV40 promoter (Subramani et al., *Mol. Cell. Bio.* 1:854–864 (1981)), MMTV LTR, RSV LTR, metallothionein-1, adenovirus E1a.

Cellular promoters include the mouse metallothionein-1 promoter (Palmiter et al., U.S. Pat. No. 4,579,821), a mouse $V_K$ promoter (Bergman et al., *Proc. Natl. Acad. Sci. USA* 81:7041–7045 (1983); Grant et al., *Nucl. Acids Res.* 15:5496, 1987) and a mouse $V_H$ promoter (Loh et al., *Cell* 33:85–93 (1983)). The choice of promoter will depend, at least in part, upon the level of expression desired or the recipient cell line to be transfected.

Expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Suitable polyadenylation signals include the early or late polyadenylation signals from SV40, the polyadenylation signal from the adenovirus 5 E1B region and the human growth hormone gene terminator (DeNoto et al., *Nuc. Acids Res.* 9:3719–3730 (1981)). The expression vectors may include a noncoding viral leader sequence, such as the adenovirus-2 tripartite leader, located between the promoter and the RNA splice sites. Preferred vectors may also include enhancer sequences, such the SV40 enhancer and the mouse I enhancer (Gillies, *Cell* 33:717–728, 1983)). Suitable expression vectors can be obtained from commercial sources (e.g., Stratagene, La Jolla, Calif.).

Vectors of the present invention may contain or express a wide variety of additional nucleic acid molecules in place of or in addition to a PS1 protein as described above, either from one or several separate promoters. For example, the viral vector may express a lymphokine or lymphokine receptor, antisense or ribozyme sequence or toxins. Representative examples of lymphokines include IL-1 through IL-15, GM-CSF, G-CSF, M-CSF, α-, β-, or gamma-interferon, and tumor necrosis factors, as well as their respective receptors. Representative examples of antisense sequences include antisense sequences which block the expression of PS1 protein mutants. Representative examples of toxins include: ricin, abrin, diphtheria toxin, cholera toxin, gelonin, pokeweed antiviral protein, tritin, Shigella toxin, and Pseudomonas exotoxin A.

B. Host Cells

1. Prokaryotic Host Cells

Preferred prokaryotic host cells for use within the present invention include *E. coli*, Salmonella, Bacillus, Shigella, Pseudomonas, Streptomyces, Streptomyces, and Staphylococcus, as well as many other bacterial genera or species well known to one of ordinary skill in the art. Techniques for transforming these hosts and expressing foreign DNA sequences cloned therein are well known in the art (see, e.g., Maniatis et al., supra). Vectors used for expressing cloned DNA sequences in bacterial hosts will generally contain a selectable marker, such as a gene for antibiotic resistance, and a promoter that functions in the host cell. Appropriate promoters include the trp (Nichols & Yanofsky, *Meth. Enzymol.* 101:155–164 (1983)), lac (Casadaban et al., *J. Bacterio.* 143:971–980 (1980)), and phage λ (Queen, *J. Mol. Appl. Genet.* 2:1–10 (1983)) promoter systems.

Plasmids useful for transforming bacteria include the pUC plasmids (Messing, *Meth. Enzymol.* 101:20–78 (1983); Vieira & Messino, *Gene* 19:259–268 (1982)), pBR322 (Bolivar et al., *Gene* 2:95–113 (1977)), pCQV2 (Queen, *J. Mol. Appl. Genet.* 2:1–10 (1983)), and derivatives thereof. Plasmids may contain both viral and bacterial elements.

2. Culture Conditions

Host cells containing vector constructs of the present invention are then cultured to express a DNA molecule as described above. The cells are cultured according to standard methods in a culture medium containing nutrients required for growth of the chosen host cells. A variety of suitable media are known in the art and generally include a carbon source, a nitrogen source, essential amino acids, vitamins and minerals, as well as other components, e.g., growth factors or serum, that may be required by the particular host cells. The growth medium will generally select for cells containing the DNA construct(s) by, for example, drug selection or deficiency in an essential nutrient which is complemented by the selectable marker on the DNA construct or co-transfected with the DNA construct.

Suitable growth conditions for yeast cells, for example, include culturing in a chemically defined medium, comprising a nitrogen source, which may be a non-amino acid nitrogen source or a yeast extract, inorganic salts, vitamins and essential amino acid supplements at a temperature between 4° C. and 37° C., with 30° C. being particularly preferred.

The pH of the medium is preferably maintained at a pH greater than 2 and less than 8, more preferably pH 5–6. Methods for maintaining a stable pH include buffering and constant pH control. Preferred agents for pH control include sodium hydroxide. Preferred buffering agents include succinic acid and Bis-Tris (Sigma Chemical Co., St. Louis, Mo.).

Due to the tendency of yeast host cells to hyperglycosylate heterologous proteins, it may be preferable to express the nucleic acid molecules of the present invention in yeast cells having a defect in a gene required for asparagine-linked glycosylation. Such cells are preferably grown in a medium containing an osmotic stabilizer. A preferred osmotic stabilizer is sorbitol supplemented into the medium at a concentration between 0.1 M and 1.5 M, preferably at 0.5 M or 1.0 M.

3. Eukaryotic Host Cells

Preferred eukaryotic host cells include cultured mammalian cell lines (e.g., rodent or human cell lines) and fungal cells, including species of yeast, or filamentous fungi. In general, a host cell will be selected on the basis of its ability to produce the protein of interest at a high level or its ability to carry out at least some of the processing steps necessary for the biological activity of the protein. In this way, the number of cloned DNA sequences that must be introduced into the host cell can be minimized and overall yield of biologically active protein can be maximized.

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals.

Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides).

Yeast and fungi host cells suitable for carrying out the present invention include, among others, *Saccharomyces pombe, Saccharomyces cerevisiae*, the genera Pichia or Kluyveromyces and various species of fungi (e.g., genera Aspergillus or Neurospora).

Protocols for the transformation of yeast are well known to those ordinary skill in the art. For example, transformation may be readily accomplished either by preparation of spheroplasts of yeast with DNA (see Hinnen et al., *Proc. Natl. Acad. Sci. USA* 75:1929 (1978)) or by treatment with alkaline salts such as LiCl (see Itoh et al., *J. Bacteriology* 153:163 (1983)). Transformation of fungi may also be carried out using polyethylene glycol as described by Cullen et al. (*Bio/Technology* 5:369 (1987)).

In the alternative, nucleic acid molecules which encode the PS1 proteins of the present invention (or the vectors which contain and/or express related mutants) may readily be introduced into cells from a vertebrate or warm-blooded animal, such as a human, macaque, dog, cow, horse, pig, sheep, rat, hamster, mouse or fish cell, or any hybrid thereof.

Mammalian cells which may be useful as hosts include, among others: PCI2, NIE-115 neuroblastoma, SK-N-BE (2)C neuroblastoma, SHSY5 adrenergic neuroblastoma, NS20Y and NG108-15 murine cholinergic cell lines, or rat F2 dorsal root ganglion line, COS (e.g., deposited with the American Type Culture Collection (ATCC) No. CRL 1650 or 1651), BHK (e.g., ATCC No. CRL 6281; BHK 570 cell line (ATCC) under accession number CRL 10314), CHO (ATCC No. CCL 61), HeLa (e.g., ATCC No. CCL 2), 293 (ATCC No. 1573); Graham et al., *J. Gen. Virol.* 36:59–72 (1977)) and NS-1 cells. Other mammalian cell lines may be used within the present invention, including Rat Hep I (ATCC No. CRL 1600), Rat Hep II (ATCC No. CRL 1548), TCMK (ATCC No. CCL 139), Human lung (ATCC No. CCL 75.1), human hepatoma (ATCC No. HTB-52), Hep G2 (ATCC No. HB 8065), mouse liver (ATCC No. CCL 29.1), NCTC 1469 (ATCC No. CCL 9.1), SP2/0-Ag14 (ATCC No. 1581), HIT-TI5 (ATCC. No. CRL 1777), and RINm 5AHT$_2$B (Orskov & Nielson, *FEBS* 229(1):175–178 (1988)).

Cultured mammalian cells are generally cultured in commercially available serum-containing or serum-free media. Selection of a medium and growth conditions appropriate for the particular cell line used is well within the level of ordinary skill in the art.

Protocols for the transfection of mammalian cells are well known to those of ordinary skill in the art. Vector constructs comprising cloned DNA sequences can be introduced into cultured mammalian cells by, for example, calcium phosphate-mediated transfection (Wigler et al., *Cell* 14:725 (1978); Corsaro & Pearson, *Somatic Cell Genetics* 7:603 (1981); Graham & Van der Eb, *Virology* 52:456 (1973), electroporation (Neumann et al., *EMBO J.* 1:841–845 (1982), or DEAE-dextran mediated transfection (*Current Protocols in Molecular Biology*, Ausubel et al., eds., John Wiley and Sons, Inc., New York, N.Y. (1987)). To identify cells that have stably integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. Preferred amplifiable selectable markers are the DHFR gene and the neomycin resistance gene.

Mammalian cells containing a suitable vector are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable, selectable marker the drug concentration may be increased in a stepwise manner to select for increased copy number of the cloned sequences, thereby increasing expression levels. Cells expressing the introduced sequences are selected and screened for production of the protein of interest in the desired form or at the desired level. Cells that satisfy these criteria can then be cloned and scaled up for production.

In addition, plant cells are also available as hosts, and control sequences compatible with plant cells are available, such as the nopaline synthase promoter and polyadenylation signal sequences. See, e.g., Czako & Marton, *Plant Physiol.* 104:1067–1071 (1994); and Paszkowski et al., *Biotech.* 24:387–392 (1992). For example, the use of *Agrobacterium rhizogenes* as vectors for expressing genes in plant cells has been reviewed by Sinkar et al. (*J. Biosci.* (*Bangalore*) 11:47–58 (1987)).

Another preferred host is an insect cell, for example the Drosophila larvae. Using insect cells as hosts, the Drosophila alcohol dehydrogenase promoter can be used. Rubin, *Science* 240:1453–1459 (1988). In the alternative, baculovirus vectors can be engineered to express large amounts of PS1 in insects cells (Jasny, *Science* 238:1653 (1987); Miller et al., In: *Genetic Engineering* (1986), Setlow, J. K., et al., eds., *Plenum*, Vol. 8, pp. 277–297); Atkinson et al. (*Pestic. Sci.* 28:215–224 (1990)).

The PS1 gene may also be expressed in non-human transgenic animals such as mice, rats, rabbits, sheep, dogs and pigs (see Hammer et al., *Nature* 315:680–683 (1985); Palmiter et al., *Science* 222:809–814 (1983); Brinster et al. *Proc. Natl. Acad. Sci. USA* 82:4438–4442 (1985); Palmiter & Brinster, *Cell* 41:343–345 (1985); and U.S. Pat. Nos. 5,175,383, 5,087,571, 4,736,866, 5,387,742, 5,347,075, 5,221,778, and 5,175,384). Briefly, an expression vector, including a nucleic acid molecule to be expressed together with appropriately positioned expression control sequences, is introduced into pronuclei of fertilized eggs, for example, by microinjection. Integration of the injected DNA is detected by blot analysis of DNA from tissue samples. It is preferred that the introduced DNA be incorporated into the germ line of the animal so that it is passed on to the animal's progeny. Tissue-specific expression may be achieved through the use of a tissue-specific promoter, or through the use of an inducible promoter, such as the metallothionein gene promoter (Palmiter et al., *Science* 222:809–814 (1983)) which allows regulated expression of the transgene.

C. Protein Isolation

Proteins can be isolated by, among other methods, culturing suitable host and vector systems to produce the recombinant translation products of the present invention. Supernatants from such cell lines, or protein inclusions or whole cells where the protein is not excreted into the supernatant, can then be treated by a variety of purification procedures in order to isolate the desired proteins. For example, the supernatant may be first concentrated using commercially available protein concentration filters. Then, the concentrate may be applied to a suitable purification matrix such as, for example, an anti-protein antibody bound to a suitable support. Alternatively, anion or cation exchange resins may be employed in order to purify the protein. As a further alternative, one or more reverse-phase high performance liquid chromatography (RP-HPLC) steps may be employed to further purify the protein. Other methods of isolating the proteins of the present invention are well known in the skill of the art.

A protein is deemed to be "isolated" within the context of the present invention if no other (undesired) protein is detected pursuant to SDS-PAGE analysis followed by Coomassie blue staining. Within other embodiments, the desired protein can be isolated such that no other (undesired) protein is detected pursuant to SDS-PAGE analysis followed by silver staining.

IV. Antibodies

Antibodies to the PS1 proteins may readily be prepared given the disclosure provided herein. Within the context of the present invention, antibodies are understood to include monoclonal antibodies, polyclonal antibodies, anti-ideotropic antibodies, antibody fragments (e.g., Fab, and F(ab')$_2$, F$_V$ variable regions, or complementarity determining regions). As discussed above, antibodies are understood to be specific against an Alzheimer disease protein if it binds with a K$_a$ of greater than or equal to $10^{-7}$ M, preferably greater than or equal to $10^8$ M. The affinity of a monoclonal antibody or binding partner can be readily determined by one of ordinary skill in the art.

Briefly, polyclonal antibodies may be readily generated by one of ordinary skill in the art from a variety of warm-blooded animals such as horses, cows, various fowl, rabbits, mice, or rats. Typically, a PS1 protein or unique PS1 peptide of 13–20 amino acids (preferably conjugated to keyhole limpet hemocyanin by cross-linking with glutaraldehyde) is utilized to immunize the animal through intraperitoneal, intramuscular, intraocular, or subcutaneous injections, an adjuvant such as Freund's complete or incomplete adjuvant. Following several booster immunizations, samples of serum are collected and tested for reactivity to the PS1 protein. Particularly preferred polyclonal antisera will give a signal on one of these assays that is at least three times greater than background. Once the titer of the animal has reached a plateau in terms of its reactivity to the protein, larger quantities of antisera may be readily obtained either by weekly bleedings, or by exsanguinating the animal.

Monoclonal antibodies may also be readily generated using conventional techniques (see U.S. Pat. Nos. RE 32,011, 4,902,614, 4,543,439, and 4,411,993 which are incorporated herein by reference; see also, *Antibodies: A Laboratory Manual*, Harlow & Lane, eds., Cold Spring Harbor Press, Cold Spring Harbor, N.Y. (1988), also incorporated herein by reference).

Briefly, within one embodiment a subject animal such as a rat or mouse is injected with a PS1 protein or portion thereof as described above. The protein may be admixed with an adjuvant such as Freund's complete or incomplete adjuvant in order to increase the resultant immune response. Between one and three weeks after the initial immunization the animal may be reimmunized with another booster immunization, and tested for reactivity to the protein utilizing assays described above. Once the animal has plateaued in its reactivity to the mutant, it is sacrificed, and organs which contain large numbers of B cells such as the spleen and lymph nodes are harvested.

Cells which are obtained from the immunized animal may be immortalized by transfection with a virus such as the Epstein-Barr virus (EBV) (see, Glasky & Reading, *Hybridoma* 8(4):377–389 (1989)). Alternatively, within a preferred embodiment, the harvested spleen and/or lymph node cell suspensions are fused with a suitable myeloma cell in order to create a "hybridoma" which secretes monoclonal antibody. Suitable myeloma lines include, for example, NS-1 (ATCC. No. TLB 18), an P3X63-Ag 8.653 (ATCC No. CRL 1580).

Following the fusion, the cells may be placed into culture plates containing a suitable medium, such as RPMI 1640, or DMEM (Dulbecco's Modified Eagles Medium), as well as additional ingredients, such as fetal bovine serum. Additionally, the medium should contain a reagent which selectively allows for the growth of fused spleen and myeloma cells such as HAT (hypoxanthine, aminopterin, and thymidine) (Sigma Chemical Co., St. Louis, Mo.). After about seven days, the resulting fused cells or hybridomas may be screened in order to determine the presence of antibodies which are reactive against a PS1 protein. A wide variety of assays may be utilized to determine the presence of antibodies which are reactive against the proteins of the present invention, including for example, immunoelectrophoresis (IEP), radioimmunoassays, radioimmunoprecipitations, Enzyme-Linked Immuno-Sorbent Assays (ELISA), dot blot assays, western blots, immunoprecipitation, inhibition or competition Assays, and sandwich assays. Following several clonal dilutions and reassays, a hybridoma producing antibodies reactive against PS1 may be isolated.

Other techniques known in the art may also be utilized to construct monoclonal antibodies. In the alternative a commercial system available from Stratacyte, La Jolla, Calif., enables the production of antibodies through recombinant techniques. Briefly, mRNA may be isolated from a B cell population, and utilized to create heavy and light chain immunoglobulin cDNA expression libraries in the λ ImmunoZap(H) and λ ImmunoZap(L) vectors. These vectors may be screened individually or co-expressed to form Fab fragments or antibodies. Positive plaques may subsequently be converted to a non-lytic plasmid which allows high level expression of monoclonal antibody fragments from *E. coli*.

Similarly, portions or fragments, such as Fab or Fv fragments, of antibodies may also be constructed utilizing conventional enzymatic digestion or recombinant DNA techniques to incorporate the variable regions of a gene which encodes a specifically binding antibody. In one embodiment of the present invention, the genes which encode the variable region from a hybridoma producing a monoclonal antibody of interest are amplified using nucleotide primers for the variable region. These primers may be synthesized by one of ordinary skill in the art, or may be purchased from commercially available sources. Primers for mouse and human variable regions including, among others, primers for V$_{Ha}$, V$_{Hb}$, V$_{Hc}$, V$_{Hd}$, C$_{H1}$, V$_L$ and C$_L$ regions are available from, e.g., Stratacyte (La Jolla, Calif.). The primers may be utilized to amplify heavy or light chain variable regions, which may then be inserted into vectors such as ImmunoZAP™ H or ImmunoZAP™ L (Stratacyte), respectively. These vectors may then be introduced into *E. coli* for expression. Utilizing these techniques, large amounts of a single-chain protein containing a fusion of the V$_H$ and V$_L$ domains may be produced (see Bird et al., *Science* 242:423–426 (1988)). In addition, such techniques may be utilized to change a "murine" antibody to a "human" antibody, without altering the binding specificity of the antibody.

Once suitable antibodies have been obtained, they may be isolated or purified by many techniques well known to those of ordinary skill in the art (see *Antibodies: A Laboratory Manual*, Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques.

Antibodies of the present invention have many uses. For example, antibodies may be utilized in flow cytometry to sort cells bearing such a PS1 protein. Briefly, in order to detect the protein or peptide of interest on cells, the cells are incubated with a labeled monoclonal antibody which specifically binds to the protein of interest, followed by detection of the presence of bound antibody. These steps may also be accomplished with additional steps such as washings to remove unbound antibody. Labels suitable for use within the present invention are well known in the art including, among others, fluorescein isothiocyanate (FITC), phycoerythrin (PE), horse radish peroxidase (HRP), and colloidal gold. Particularly preferred for use in flow cytometry is FITC, which may be conjugated to purified antibody according to known methods.

Of special interest to the present invention are antibodies to PS1 which are produced in humans, or are "humanized" (i.e., non-immunogenic in a human) by recombinant or other technology. Humanized antibodies may be produced, for example by replacing an immunogenic portion of an antibody with a corresponding, but non-immunogenic portion (i.e., chimeric antibodies) (Robinson, R. R. et al., PCT/US86/02269; Akira, K. et al., EP-A 184,187; Taniguchi, M., EP-A 171,496; Morrison, S. L. et al., EP-A 173,494; Neuberger, M. S. et al., PCT Appl. WO 86/01533; Cabilly, S. et al., EP-A 125,023; Better, M. et al., *Science* 240:1041–1043 (1988); Liu, A. Y. et al., *Proc. Natl. Acad. Sci. USA* 84:3439–3443 (1987); Liu, A. Y. et al., *J. Immunol.* 139:3521–3526 (1987); Sun, L. K. et al., *Proc. Natl. Acad. Sci. USA* 84:214–218 (1987); Nishimura, Y. et al., *Canc. Res.* 47:999–1005 (1987); Wood, C. R. et al., *Nature* 314:446–449 (1985)); Shaw et al., *J. Natl. Cancer Inst.* 80:1553–1559 (1988). General reviews of "humanized" chimeric antibodies are provided by Morrison, S. L. (*Science*, 229:1202–1207 (1985)) and by Oi, V. T. et al., *BioTechniques* 4:214 (1986)). Suitable "humanized" antibodies can be alternatively produced by CDR or CEA substitution (Jones, P. T. et al., *Nature* 321:552–525 (1986); Verhoeyan et al., *Science* 239:1534 (1988); Beidler, C. B. et al., *J. Immunol.* 141:4053–4060 (1988)).

V. Methods of Detecting the Presence of PS1 in a Sample

Assays useful within the context of the present invention include those assays for detecting agonists or antagonists of PS1 protein activity. Other assays are useful for the screening of peptide or organic molecule libraries. Still other assays are useful for the identification and/or isolation of nucleic acid molecules and/or peptides within the present invention, or for diagnosis of a patient with an increased likelihood of contracting Alzheimer's disease.

A. Nucleic Acid Based Diagnostic Tests

Briefly, the present invention provides probes and primers for detecting the PS1 genes and/or mutants thereof. For example, probes are provided that are capable of specifically hybridizing to PS1 genes, DNA or RNA. For purposes of the present invention, probes are "capable of hybridizing" to PS1 genes, DNA or RNA if they hybridize to a PS1 gene under conditions of either high or moderate stringency (see Sambrook et al., *Molecular Cloning: A Laboratory Manual*, supra), but typically not to the PS2 gene. Preferably, high stringency conditions would be used, such as 5×SSPE, 1×Denhardt's solution (Sambrook et al., supra), 0.1% SDS at 65° C. and at least one wash to remove excess probe in the presence of 0.2×SSC, 1×Denhardt's solution, 0.1% SDS at 65° C. Except as otherwise provided herein, probe sequences are designed to allow hybridization to PS1 genes, but not to DNA or RNA sequences from other genes. The probes are used, for example, to hybridize to nucleic acid that is present in a biological sample isolated from a patient. The hybridized probe is then detected, thereby indicating the presence of the desired cellular nucleic acid. Preferably, cellular nucleic acid is subjected to an amplification procedure, such as PCR, prior to hybridization. Alternatively, the PS1 gene may be amplified, and the amplified product subjected to DNA sequencing.

Mutants of PS1 may be detected by DNA sequence analysis or hybridization with allele-specific oligonucleotide probes under conditions and for time sufficient to allow hybridization to the specific allele. Typically, the hybridization buffer and wash will contain tetramethyl ammonium chloride or the like (see Sambrook et al., *Molecular Cloning: A Laboratory Manual*, supra).

Probes of the present invention may be composed of DNA, RNA, nucleic acid analogues (e.g., peptide/nucleic acids), or any combination thereof. They may be as small as about 12 nucleotides in length, usually about 14 to 18 nucleotides in length, but may possibly be as large as the entire sequence of a PS1 gene. Selection of probe size is somewhat dependent upon the use of the probe, and is within the skill of the art.

Suitable probes can be constructed and labeled using techniques that are well known in the art. Shorter probes of, for example, 12 bases can be generated synthetically and labeled with $^{32}P$ using $T_4$ polynucleotide kinase. Longer probes of about 75 bases to less than 1.5 kb are preferably generated by, for example, PCR amplification in the presence of labeled precursors such as [$\alpha$-$^{32}P$]dCTP, digoxigenin-dUTP, or biotin-dATP. Probes of more than 1.5 kb are generally most easily amplified by transfecting a cell with a plasmid containing the relevant probe, growing the transfected cell into large quantities, and purifying, the relevant sequence from the transfected cells. (See Sambrook et al., supra.)

Probes can be labeled by a variety of markers, including for example, radioactive markers, fluorescent markers, enzymatic markers, and chromogenic markers. The use of $^{32}P$ is particularly preferred for marking or labeling a particular nucleic acid probe.

Illustrative examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Illustrative examples of suitable radioisotopic labels include $^{3}H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, $^{109}Pd$, etc. $^{111}In$ is a preferred isotope where in vivo imaging is used since its avoids the problem of dehalogenation of the $^{125}I$ or $^{131}I$-labeled monoclonal antibody by the liver. In addition, this radionucleotide has a more favorable gamma emission energy for imaging (Perkins et al., *Eur. J. Nucl. Med.* 10:296–301 (1985); Carasquillo et al., *J. Nucl. Med.* 28:281–287 (1987)). For example, $^{111}In$ coupled to monoclonal antibodies with 1-(P-isothiocyanato-benzyl)-DPTA has shown little uptake in non-tumorous tissues, particularly the liver, and therefore enhances specificity of tumor localization (Esteban et al., *J. Nucl. Med.* 28:861–870 (1987)).

Illustrative examples of suitable non-radioactive isotopic labels include $^{157}Gd$, $^{55}Mn$, $^{162}Dy$, $^{52}Tr$, and $^{56}Fe$.

Illustrative examples of suitable fluorescent labels include an $^{152}Eu$ label, a fluorescein label, an isothiocyanate label, a rhodamine label, a phycoerythrin label, a phycocyanin label, an allophycocyanin label, an o-phthaldehyde label, and a fluorescamine label.

Illustrative examples of suitable toxin labels include diphtheria toxin, ricin, and cholera toxin.

Illustrative examples of chemiluminescent labels include a luminal label, an isoluminal label, an aromatic acridinium ester label, an imidazole label, an acridinium salt label, an oxalate ester label, a luciferin label, a luciferase label, and an aequorin label.

Illustrative examples of nuclear magnetic resonance contrasting agents include heavy metal nuclei such as Gd, Mn, and iron.

Typical techniques for binding the above-described labels to antibodies are provided by Kennedy et al., *Clin. Chim. Acta* 70:1–31 (1976), and Schurs et al., *Clin. Chim. Acta* 81:1–40 (1977). Coupling techniques mentioned in the latter are the glutaraldehyde method, the periodate method, the dimaleimide method, the m-maleimidobenzyl-N-hydroxysuccinimide ester method, all of which methods are incorporated by reference herein.

The probes of the present invention can be utilized to detect the presence of PS1 mRNA or DNA within a sample. However, if the nucleic acid is present in only a limited amount, then it may be beneficial to amplify the relevant sequence such that it may be more readily detected or obtained.

In the alternative, mutations can be visualized by single strand conformation polymorphism (SSCP) analysis.

A variety of methods may be utilized in order to amplify a selected sequence, including, for example, RNA amplification (see Lizardi et al., *Bio/Technology* 6:1197–1202 (1988); Kramer et al., *Nature* 339:401–402 (1989); Lomeli et al., *Clinical Chem.* 35(9):1826–1831 (1989); U.S. Pat. No. 4,786,600), and DNA amplification utilizing LCR or polymerase chain reaction ("PCR") (see, U.S. Pat. Nos. 4,683,195, 4,683,202, and 4,800,159) (see also U.S. Pat. Nos. 4,876,187 and 5,011,769, which describe an alternative detection/amplification system comprising the use of scissile linkages), or other nucleic acid amplification procedures that are well within the level of ordinary skill in the art.

With respect to PCR, for example, the method may be modified as known in the art, e.g., *PCR Protocols, A Guide to Methods and Applications*, edited by Michael et al., Academic Press, 1990, utilizing the appropriate chromosomal or cDNA library to obtain the fragment of the present invention. Transcriptional enhancement of PCR may be accomplished by incorporation of bacteriophage T7 RNA polymerase promoter sequences in one of the primary oligonucleotides, and immunoenzymatic detection of the products from the enhanced emitter may be effected using anti-RNA:DNA antibodies (Blais, *Appl. Environ. Microbiol.* 60:4348–352 (1994)). PCR may also be used in combination with reverse dot-blot hybridization (Iida et al., *FEMS Microbiol. Lett.* 114:167–172 (1993)). PCR products may be quantitatively analyzed by incorporation of dUTP (Duplàa et al., *Anal. Biochem.* 212:229–236 (1993)), and samples may be filter sampled for PCR-gene probe detection (Bej et al., *Appl. Environ. Microbiol.* 57:3529–3534 (1991)).

In a particularly preferred embodiment, PCR amplification is utilized to detect PS1 gene DNA. Briefly, as described in greater detail below, a DNA sample is denatured at 95° C. in order to generate single-stranded DNA. Specific primers are then annealed to the single-stranded DNA at 37° C. to 70° C., depending on the proportion of AT/GC in the primers. The primers are extended at 72° C. with Taq DNA polymerase in order to generate the opposite strand to the template. These steps constitute one cycle, which may be repeated in order to amplify the selected sequence.

In an alternative preferred embodiment, LCR amplification is utilized for amplification. LCR primers are synthesized such that the 5' base of the upstream primer is capable of hybridizing to a unique base pair in a desired gene to specifically detect a PS1 gene. While in another preferred embodiment, the probes are used in an automated, non-isotopic strategy wherein target nucleic acid sequences are amplified by PCR, and then desired products are determined by a calorimetric oligonucleotide ligation assay (OLA) (Nickerson et al., *Proc. Natl. Acad. Sci. USA* 81:8923–8927 (1990)).

Primers for the amplification of a selected sequence should be selected from sequences that are highly specific and form stable duplexes with the target sequence. The primers should also be non-complementary, especially at the 3' end, should not form dimers with themselves or other primers, and should not form secondary structures or duplexes with other regions of DNA. In general, primers of about 18 to 20 nucleotides are preferred, and can be easily synthesized using techniques well known in the art. PCR products, and other nucleic acid amplification products, may be quantified using techniques known in the art, i.e., SSCP analysis.

B. Diagnostic Kits Comprising Nucleic Acid Probes to PS1

In another embodiment, the present invention relates to a kit for detecting the presence of PS1 in a sample comprising at least one container means having disposed therein the above-described nucleic acid probe. In a preferred embodiment, the kit further comprises other containers comprising one or more of the following: wash reagents and reagents capable of detecting the presence of bound nucleic acid probe. Examples of detection reagents include, but are not limited to radiolabelled probes, enzymatic labeled probes (horse radish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like.

Types of detection reagents include labeled secondary probes, or in the alternative, if the primary probe is labeled, the enzymatic, or antibody binding reagents which are capable of reacting with the labeled probe. One skilled in the art will readily recognize that the disclosed probes and amplification primers of the present invention can readily be incorporated into one of the established kit formats which are well known in the art.

C. Antibody-based Diagnostic Tests and Kits

The present invention further provides antibodies, as discussed above, for the detection of PS1 gene products in diagnostic tests and kits. A variety of assays can be utilized in order to detect antibodies that specifically bind to the desired protein or peptide. Exemplary assays are described in detail in *Antibodies: A Laboratory Manual*, Harlow and Lane, supra. Representative examples of such assays include IEP, radioinmunoassays, radioimmunoprecipitations, ELISA, dot blot assays, inhibition or competition assays, and sandwich assays, immunostick (dipstick) assays, simultaneous immunoassays, immunochromatographic assays, immunofiltration assays, latex bead agglutination assays, immunofluorescent assays, biosensor assays, and low-light detection assays, and the like (see, e.g., *Antibodies: A Laboratory Manual*, supra).

A fluorescent antibody test (FA-test) uses a fluorescently-labeled antibody able to bind to one of the proteins of the invention. Visual determinations using fluorescence microscopy yield a qualitative result. In a preferred embodiment, this assay is used for the examination of tissue samples and histological sections.

In latex bead agglutination assays, antibodies to one or more of the proteins of the present invention are conjugated to latex beads. The antibodies conjugated to the latex beads are then contacted with a sample under conditions permitting antibodies to bind to desired proteins in the sample, if any. Visual results yield a qualitative result. This method is preferred in the field for on-site testing.

Enzyme immunoassays (EIA) include a number of different assays able to utilize the antibodies provided by the present invention. For example, a heterogeneous indirect EIA uses a solid phase coupled with an antibody of the invention and an affiniity purified, anti-IGg imnunoglobulin preparation. Preferably, the solid phase is a polystyrene microtiter plate. The antibodies and immunoglobulin preparation are then contacted with the sample under conditions permitting antibody binding, which conditions are well known in the art. The results of such an assay can be read visually, but are preferably read using a spectrophotometer, such as an ELISA plate reader, to yield a quantitative result.

An alternative solid phase EIA format includes a plastic-coated ferrous metal beads able to be moved during the procedures of the assay by means of a magnet. Yet another alternative is a low-light detection inimunoassay format. In this highly sensitive format, the light emission produced by appropriately labeled bound antibodies are quantified automatically, preferably, using microtiter plates.

In a capture-antibody sandwich enzyme assay, the desired protein is bound between an antibody attached to a solid phase, preferably a polystyrene microtiter plate, and a labeled antibody. Preferably, the results are measured using a spectrophotometer, such as an ELISA plate reader. In an alternative embodiment, a radioactive tracer is substituted for the enzyme mediated detection in an EIA to produce a radioimmunoassay (RIA).

In a sequential assay format, reagents are allowed to incubate with the capture antibody in a step wise fashion. The test sample is first incubated with the capture antibody. Following a wash step, an incubation with the labeled antibody occurs. In a simultaneous assay, the two incubation periods described in the sequential assay are combined. This eliminates one incubation period plus a wash step.

A dipstick/immunostick format is essentially an immunoassay except that the solid phase, instead of being a polystyrene microtiter plate, is a polystyrene paddle or dipstick. Reagents are the same and the format can either be simultaneous or sequential.

In a chromatographic strip test format, a capture antibody and a labeled antibody are dried onto a chromatographic strip, which is typically nitrocellulose or nylon of high porosity bonded to cellulose acetate. The capture antibody is usually spray dried as a line at one end of the strip. At this end there is an absorbent material that is in contact with the strip. At the other end of the strip the labeled antibody is deposited in a manner that prevents it from being absorbed into the membrane. Usually, the label attached to the antibody is a latex bead or colloidal gold. The assay may be initiated by applying the sample immediately in front of the labeled antibody.

Immunofiltration/immunoconcentration formats combine a large solid phase surface with directional flow of sample/reagents, which concentrates and accelerates the binding of antigen to antibody. In a preferred format, the test sample is preincubated with a labeled antibody then applied to a solid phase such as fiber filters or nitrocellulose membranes or the like. The solid phase can also be precoated with latex or glass beads coated with capture antibody followed by detection by standard immunoassay techniques. The flow of sample/reagents can be modulated by either vacuum or the wicking action of an underlying absorbent material.

A threshold biosensor assay is a sensitive, instrumented assay amenable to screening large number of samples at low cost. In one embodiment, such an assay comprises the use of light addressable potentiometric sensors wherein the reaction involves the detection of a pH change due to binding of the desired protein by capture antibodies, bridging antibodies and urease-conjugated antibodies. Upon binding, a pH change is effected that is measurable by translation into electrical potential ($\mu$volts). The assay typically occurs in a very small reaction volume, and is very sensitive. Moreover, the reported detection limit of the assay is 1,000 molecules of urease per minute.

One type of test sample which can be utilized in the present invention is derived from amniotic fluid or cells. Such a test sample is utilized to identify fetuses which carry a human gene or mutation for FAD.

D. Diagnostic Kits Comprising Antibodies to PS1

In another embodiment of the present invention, a kit is provided which contains all the necessary reagents to carry out the previously described methods of detection. The kit may comprise: i) a first container means containing an above-described antibody, and ii) second container means containing a conjugate comprising a binding partner of the antibody and a label. In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody. One skilled in the art will readily recognize that the antibodies described in the present invention can readily be incorporated into one of the established kit formats which are well known in the art.

E. Anti-peptide Antibodies

In another embodiment, the peptide, in particular the PS1 peptide, is used to generate an antibody which is capable of binding to the peptide (e.g., anti-PS1 peptide antibodies). The anti-peptide antibodies of the present invention may include monoclonal and polyclonal antibodies, as well fragments of these antibodies, and humanized forms. Humanized forms of the antibodies of the present invention may be generated using one of the procedures known in the art such as chimerization or CDR grafting.

Moreover, the invention also provides hybridomas which are capable of producing the above-described antibodies.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", in *Synthetic Peptides, A User's Guide*, W. H. Freeman, N.Y., pp. 289–307 (1992), and Kaspczak et al., *Biochemistry* 28:9230–8 (1989).

Anti-peptide peptides can be generated in one of two fashions. First, the anti-peptide peptides can be generated by replacing the basic amino acid residues found in the peptide sequence, e.g., the IT-11 peptide sequence, with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

Alternatively, the anti-peptide peptides of the present invention can be generated by synthesizing and expressing a peptide encoded by the antisense strand of the DNA which encodes the peptides, preferably the IT-11 peptide. Peptides produced in this fashion are, in general, similar to those described above since codons complementary to those coding for basic residues generally code for acidic residues.

One skilled in the art will readily recognize that the antibodies described in the present invention can readily be incorporated into one of the established kit formats which are well known in the art.

F. Other Assays

Transmembrane receptors are involved in many cellular communication process and have been the targets of numerous pharmacologic screening assays for the identification and development of new therapeutic agents. Many of these screening assays look for ligand induced changes in cell lines expressing the recombinant receptor. In some cases second messengers are assayed directly while in others, receptor is transfected into a cell line carrying a reporter gene construct whose expression level can be influenced (positively or negatively) by functional activation of the receptor. One common result of the stimulation of many different second messenger systems is transient changes in intracellular calcium homeostasis. This can be the result of $Ca^{2+}$ release from various intracellular compartments or from the influx of extracellular calcium.

Calcium transients offer a highly sensitive and selective method for characterization of PS1 gene function. Expression of recombinant PS1 in cell lines previously transfected with an aequorin reporter construct can be used to screen for and identify a PS1 ligand. Aequorin is a 21 kDa photoprotein that upon $Ca^{2+}$ binding undergoes an irreversible reaction with the production of light in the visible range. Because the fractional rate of aequorin consumption is proportional in the physiological $[Ca^{2+}]$, it has been used for many years as a sensitive indicator of intracellular calcium. More recently, several different aequorin cDNA's have been engineered which allow selective targeting of aequorin expression to different intracellular compartments, including the cytoplasm, the nucleus and the endoplasmic reticulum. This allows for a variety of second messenger coupled pathways/compartments to be screened. Identification of the PS1 ligand and determination of its signaling pathway will be a first step in the functional characterization of the PS1 gene. A cell line expressing mutant PS1 can be set up and screened in parallel in order to identify compounds which modify the mutant protein function in a way that mimics wild-type PS1 activity.

VI. Methods of Treating or Preventing Alzheimer's Disease

The present invention also provides methods for treating, or preventing Alzheimer disease, comprising the step of administering to a patient a vector (e.g., expression vector, viral vector, or viral particle containing a vector), as described above, thereby reducing, the likelihood or delaying the onset of Alzheimer's disease.

Similarly, therapeutic peptides, peptidomimetics, or small molecules may be used to delay onset of Alzheimer's disease, lessen symptoms, or halt or delay progression of the disease. Such therapeutics may be tested in a transgenic animal model that expresses mutant protein, wild-type and mutant protein, or in an in vitro assay system.

One such in vitro assay system measures the amount of amyloid protein produced. Briefly, by way of illustration, a cell expressing both PS1 gene product and amyloid is cultured in the presence of a candidate therapeutic molecule. The PS1 protein expressed by the cell may be either wild-type or mutant protein. In either case, the amount of amyloid protein that is produced is measured from cells incubated with or without (control) the candidate therapeutic. Briefly, by way of example, cells are labeled in medium containing $^{35}S$-methionine and incubated in the presence (or absence) of candidate therapeutic. Amyloid protein is detected in the culture supernatant by immunoprecipitation and SDS-PAGE electrophoresis or by ELISA. A statistically significant reduction of amyloid protein compared to the control signifies a therapeutic suitable for use in preventing or treating Alzheimer's disease.

Alternatively, transgenic animals expressing Alzheimer's disease protein may be used to test candidate therapeutics. Amyloid protein is measured or, if the animals exhibit other disease symptoms, such as memory or learning deprivation, an increase in memory or learning is measured. Memory and learning are tested in rodents by the Morris water maze (Stewart and Morris in *Behavioral Neuroscience*, R. Saghal Ed. (IRLPress, 1993, p. 107) and the Y-maze (Brits et al., *Brain Res. Bull.* 6:71 (1981)). Therapeutics are administered to animals prior to testing. The response time in trials are measured and an improvement in memory and learning is demonstrated by a statistically significant decrease in the timed trials.

As noted above, the present invention provides methods for treating or preventing Alzheimer's disease through the administration to a patient of a therapeutically effective amount of an antagonist or pharmaceutical composition as described herein. Such patients may be identified through clinical diagnosis based on symptoms of dementia or learning and memory loss which are not attributable to other causes. In addition, patients are also identified through diagnosis of brain atrophy as determined by magnetic resonance imaging.

In another embodiment of the present invention, methods are presented for decreasing the expression of the PS1 peptide disclosed herein. Specifically, anti-sense RNA expression is used to disrupt the translation of the genetic message. In detail, a cell is modified using routine procedures such that it expresses an antisense message, a message which is complementary to the PS1 message. By constitutively or inducibly expressing the antisense RNA, the translation of PS1 mRNA can be regulated.

Cognitive behavior in AD may be measured by any one of several tests (See Gershon et al., *Clinical Evaluation of Psychotropic Drugs: Principles and Guidelines*, Prien and Robinson (eds.), Raven Press, Ltd., New York, 1994, p. 467). One such test, BCRS, is designed to measure only cognitive functions: concentration, recent memory, past memory, orientation, functioning, and self-care. This test, as well as the Weschler Memory Scale and the Alzheimer's Disease-Associated Scale, may be used to determine improvement following therapeutic treatment. "Improvement" in Alzheimer's disease is present if there is a statistically significant difference in the direction of normality in the Weschier Memory Scale test. For example, test results of the performance of treated patients as are compared to members of the placebo group or between subsequent tests given to the same patient. Improvement within the present invention also encompasses a delay in the age of onset of Alzheimer's disease.

A. Pharmaceutical Compositions

The present invention also provides a variety of pharmaceutical compositions, comprising one of the PS1 proteins, nucleic acid molecules, vectors, antibodies, host cells, agonists or antagonists or diluents. Generally, such carriers should be nontoxic to recipients at the dosages and concentrations employed. Ordinarily, the preparation of such composition entails combining the therapeutic agent with buffers, antioxidants such as ascorbic acid, low molecular weight (less than about 10 amino acid residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

In addition, the pharmaceutical compositions of the present invention may be prepared for administration by a variety of different routes, although intracranial routes are typically preferred. In addition, pharmaceutical compositions of the present invention may be placed within containers, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition.

As will be evident to one of skill in the art, the amount and frequency of administration will depend, of course, on such factors as the nature and severity of the indication being treated, the desired response, the condition of the patient, and so forth. Typically, the compositions may be administered by a variety of techniques, although intra-cranial routes are often preferred.

More specifically, the pharmaceutical compositions of the present invention will be formulated and dosed in a fashion consistent with good medical practice, taking into account the clinical condition of the individual patient, the site of delivery of the polypeptide composition, the method of administration, the scheduling of administration, and other factors known to practitioners. The "effective amount" of pharmaceutical composition for purposes herein is thus determined by such considerations.

As a general proposition, the total pharmaceutically effective amount of active ingredient administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the composition is typically administered at a dose rate of about 1 μg/kg/hour to about 50 μg/kg/hour, either by 1–4 injections per day or by continuous subcutaneous infusions, for example, using a mini-pump. An intravenous bag solution may also be employed. The key factor in selecting an appropriate dose is the result obtained. The length of treatment needed to observe changes and the interval following treatment for responses to occur appears to vary depending on the desired effect.

Pharmaceutical compositions containing the PS1 proteins, nucleic acid molecules, vectors, antibodies, host cells, agonists or antagonists of the invention may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The pharmaceutical composition is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(-)-3-hydroxybutyric acid (EP 133,988). Sustained-release compositions also include liposomally entrapped PS1 proteins, nucleic acid molecules, vectors, antibodies, host cells, agonists or antagonists. Such liposomes are prepared by methods known per se: DE 3,218, 121; Epstein et al., *Proc. Natl. Acad. Sci.* (*USA*) 82:3688–3692 (1985); Hwang et al., *Proc. Natl. Acad. Sci.* (*USA*) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimaltherapy.

For parenteral administration, in one embodiment, the composition is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the PS1 proteins, nucleic acid molecules, vectors, antibodies, host cells, agonists or antagonists uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Nonaqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The PS1 proteins, nucleic acid molecules, vectors, antibodies, host cells, agonists or antagonists are generally formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Pharmaceutical compositions to be used for therapeutic administration must be sterile. Sterility is readily accomplished by filtration through sterile filtration membranes (e.g., 0.2 micron membranes). Therapeutic compositions generally are placed into a container having a sterile access port, for example, an intravenous solution bag or vial having a stopper pierceable by a hypodermic injection needle.

Pharmaceutical compositions ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous PS1 protein solution, and the resulting mixture is lyophilized. The infusion solution is prepared by reconstituting the lyophilized PS1 polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Within other embodiments of the invention, the vectors which contain or express the nucleic acid molecules which encode a PS1 protein, or even the nucleic acid molecule per se may be administered by a variety of alternative techniques, including for example administration of asialoosomucoid (ASOR) conjugated with poly (L-lysine) DNA complexes (Cristano et al., *Proc. Natl. Acad. Sci. USA* 92122–92126 (1993)), DNA linked to killed adenovirus (Curiel et al., *Hum. Gene Ther.* 3(2):147–154 (1992)), cytofectin-mediated introduction (DMRIE-DOPE, Vical, Calif.), direct DNA injection (Acsadi et al., *Nature* 352:815–818 (1991)); DNA ligand (Wu et al., *J. Biol. Chem.* 264:16985–16987, 1989); lipofection (Felgner et al., *Proc. Natl. Acad. Sci. USA* 84:7413–7417 (1989)); liposomes (Pickering et al., *Circ.* 89(1):13–21 (1994); and Wang et al., *Proc. Natl. Acad. Sci. USA* 84:7851–7855 (1987)); micro-projectile bombardment (Williams et al., *Proc. Natl. Acad. Sci. USA* 88:2726–2730 (1991)); and direct delivery of nucleic acids which encode the PS1 protein alone (Vile and Hart, *Cancer Res.* 53:3860–3864 (1993)), or utilizing PEG-nucleic acid complexes.

All patents and publications mentioned hereinabove are hereby expressly incorporated in their entirety by reference.

In order that those skilled in the art can more fully understand this invention the following examples are set forth. These examples are given solely for the purpose of illustration, and should not be considered as expressing limitations unless so set forth in the appended claims.

EXAMPLES

In the following examples and protocols, restriction enzymes, ligase, and all commercially available reagents were utilized in accordance with the manufacturer's recommendations. Standard methods and techniques for cloning and molecular analysis, as well as the preparation of standard reagents were performed essentially in accordance with *Molecular Cloning: A Laboratory Manual, second edition*, edited by Sambrook, Fritsch & Maniatis, Cold Spring Harbor Laboratory, 1989).

Example 1

Screening of S182 Gene

Although early-onset AD is less common than late-onset AD, the PS1 locus is associated with the most aggressive form of the disease (onset 30–60 years), suggesting the importance of mutations in the PS1 locus with regard to causative effects of AD. The PS1 locus has been isolated to the region between D14S53 and D15S58 on human chromosome 14. Within that region, Sherrington et al., *Nature* 375:754–760 (1995) reported the cloning of a novel gene, S182, with five missense mutations in seven pedigrees segregating early-onset autosomal dominant AD.

To confirm the nucleotide sequence differences, and to assess the segregation in each FAD pedigree and the frequency in the general population (age >65 years), the exon of S182 containing the L286V mutation reported by Sherrington et al., supra, was screened as follows. First the PCR amplified exon containing the L286V mutation was restriction digested by Pvu II as described by Sherrington et al., supra; then the fragments were analyzed by means of a single strand conformation polymorphism (SSCP) analysis. The analysis was performed on 29 early-onset FAD kindreds (who are also negative for the five Sherrington et al.-reported mutations in S182) and from the 12 late-onset families. Each kindred was represented by two patients in the analysis. Also included were samples from 53 age matched controls from the FAD kindred to ascertain the validity of the results.

Genomic DNA from peripheral blood samples was PCR amplified to expedite the screening process. The PCR mixture was prepared for each sample according to the following protocol. Each 10 $\mu$L PCR reaction mixture contained: 1 $\mu$L Taq® buffer; 1.25 mM dNTPs (10 $\mu$L d[A,T,G,C] TP each stock, 760 $\mu$L HPLC water); 1 $\mu$L diluted primer mix (8 $\mu$L primers 7672* and 7673* in 200$\mu$ HPLC water); 0.1 $\mu$L Taq® DNA polymerase; 0.1 $\mu$L $\alpha^{32}$P-dATP; 1 $\mu$L 1:50 genomic DNA (approx. 40 ng, diluted with HPLC water); 5.2 $\mu$L HPLC water. The reaction conditions for each 10 $\mu$L reaction volume were: 94° C. for 4 min.; followed by 30 cycles of (94° C. for 1 min.; 58° C. for 1 min.; 72° C. for 1 min.); then 72° C. for 10 min.; followed by soaking at 4° C. until removed and stored at −20° C.

Primer KM 7672 Sequence: CACCCATTTACAAGTT-TAGC (SEQ ID NO:5);

Primer KM 7673 Sequence: GATGAGACAAGTGC-CGTGAA (SEQ ID NO:6).

After amplification, 3 $\mu$L of each PCR reaction mixture was removed from under the oil and transferred to a new plate containing 30 $\mu$L of SSCP dilution mix in each corresponding well. (SSCP dilution mix: 250 $\mu$L 20% SDS,; 1 mL 0.5M EDTA; Millipore® water to 50 mL). 30 $\mu$L 95% formamide dye mix was then added to each SSCP-diluted 33 $\mu$L sample. (Formamide dye mix: 0.25% bromophenol blue; 0.25% xylene cyanol FF; 95% formamide).

After 30 $\mu$L of the diluted, dyed sample was removed and set aside on ice for later use as a non-denaturing control, the samples were denatured at 90° C. for 10 min., then placed on ice. The denatured samples were loaded onto a Mutation Detection Enhancement (MDE™) gel (FMC® Bioproducts, Rockland, Me.) in 0.6×TBE buffer and run at 15 Watts for 20 hours. (MDE™ gel: 25% 2×gel concentrate; 10% glycerol; 0.6×TBE; to volume with HPLC water). Positive, negative and non-denatured controls were run with each gel, and a water control was run in one gel. The dyes permitted visualization and rapid comparison of the genetic mutations and polymorphisms in contrast to the normal (wild-type) samples.

Using the SSCA analysis, the sequence obtained from a patient carrying a mutation within the S182 exon can be potentially distinguished from that of a normal control individual. One or more mutation(s) in the S182 exon effecting a conformational change in the secondary/tertiary structure can be quickly visualized in the single stranded molecule. The MDE™ gel is designed to permit more compact molecules to run more quickly through the pores of the size differentiating gel, so that a mutated species is revealed as a band in the gel at a different point than that which is consistently seen in normal (control) samples encoded by the same S182 exon region.

The SSCP analysis did not identify the L286V mutation reported by Sherrington et al., supra; however, it did reveal three heterozygous nucleotide substitutions in PS1 in specific probands (see Example 2), which were not found in other pedigrees. Moreover, none of the three mutations was observed in the 106 chromosomes from age-matched controls used to ascertain the FAD pedigrees tested.

Example 2

Detection of Mutations

Three previously unidentified, but apparently pathogenic, mutations in the S182 gene on chromosome 14 have been discovered that appear to cause early-onset forms of familial Alzheimer's disease (FAD). Specifically, the pathogenic mutations found in the S182 exon were: (1) T→C at nucleotide position 1035 (SEQ ID NO:27); (2) C→T at nucleotide position 1039 (SEQ ID NO:29); and (3) G→A at nucleotide position 1054 (SEQ ID NO:-). Each of the exonic mutations are missense substitutions which occur immediately at the C-terminal side of the sixth predicted transmembrane domain (TMD6) of the PS1 protein.

The first mutation results in an amino acid substitution at residue 263 of an arginine for a cysteine (C263R). The second mutation results in an amino acid substitution at residue 264 of a leucine for a proline (P264L). The third mutation results in an amino acid substitution at residue 269 of a histidine for an arginine (R269H).

In addition, two polymorphisms in the intronic sequence flanking the exon of S182 were found: (1) A→C, at nucleotide position −16 of the intron situated 3' of the exon; and (2) A→G at nucleotide position −20 of the intron situated 5' of the same exon.

C263R occurs in the proband of pedigree MGH12. At onset the proband was 47 years old. Autopsy results confirmed that the proband was afflicted with Alzheimer's disease. The C263R mutation was also found in all four other affected individuals from the same pedigree, MGH12 (average age at onset was 50 years).

P264L was observed in the proband of pedigree MGH6. At onset the proband was 45 years old, with a history of thyroid problems. The proband's brother developed AD at 50 years of age, and was autopsy-confirmed as having AD.

R269H was observed in a sporadic case of early-onset Alzheimer's disease. The patient's memory impairment began at about age 47, and he died at age 56. The neuropathology discovered during autopsy confirmed the earlier clinical diagnosis of AD, and the patient was found to have moderate congofilic angiopathy. The patient's father died in his early 60's of stroke, but he had presented a clinical picture of memory decline and progressive cognitive degeneration beginning in his mid-50's. The patient's grandfather (on his father's side) dies in his early 70's, but his previous history presented a gradual cognitive impairment that may have been ongoing since his mid-60's.

No formal clinical or neuropathological diagnosis was established for any member of this family exhibiting mutation R269H. At the time of the study, the patient's mother remained alive and well, without cognitive impairment; whereas his sister died of cancer in her late 50's-early 60's; the sister's son, however, remained healthy.

The fact that the newly identified mutations are presumably pathogenic is strongly supported by the profound effect that the substitutions impart on the resulting protein. The C263R, P264L, and R269H mutations reside in the predicted hydrophilic loop domain, and immediately follow the C-terminus of TMD6. Consequently, the mutations could extend the length of the transmembrane domain, thereby aberrantly affecting the anchorage of the protein in the membrane. Alternatively, the mutations may adversely affect the secondary/tertiary structure of the hydrophilic loop and/ or the entire protein.

It is interesting to note that each of the newly identified mutations fall in the region in and around TMD6, which also contains the A246E mutation reported by Sherrington et al., *Nature* (1995), supra. Moreover, the average age at onset of AD in the three individuals or families characterized by the newly identified mutations is very similar (approximately age 50) to those having the A246E mutation. This indicates that disruptions in the PS1 protein, particularly in and around TMD6, may result in similar pathogenic consequences. Accordingly, the newly identified mutations represent the most significant amino acid changes reported in S182 to date affecting early onset AD.

What is claimed is:

1. An isolated nucleic acid fragment comprising a nucleotide sequence selected from the group consisting of:
   (a) a nucleotide sequence encoding a mutant presenilin 1 (PS1) polypeptide consisting of the amino acid sequence shown in SEQ ID NO:28; and
   (b) a nucleotide sequence encoding a mutant PS1 polypeptide consisting of the nucleotide sequence shown in SEQ ID NO:27.

2. An isolated nucleic acid fragment comprising a nucleotide sequence fully complementary to the nucleotide sequence of claim 1.

3. A method of making a vector, said method comprising inserting the nucleic acid fragment of claim 1 into a vector.

4. A vector comprising the nucleic acid fragment of claim 1.

5. A method of making a recombinant host cell, said method comprising introducing the vector of claim 4 into an isolated host cell.

6. A recombinant host cell comprising the vector of claim 4.

7. A method of producing a mutant PS1 polypeptide, said method comprising culturing the recombinant host cell of claim 6 under conditions such that said polypeptide is expressed, and recovering said polypeptide.

8. An isolated nucleic acid fragment consisting essentially of a nucleotide sequence selected from the group consisting of:
   (a) a nucleotide sequence of 18 to less than 1500 nucleotides in lenth, wherein said nucleotide sequence encodes 6 amino acids or more of SEQ ID NO:28 and said amino acids span amino acid residue 263 of said SEQ ID NO:28;
   (b) a nucleotide sequence of 18 to less than 1500 nucleotides in length, wherein said nucleotide sequence is a fragment of a nucleotide sequence shown in SEQ ID NO:27 encoding a mutant PS1 polypeptide and said fragment contains a T→C mutation at nucleotide position 1035 of said nucleotide sequence; and
   (c) a nucleotide sequence fully complementary to the nucleotide sequence in (a) or (b).

9. The isolated nucleic acid fragment of claim 8, wherein said nucleotide sequence is about 75 to less than 1500 nucleotides.

10. A method of making a vector, said method comprising inserting the nucleic acid fragment ot claim 8 into a vector.

11. A vector comprising the nucleic acid fragment of claim 8.

12. A method of making a recombinant host cell, said method comprising introducing the vector of claim 11 into an isolated host cell.

13. A recombinant host cell comprising the vector of claim 11.

14. An isolated nucleic acid fragment comprising a nucleotide sequence selected from the group consisting of:
   (a) a nucleotide sequence encoding a mutant presenilin 1 (PS2) polypeptide consisting of the amino acid sequence shown in SEQ ID NO:30; and
   (b) a nucleotide scquence encoding a mutant PS1 polypeptide consisting of the nucleotide sequence shown in SEQ ID NO:29.

15. An isolated nucleic acid fragment comprising a nucleotide sequence fully complementary to the nucleotide sequence of claim 14.

16. A method of making a vector, said method comprising inserting the nucleic acid fragment of claim 14 into a vector.

17. A vector comprising the nucleic acid fragment of claim 14.

18. A method of making a recombinant host cell, said method comprising introducing the vector of claim 17 into an isolated host cell.

19. A rcombinant host cell comprising the vector of claim 17.

20. A method of producing a mutant PS1 polypeptide, said method comprising culturing the recombinant host cell of claim 19 under conditions such that said polypeptide is expressed, and recovering said polypeptide.

21. An isolated nucleic acid fragment consisting essentially of a nucleotide sequence selected from the group consisting of:
   (a) a nucleotide sequence of 18 to less than 1500 nucleotides in length, wherein said nucleotide sequence encodes 6 amino acids or more of SEQ ID NO:30 and said amino acids span amino acid residue 264 of said SEQ ID NO:30;
   (h) a nucleotide sequence of 18 to less than 1500 nucleotides in length, wherein said nucleotide sequence is a fragment of a nucleotide sequence shown in SEQ ID NO:29 encoding a mutant PS1 polypeptide and said fragment contains a C→T mutation at nucleotide position 1039 of said nucleotide sequence; and
   (c) a nucleotide sequence fully complementary to the nucleotide sequence in (a) or (b).

22. The isolated nucleic acid fragment of claim 21, wherein said nucleotide sequence is about 75 to less than 1500 nucleotides.

23. A method of making a vector, said method comprising inserting the nucleic acid fragment of claim 21 into a vector.

24. A vector comprising the nucleic acid fragment of claim 21.

25. A method of making a recombinant host cell, said method comprising introducing the vector of claim 24 into an isolated host cell.

26. A recombinant host cell comprising the vector of claim 24.

27. An isolated nucleic acid fragment comprising a nucleotide sequence selected from the group consisting of:
   (a) a nucleotide sequence encoding a mutant presenilin 1 (PS1) polypeptide consisting of the amino acid sequence shown in SEQ ID NO:32; and
   (b) a nucleotide sequence encoding a mutant PS1 polypeptide consisting of the nucleotide sequence shown in SEQ ID NO:31.

28. An isolated nucleic acid fragment comprising a nucleotide sequence fully complementary to the nucleotide sequence of claim 27.

29. A method of making a vector, said method comprising inserting the nucleic acid fragment of claim 27 into a vector.

30. A vector comprising the nucleic acid fragment of claim 27.

31. A method of making a recombinant host cell, said method comprising introducing the vector of claim 30 into an isolated host cell.

32. A recombinant host cell comprising the vector of claim 30.

33. A method of producing a mutant PS1 polypeptide, said method comprising cultivating the recombinant host cell of claim 32 under conditions such that said polypeptide is expressed, and recovering said polypeptide.

34. An isolated nucleic acid fragment consisting essentially of a nucleotide sequence selected from the group consisting of:

(a) a nucleotide sequence of 18 to less than 1500 nucleotides in length, wherein said nucleotide sequence encodes 6 amino acids or more of SEQ ID NO:32 and said amino acids span amino acid residue 269 of said SEQ ID NO:32;

(b) a nucleotide sequence of 18 to less than 1500 nucleotides in length, wherein said nucleotide sequence is a fragment of a nucleotide sequence shown in SEQ ID NO:31 encoding a mutant PS1 polypeptide and said fragment contains a G→A mutation at nucleotide position 1054 of said nucleotide sequence; and (c) a nucleotide sequence fully complementary to the nucleotide sequence in (a) or (b).

35. The isolated nucleic acid fragment of claim 34, wherein said nucleotide sequence is about 75 to less than 1500 nucleotides.

36. A method of making a vector, said method comprising inserting the nucleic acid fragment of claim 34 into a vector.

37. A vector comprising the nucleic acid fragment of claim 34.

38. A method of making a recombinant host cell, said method comprising introducing the vector of claim 37 into an isolated host cell.

39. A recombinant host cell comprising the vector of claim 37.

40. An isolated nucleic acid fragment comprising a nucleotide sequence selected from the group consisting of:

(a) a nucleotide sequence encoding a mutant presenilin 1 (PS1) polypeptide consisting of the amino acid sequece as shown in SEQ ID NO:4; and (b) a nucleotide sequence encoding a mutant PS1 polypeptide consisting of the nucleotide sequence shown in SEQ ID NO:3.

41. An isolated nucleic acid fragment comprising a nucleotide sequence fully complimentary to the nucleotide sequence of claim 40.

42. A method of making a vector, said method comprising inserting the nucleic acid fragment of claim 40 into a vector.

43. A vector comprising the nucleic acid fragment of claim 40.

44. A method of making a recombinant host cell, said method comprising introducing the vector of claim 43 into an isolated host cell.

45. A recombinant host cell comprising the vector of claim 43.

46. A method of producing a mutant PS1 polypeptide, said method comprising culturing the recombinant host cell of claim 45 under conditions such that said polypeptide is expressed, and recovering said polypeptide.

47. An isolated nucleic acid fragment consisting essentially of a nucleotide sequence selected from the group consisting of:

(a) a nucleotide sequence of 18 to less than 1500 nucleotides in length, wherein said nucleotide sequence encodes 6 amino acids or more of SEQ ID NO:4 and said amino acids span amino acid residues 263, 264 and 269 of said SEQ ID NO:4;

(b) a nucleotide sequence of 18 to less than 1500 nucleotides in length, wherein said nucleotide sequence is a fragment of a nucleotide sequence shown in SEQ ID NO:3 encoding a mutant PS1 polypeptide and said fragment contains a T→C mutation at nucleotide position 1035 of said nucleotide sequence, a C→T mutation at nucleotide position 1039 of said nucleotide sequence, and a G→A mutation at nucleotide position 1054 of said nucleotide sequence; and (c) a nucleotide sequence fully complimentary to the nucleotide sequence in (a) or (b).

48. The isolated nucleic acid fragment of claim 47, wherein said nucleotide sequence is about 75 to less than 1500 nucleotides.

49. A method of making a vector, said method comprising inserting the nucleic acid fragment of claim 47 into a vector.

50. A vector comprising the nucleic acid fragment of claim 47.

51. A method of making a recombinant host cell, said method comprising introducing the vector of claim 50 into an isolated host cell.

52. A recombinant host cell comprising the vector of claim 50.

* * * * *

SEQUENCE LISTING (1) GENERAL INFORMATION:

(iii) NUMBER OF SEQUENCES: 32

(2) INFORMATION FOR SEQ ID NO: 1:

(i) SEQUENCE CHARACTERISTICS:
      (A) LENGTH: 2765 base pairs
      (B) TYPE: nucleic acid

```
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION:249..1649

(xi) SEQUENCE DESCRIPTION: SEQ ID NO: 1:

TGGGACAGGC AGCTCCGGGG TCCGCGGTTT CACATCGGAA ACAAAACAGC GGCTGGTCTG      60

GAAGGAACCT GAGCTACGAG CCGCGGCGGC AGCGGGGCGG CGGGGAAGCG TATACCTAAT    120

CTGGGAGCCT GCAAGTGACA ACAGCCTTTG CGGTCCTTAG ACAGCTTGGC CTGGAGGAGA    180

ACACATGAAA GAAAGAACCT CAAGAGGCTT TGTTTTCTGT GAAACAGTAT TTCTATACAG    240

TTGCTCCA ATG ACA GAG TTA CCT GCA CCG TTG TCC TAC TTC CAG AAT GCA     290
         Met Thr Glu Leu Pro Ala Pro Leu Ser Tyr Phe Gln Asn Ala
           1               5                  10

CAG ATG TCT GAG GAC AAC CAC CTG AGC AAT ACT GTA CGT AGC CAG AAT       338
Gln Met Ser Glu Asp Asn His Leu Ser Asn Thr Val Arg Ser Gln Asn
 15              20                  25                  30

GAC AAT AGA GAA CGG CAG GAG CAC AAC GAC AGA CGG AGC CTT GGC CAC       386
Asp Asn Arg Glu Arg Gln Glu His Asn Asp Arg Arg Ser Leu Gly His
             35                  40                  45

CCT GAG CCA TTA TCT AAT GGA CGA CCC CAG GGT AAC TCC CGG CAG GTG       434
Pro Glu Pro Leu Ser Asn Gly Arg Pro Gln Gly Asn Ser Arg Gln Val
         50                  55                  60

GTG GAG CAA GAT GAG GAA GAA GAT GAG GAG CTG ACA TTG AAA TAT GGC       482
Val Glu Gln Asp Glu Glu Glu Asp Glu Glu Leu Thr Leu Lys Tyr Gly
 65                  70                  75

GCC AAG CAT GTG ATC ATG CTC TTT GTC CCT GTG ACT CTC TGC ATG GTG       530
Ala Lys His Val Ile Met Leu Phe Val Pro Val Thr Leu Cys Met Val
             80                  85                  90

GTG GTC GTG GCT ACC ATT AAG TCA GTC AGC TTT TAT ACC CGG AAG GAT       578
Val Val Val Ala Thr Ile Lys Ser Val Ser Phe Tyr Thr Arg Lys Asp
 95                  100                 105                 110

GGG CAG CTA ATC TAT ACC CCA TTC ACA GAA GAT ACC GAG ACT GTG GGC       626
Gly Gln Leu Ile Tyr Thr Pro Phe Thr Glu Asp Thr Glu Thr Val Gly
             115                 120                 125

CAG AGA GCC CTG CAC TCA ATT CTG AAT GCT GCC ATC ATG ATC AGT GTC       674
Gln Arg Ala Leu His Ser Ile Leu Asn Ala Ala Ile Met Ile Ser Val
         130                 135                 140

ATT GTT GTC ATG ACT ATC CTC CTG GTG GTT CTG TAT AAA TAC AGG TGC       722
Ile Val Val Met Thr Ile Leu Leu Val Val Leu Tyr Lys Tyr Arg Cys
             145                 150                 155

TAT AAG GTC ATC CAT GCC TGG CTT ATT ATA TCA TCT CTA TTG TTG CTG       770
Tyr Lys Val Ile His Ala Trp Leu Ile Ile Ser Ser Leu Leu Leu Leu
 160                 165                 170

TTC TTT TTT TCA TTC ATT TAC TTG GGG GAA GTG TTT AAA ACC TAT AAC       818
Phe Phe Phe Ser Phe Ile Tyr Leu Gly Glu Val Phe Lys Thr Tyr Asn
175                 180                 185                 190

GTT GCT GTG GAC TAC ATT ACT GTT GCA CTC CTG ATC TGG AAT TTT GGT       866
Val Ala Val Asp Tyr Ile Thr Val Ala Leu Leu Ile Trp Asn Phe Gly
             195                 200                 205

GTG GTG GGA ATG ATT TCC ATT CAC TGG AAA GGT CCA CTT CGA CTC CAG       914
Val Val Gly Met Ile Ser Ile His Trp Lys Gly Pro Leu Arg Leu Gln
         210                 215                 220

CAG GCA TAT CTC ATT ATG ATT AGT GCC CTC ATG GCC CTG GTG TTT ATC       962
Gln Ala Tyr Leu Ile Met Ile Ser Ala Leu Met Ala Leu Val Phe Ile
             225                 230                 235
```

```
                                                            -continued

AAG TAC CTC CCT GAA TGG ACT GCG TGG CTC ATC TTG GCT GTG ATT TCA     1010
Lys Tyr Leu Pro Glu Trp Thr Ala Trp Leu Ile Leu Ala Val Ile Ser
    240                 245                 250

GTA TAT GAT TTA GTG GCT GTT TTG TGT CCG AAA GGT CCA CTT CGT ATG     1058
Val Tyr Asp Leu Val Ala Val Leu Cys Pro Lys Gly Pro Leu Arg Met
255                 260                 265                 270

CTG GTT GAA ACA GCT CAG GAG AGA AAT GAA ACG CTT TTT CCA GCT CTC     1106
Leu Val Glu Thr Ala Gln Glu Arg Asn Glu Thr Leu Phe Pro Ala Leu
                275                 280                 285

ATT TAC TCC TCA ACA ATG GTG TGG TTG GTG AAT ATG GCA GAA GGA GAC     1154
Ile Tyr Ser Ser Thr Met Val Trp Leu Val Asn Met Ala Glu Gly Asp
            290                 295                 300

CCG GAA GCT CAA AGG AGA GTA TCC AAA AAT TCC AAG CAT AAT GCA GAA     1202
Pro Glu Ala Gln Arg Arg Val Ser Lys Asn Ser Lys His Asn Ala Glu
        305                 310                 315

AGC ACA GAA AGG GAG TCA CAA GAC ACT GTT GCA GAG AAT GAT GAT GGC     1250
Ser Thr Glu Arg Glu Ser Gln Asp Thr Val Ala Glu Asn Asp Asp Gly
    320                 325                 330

GGG TTC AGT GAG GAA TGG GAA GCC CAG AGG GAC AGT CAT CTA GGG CCT     1298
Gly Phe Ser Glu Glu Trp Glu Ala Gln Arg Asp Ser His Leu Gly Pro
335                 340                 345                 350

CAT CGC TCT ACA CCT GAG TCA CGA GCT GCT GTC CAG GAA CTT TCC AGC     1346
His Arg Ser Thr Pro Glu Ser Arg Ala Ala Val Gln Glu Leu Ser Ser
                355                 360                 365

AGT ATC CTC GCT GGT GAA GAC CCA GAG GAA AGG GGA GTA AAA CTT GGA     1394
Ser Ile Leu Ala Gly Glu Asp Pro Glu Glu Arg Gly Val Lys Leu Gly
            370                 375                 380

TTG GGA GAT TTC ATT TTC TAC AGT GTT CTG GTT GGT AAA GCC TCA GCA     1442
Leu Gly Asp Phe Ile Phe Tyr Ser Val Leu Val Gly Lys Ala Ser Ala
        385                 390                 395

ACA GCC AGT GGA GAC TGG AAC ACA ACC ATA GCC TGT TTC GTA GCC ATA     1490
Thr Ala Ser Gly Asp Trp Asn Thr Thr Ile Ala Cys Phe Val Ala Ile
    400                 405                 410

TTA ATT GGT TTG TGC CTT ACA TTA TTA CTC CTT GCC ATT TTC AAG AAA     1538
Leu Ile Gly Leu Cys Leu Thr Leu Leu Leu Ala Ile Phe Lys Lys
415                 420                 425                 430

GCA TTG CCA GCT CTT CCA ATC TCC ATC ACC TTT GGG CTT GTT TTC TAC     1586
Ala Leu Pro Ala Leu Pro Ile Ser Ile Thr Phe Gly Leu Val Phe Tyr
                435                 440                 445

TTT GCC ACA GAT TAT CTT GTA CAG CCT TTT ATG GAC CAA TTA GCA TTC     1634
Phe Ala Thr Asp Tyr Leu Val Gln Pro Phe Met Asp Gln Leu Ala Phe
            450                 455                 460

CAT CAA TTT TAT ATC TAGCATATTT GCGGTTAGAA TCCCATGGAT GTTTCTTCTT     1689
His Gln Phe Tyr Ile
            465

TGACTATAAC CAAATCTGGG GAGGACAAAG GTGATTTTCC TGTGTCCACA TCTAACAAAG   1749

TCAAGATTCC CGGCTGGACT TTTGCAGCTT CCTTCCAAGT CTTCCTGACC ACCTTGCACT   1809

ATTGGACTTT GGAAGGAGGT GCCTATAGAA AACGATTTTG AACATACTTC ATCGCAGTGG   1869

ACTGTGTCCC TCGGTGCAGA AACTACCAGA TTTGAGGGAC GAGGTCAAGG AGATATGATA   1929

GGCCCGGAAG TTGCTGTGCC CCATCAGCAG CTTGACGCGT GGTCACAGGA CGATTTCACT   1989

GACACTGCGA ACTCTCAGGA CTACCGGTTA CCAAGAGGTT AGGTGAAGTG GTTTAAACCA   2049

AACGGAACTC TTCATCTTAA ACTACACGTT GAAAATCAAC CCAATAATTC TGTATTAACT   2109

GAATTCTGAA CTTTTCAGGA GGTACTGTGA GGAAGAGCAG GCACCAGCAG CAGAATGGGG   2169

AATGGAGAGG TGGGCAGGGG TTCCAGCTTC CCTTTGATTT TTTGCTGCAG ACTCATCCTT   2229

TTTAAATGAG ACTTGTTTTC CCCTCTCTTT GAGTCAAGTC AAATATGTAG ATTGCCTTTG   2289
```

```
GCAATTCTTC TTCTCAAGCA CTGACACTCA TTACCGTCTG TGATTGCCAT TTCTTCCCAA    2349

GGCCAGTCTG AACCTGAGGT TGCTTTATCC TAAAAGTTTT AACCTCAGGT TCCAAATTCA    2409

GTAAATTTTG GAAACAGTAC AGCTATTTCT CATCAATTCT CTATCATGTT GAAGTCAAAT    2469

TTGGATTTTC CACCAAATTC TGAATTTGTA GACATACTTG TACGCTCACT TGCCCCCAGA    2529

TGCCTCCTCT GTCCTCATTC TTCTCTCCCA CACAAGCAGT CTTTTTCTAC AGCCAGTAAG    2589

GCAGCTCTGT CRTGGTAGCA GATGGTCCCA TTATTCTAGG GTCTTACTCT TTGTATGATG    2649

AAAAGAATGT GTTATGAATC GGTGCTGTCA GCCCTGCTGT CAGACCTTCT TCCACAGCAA    2709

ATGAGATGTA TGCCCAAAGC GGTAGAATTA AGAAGAGTA AAATGGCTGT TGAAGC        2765
```

(2) INFORMATION FOR SEQ ID NO: 2:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Thr Glu Leu Pro Ala Pro Leu Ser Tyr Phe Gln Asn Ala Gln Met
 1               5                  10                  15

Ser Glu Asp Asn His Leu Ser Asn Thr Val Arg Ser Gln Asn Asp Asn
             20                  25                  30

Arg Glu Arg Gln Glu His Asn Asp Arg Arg Ser Leu Gly His Pro Glu
         35                  40                  45

Pro Leu Ser Asn Gly Arg Pro Gln Gly Asn Ser Arg Gln Val Val Glu
     50                  55                  60

Gln Asp Glu Glu Glu Asp Glu Glu Leu Thr Leu Lys Tyr Gly Ala Lys
 65                  70                  75                  80

His Val Ile Met Leu Phe Val Pro Val Thr Leu Cys Met Val Val Val
                 85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270
```

-continued

```
Glu Thr Ala Gln Glu Arg Asn Glu Thr Leu Phe Pro Ala Leu Ile Tyr
            275                 280                 285

Ser Ser Thr Met Val Trp Leu Val Asn Met Ala Glu Gly Asp Pro Glu
        290                 295                 300

Ala Gln Arg Arg Val Ser Lys Asn Ser Lys His Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
        355                 360                 365

Leu Ala Gly Glu Asp Pro Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Ala Ile Phe Lys Lys Ala Leu
            420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465
```

(2) INFORMATION FOR SEQ ID NO: 3:

(i) SEQUENCE CHARACTERISTICS:
        (A) LENGTH: 2765 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:249..1649

(xi) SEQUENCE DESCRIPTION: SEQ ID NO: 3:

```
TGGGACAGGC AGCTCCGGGG TCCGCGGTTT CACATCGGAA ACAAAACAGC GGCTGGTCTG      60

GAAGGAACCT GAGCTACGAG CCGCGGCGGC AGCGGGGCGG CGGGGAAGCG TATACCTAAT     120

CTGGGAGCCT GCAAGTGACA ACAGCCTTTG CGGTCCTTAG ACAGCTTGGC CTGGAGGAGA     180

ACACATGAAA GAAAGAACCT CAAGAGGCTT TGTTTTCTGT GAAACAGTAT TTCTATACAG     240

TTGCTCCA ATG ACA GAG TTA CCT GCA CCG TTG TCC TAC TTC CAG AAT GCA     290
         Met Thr Glu Leu Pro Ala Pro Leu Ser Tyr Phe Gln Asn Ala
           1               5                  10

CAG ATG TCT GAG GAC AAC CAC CTG AGC AAT ACT GTA CGT AGC CAG AAT     338
Gln Met Ser Glu Asp Asn His Leu Ser Asn Thr Val Arg Ser Gln Asn
 15                  20                  25                  30

GAC AAT AGA GAA CGG CAG GAG CAC AAC GAC AGA CGG AGC CTT GGC CAC     386
Asp Asn Arg Glu Arg Gln Glu His Asn Asp Arg Arg Ser Leu Gly His
                 35                  40                  45

CCT GAG CCA TTA TCT AAT GGA CGA CCC CAG GGT AAC TCC CGG CAG GTG     434
Pro Glu Pro Leu Ser Asn Gly Arg Pro Gln Gly Asn Ser Arg Gln Val
```

-continued

```
                        50                           55                           60
GTG GAG CAA GAT GAG GAA GAA GAT GAG GAG CTG ACA TTG AAA TAT GGC                482
Val Glu Gln Asp Glu Glu Glu Asp Glu Glu Leu Thr Leu Lys Tyr Gly
                65                           70                       75

GCC AAG CAT GTG ATC ATG CTC TTT GTC CCT GTG ACT CTC TGC ATG GTG                530
Ala Lys His Val Ile Met Leu Phe Val Pro Val Thr Leu Cys Met Val
        80                           85                       90

GTG GTC GTG GCT ACC ATT AAG TCA GTC AGC TTT TAT ACC CGG AAG GAT                578
Val Val Val Ala Thr Ile Lys Ser Val Ser Phe Tyr Thr Arg Lys Asp
 95                          100                         105             110

GGG CAG CTA ATC TAT ACC CCA TTC ACA GAA GAT ACC GAG ACT GTG GGC                626
Gly Gln Leu Ile Tyr Thr Pro Phe Thr Glu Asp Thr Glu Thr Val Gly
                    115                         120                 125

CAG AGA GCC CTG CAC TCA ATT CTG AAT GCT GCC ATC ATG ATC AGT GTC                674
Gln Arg Ala Leu His Ser Ile Leu Asn Ala Ala Ile Met Ile Ser Val
            130                         135                 140

ATT GTT GTC ATG ACT ATC CTC CTG GTG GTT CTG TAT AAA TAC AGG TGC                722
Ile Val Val Met Thr Ile Leu Leu Val Val Leu Tyr Lys Tyr Arg Cys
        145                         150                 155

TAT AAG GTC ATC CAT GCC TGG CTT ATT ATA TCA TCT CTA TTG TTG CTG                770
Tyr Lys Val Ile His Ala Trp Leu Ile Ile Ser Ser Leu Leu Leu Leu
    160                         165                 170

TTC TTT TTT TCA TTC ATT TAC TTG GGG GAA GTG TTT AAA ACC TAT AAC                818
Phe Phe Phe Ser Phe Ile Tyr Leu Gly Glu Val Phe Lys Thr Tyr Asn
175                         180                 185                 190

GTT GCT GTG GAC TAC ATT ACT GTT GCA CTC CTG ATC TGG AAT TTT GGT                866
Val Ala Val Asp Tyr Ile Thr Val Ala Leu Leu Ile Trp Asn Phe Gly
                    195                 200                 205

GTG GTG GGA ATG ATT TCC ATT CAC TGG AAA GGT CCA CTT CGA CTC CAG                914
Val Val Gly Met Ile Ser Ile His Trp Lys Gly Pro Leu Arg Leu Gln
                210                 215                 220

CAG GCA TAT CTC ATT ATG ATT AGT GCC CTC ATG GCC CTG GTG TTT ATC                962
Gln Ala Tyr Leu Ile Met Ile Ser Ala Leu Met Ala Leu Val Phe Ile
            225                 230                 235

AAG TAC CTC CCT GAA TGG ACT GCG TGG CTC ATC TTG GCT GTG ATT TCA               1010
Lys Tyr Leu Pro Glu Trp Thr Ala Trp Leu Ile Leu Ala Val Ile Ser
        240                 245                 250

GTA TAT GAT TTA GTG GCT GTT TTG CGT CTG AAA GGT CCA CTT CAT ATG               1058
Val Tyr Asp Leu Val Ala Val Leu Arg Leu Lys Gly Pro Leu His Met
255                 260                 265                     270

CTG GTT GAA ACA GCT CAG GAG AGA AAT GAA ACG CTT TTT CCA GCT CTC               1106
Leu Val Glu Thr Ala Gln Glu Arg Asn Glu Thr Leu Phe Pro Ala Leu
                275                 280                     285

ATT TAC TCC TCA ACA ATG GTG TGG TTG GTG AAT ATG GCA GAA GGA GAC               1154
Ile Tyr Ser Ser Thr Met Val Trp Leu Val Asn Met Ala Glu Gly Asp
            290                 295                 300

CCG GAA GCT CAA AGG AGA GTA TCC AAA AAT TCC AAG CAT AAT GCA GAA               1202
Pro Glu Ala Gln Arg Arg Val Ser Lys Asn Ser Lys His Asn Ala Glu
        305                 310                 315

AGC ACA GAA AGG GAG TCA CAA GAC ACT GTT GCA GAG AAT GAT GAT GGC               1250
Ser Thr Glu Arg Glu Ser Gln Asp Thr Val Ala Glu Asn Asp Asp Gly
    320                 325                 330

GGG TTC AGT GAG GAA TGG GAA GCC CAG AGG GAC AGT CAT CTA GGG CCT               1298
Gly Phe Ser Glu Glu Trp Glu Ala Gln Arg Asp Ser His Leu Gly Pro
335                 340                 345                 350

CAT CGC TCT ACA CCT GAG TCA CGA GCT GCT GTC CAG GAA CTT TCC AGC               1346
His Arg Ser Thr Pro Glu Ser Arg Ala Ala Val Gln Glu Leu Ser Ser
                355                 360                 365

AGT ATC CTC GCT GGT GAA GAC CCA GAG GAA AGG GGA GTA AAA CTT GGA               1394
Ser Ile Leu Ala Gly Glu Asp Pro Glu Glu Arg Gly Val Lys Leu Gly
```

```
Ser Ile Leu Ala Gly Glu Asp Pro Glu Glu Arg Gly Val Lys Leu Gly
            370                 375                 380

TTG GGA GAT TTC ATT TTC TAC AGT GTT CTG GTT GGT AAA GCC TCA GCA      1442
Leu Gly Asp Phe Ile Phe Tyr Ser Val Leu Val Gly Lys Ala Ser Ala
        385                 390                 395

ACA GCC AGT GGA GAC TGG AAC ACA ACC ATA GCC TGT TTC GTA GCC ATA      1490
Thr Ala Ser Gly Asp Trp Asn Thr Thr Ile Ala Cys Phe Val Ala Ile
400                 405                 410

TTA ATT GGT TTG TGC CTT ACA TTA TTA CTC CTT GCC ATT TTC AAG AAA      1538
Leu Ile Gly Leu Cys Leu Thr Leu Leu Leu Ala Ile Phe Lys Lys
415                 420                 425                 430

GCA TTG CCA GCT CTT CCA ATC TCC ATC ACC TTT GGG CTT GTT TTC TAC      1586
Ala Leu Pro Ala Leu Pro Ile Ser Ile Thr Phe Gly Leu Val Phe Tyr
                435                 440                 445

TTT GCC ACA GAT TAT CTT GTA CAG CCT TTT ATG GAC CAA TTA GCA TTC      1634
Phe Ala Thr Asp Tyr Leu Val Gln Pro Phe Met Asp Gln Leu Ala Phe
            450                 455                 460

CAT CAA TTT TAT ATC TAGCATATTT GCGGTTAGAA TCCCATGGAT GTTTCTTCTT      1689
His Gln Phe Tyr Ile
            465

TGACTATAAC CAAATCTGGG GAGGACAAAG GTGATTTTCC TGTGTCCACA TCTAACAAAG    1749

TCAAGATTCC CGGCTGGACT TTTGCAGCTT CCTTCCAAGT CTTCCTGACC ACCTTGCACT    1809

ATTGGACTTT GGAAGGAGGT GCCTATAGAA AACGATTTTG AACATACTTC ATCGCAGTGG    1869

ACTGTGTCCC TCGGTGCAGA AACTACCAGA TTTGAGGGAC GAGGTCAAGG AGATATGATA    1929

GGCCCGGAAG TTGCTGTGCC CCATCAGCAG CTTGACGCGT GGTCACAGGA CGATTTCACT    1989

GACACTGCGA ACTCTCAGGA CTACCGGTTA CCAAGAGGTT AGGTGAAGTG GTTTAAACCA    2049

AACGGAACTC TTCATCTTAA ACTACACGTT GAAAATCAAC CCAATAATTC TGTATTAACT    2109

GAATTCTGAA CTTTTCAGGA GGTACTGTGA GGAAGAGCAG GCACCAGCAG CAGAATGGGG    2169

AATGGAGAGG TGGGCAGGGG TTCCAGCTTC CCTTTGATTT TTTGCTGCAG ACTCATCCTT    2229

TTTAAATGAG ACTTGTTTTC CCCTCTCTTT GAGTCAAGTC AAATATGTAG ATTGCCTTTG    2289

GCAATTCTTC TTCTCAAGCA CTGACACTCA TTACCGTCTG TGATTGCCAT TCTTCCCAA     2349

GGCCAGTCTG AACCTGAGGT TGCTTTATCC TAAAAGTTTT AACCTCAGGT TCCAAATTCA    2409

GTAAATTTTG GAAACAGTAC AGCTATTTCT CATCAATTCT CTATCATGTT GAAGTCAAAT    2469

TTGGATTTTC CACCAAATTC TGAATTTGTA GACATACTTG TACGCTCACT TGCCCCCAGA    2529

TGCCTCCTCT GTCCTCATTC TTCTCTCCCA CACAAGCAGT CTTTTTCTAC AGCCAGTAAG    2589

GCAGCTCTGT CRTGGTAGCA GATGGTCCCA TTATTCTAGG GTCTTACTCT TTGTATGATG    2649

AAAAGAATGT GTTATGAATC GGTGCTGTCA GCCCTGCTGT CAGACCTTCT TCCACAGCAA    2709

ATGAGATGTA TGCCCAAAGC GGTAGAATTA AGAAGAGTA AAATGGCTGT TGAAGC         2765
```

(2) INFORMATION FOR SEQ ID NO: 4:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Thr Glu Leu Pro Ala Pro Leu Ser Tyr Phe Gln Asn Ala Gln Met
 1               5                  10                  15

Ser Glu Asp Asn His Leu Ser Asn Thr Val Arg Ser Gln Asn Asp Asn
```

```
                   20                  25                    30
Arg Glu Arg Gln Glu His Asn Asp Arg Arg Ser Leu Gly His Pro Glu
              35                  40                  45

Pro Leu Ser Asn Gly Arg Pro Gln Gly Asn Ser Arg Gln Val Val Glu
         50                  55                  60

Gln Asp Glu Glu Asp Glu Glu Leu Thr Leu Lys Tyr Gly Ala Lys
65                  70                  75                  80

His Val Ile Met Leu Phe Val Pro Val Thr Leu Cys Met Val Val
                 85                  90                  95

Val Ala Thr Ile Lys Ser Val Ser Phe Tyr Thr Arg Lys Asp Gly Gln
             100                 105                 110

Leu Ile Tyr Thr Pro Phe Thr Glu Asp Thr Glu Thr Val Gly Gln Arg
             115                 120                 125

Ala Leu His Ser Ile Leu Asn Ala Ala Ile Met Ile Ser Val Ile Val
             130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Phe Phe
                 165                 170                 175

Phe Ser Phe Ile Tyr Leu Gly Glu Val Phe Lys Thr Tyr Asn Val Ala
             180                 185                 190

Val Asp Tyr Ile Thr Val Ala Leu Leu Ile Trp Asn Phe Gly Val Val
             195                 200                 205

Gly Met Ile Ser Ile His Trp Lys Gly Pro Leu Arg Leu Gln Gln Ala
             210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
             245                 250                 255

Asp Leu Val Ala Val Leu Arg Leu Lys Gly Pro Leu His Met Leu Val
             260                 265                 270

Glu Thr Ala Gln Glu Arg Asn Glu Thr Leu Phe Pro Ala Leu Ile Tyr
             275                 280                 285

Ser Ser Thr Met Val Trp Leu Val Asn Met Ala Glu Gly Asp Pro Glu
290                 295                 300

Ala Gln Arg Arg Val Ser Lys Asn Ser Lys His Asn Ala Glu Ser Thr
305                 310                 315                 320

Glu Arg Glu Ser Gln Asp Thr Val Ala Glu Asn Asp Gly Gly Phe
             325                 330                 335

Ser Glu Glu Trp Glu Ala Gln Arg Asp Ser His Leu Gly Pro His Arg
             340                 345                 350

Ser Thr Pro Glu Ser Arg Ala Ala Val Gln Glu Leu Ser Ser Ser Ile
             355                 360                 365

Leu Ala Gly Glu Asp Pro Glu Glu Arg Gly Val Lys Leu Gly Leu Gly
             370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                 405                 410                 415

Gly Leu Cys Leu Thr Leu Leu Leu Ala Ile Phe Lys Lys Ala Leu
             420                 425                 430

Pro Ala Leu Pro Ile Ser Ile Thr Phe Gly Leu Val Phe Tyr Phe Ala
             435                 440                 445
```

```
Thr Asp Tyr Leu Val Gln Pro Phe Met Asp Gln Leu Ala Phe His Gln
    450                 455                 460

Phe Tyr Ile
465
```

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

CACCCATTTA CAAGTTTAGC                                      20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

GATGAGACAA GTGCCGTGAA                                      20

(2) INFORMATION FOR SEQ ID NO: 7:

(i) SEQUENCE CHARACTERISTICS:
        (A) LENGTH: 38 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 7:

```
Gly Gln Ala Ala Pro Gly Ser Ala Val Ser His Arg Lys Gln Asn Ser
1               5                   10                  15

Gly Trp Ser Gly Arg Asn Leu Ser Tyr Glu Pro Arg Arg Gln Arg Gly
                20                  25                  30

Gly Gly Glu Ala Tyr Thr
            35
```

(2) INFORMATION FOR SEQ ID NO: 8:

(i) SEQUENCE CHARACTERISTICS:
        (A) LENGTH: 22 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 8:

```
Ser Gly Ser Leu Gln Val Thr Thr Ala Phe Ala Val Leu Arg Gln Leu
1               5                   10                  15

Gly Leu Glu Glu Asn Thr
            20
```

(2) INFORMATION FOR SEQ ID NO: 9:

(i) SEQUENCE CHARACTERISTICS:
        (A) LENGTH: 20 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 9:

```
Lys Lys Glu Pro Gln Glu Ala Leu Phe Ser Val Lys Gln Tyr Phe Tyr
1               5                  10                  15

Thr Val Ala Pro
            20
```

(2) INFORMATION FOR SEQ ID NO: 10:

(i) SEQUENCE CHARACTERISTICS:
        (A) LENGTH: 4 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 10:

```
His Ile Cys Gly
1
```

(2) INFORMATION FOR SEQ ID NO: 11:

(i) SEQUENCE CHARACTERISTICS:
        (A) LENGTH: 60 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 11:

```
Asn Pro Met Asp Val Ser Ser Leu Thr Ile Thr Lys Ser Gly Glu Asp
1               5                  10                  15

Lys Gly Asp Phe Pro Val Ser Thr Ser Asn Lys Val Lys Ile Pro Gly
            20                  25                  30

Trp Thr Phe Ala Ala Ser Phe Gln Val Phe Leu Thr Thr Leu His Tyr
            35                  40                  45

Trp Thr Leu Glu Gly Gly Ala Tyr Arg Lys Arg Phe
            50                  55                  60
```

(2) INFORMATION FOR SEQ ID NO: 12:

(i) SEQUENCE CHARACTERISTICS:
        (A) LENGTH: 17 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 12:

```
Thr Tyr Phe Ile Ala Val Asp Cys Val Pro Arg Cys Arg Asn Tyr Gln
1               5                  10                  15

Ile
```

(2) INFORMATION FOR SEQ ID NO: 13:

```
        (i) SEQUENCE CHARACTERISTICS:
            (A) LENGTH: 19 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO: 13:

Gly Thr Arg Ser Arg Arg Tyr Asp Arg Pro Gly Ser Cys Cys Ala Pro
1               5                   10                  15
Ser Ala Ala (2) INFORMATION FOR SEQ ID NO: 14:

(i) SEQUENCE CHARACTERISTICS:
            (A) LENGTH: 8 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO: 14:

Arg Val Val Thr Gly Arg Phe His
1               5

(2) INFORMATION FOR SEQ ID NO: 15:

(i) SEQUENCE CHARACTERISTICS:
            (A) LENGTH: 17 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO: 15:

His Cys Glu Leu Ser Gly Leu Pro Val Thr Lys Arg Leu Gly Glu Val
1               5                   10                  15
Val (2) INFORMATION FOR SEQ ID NO: 16:

(i) SEQUENCE CHARACTERISTICS:
            (A) LENGTH: 7 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO: 16:

Thr Lys Arg Asn Ser Ser Ser
1               5

(2) INFORMATION FOR SEQ ID NO: 17:

(i) SEQUENCE CHARACTERISTICS:
            (A) LENGTH: 4 amino acids
            (B) TYPE: amino acid
            (C) STRANDEDNESS: single
            (D) TOPOLOGY: Not Relevant (ii) MOLECULE TYPE: peptide (xi) SEQUENCE DESCRIPTION: SEQ ID NO: 17:
```

```
Lys Ser Thr Gln
 1

(2) INFORMATION FOR SEQ ID NO: 18:

(i) SEQUENCE CHARACTERISTICS:
        (A) LENGTH: 4 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 18:

Phe Cys Ile Asn
 1

(2) INFORMATION FOR SEQ ID NO: 19:

(i) SEQUENCE CHARACTERISTICS:
        (A) LENGTH: 40 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 19:

Ile Leu Asn Phe Ser Gly Gly Thr Val Arg Lys Ser Arg His Gln Gln
 1               5                  10                  15

Gln Asn Gly Glu Trp Arg Gly Gly Gln Gly Phe Gln Leu Pro Phe Asp
                20                  25                  30

Phe Leu Leu Gln Thr His Pro Phe
            35                  40

(2) INFORMATION FOR SEQ ID NO: 20:

(i) SEQUENCE CHARACTERISTICS:
        (A) LENGTH: 8 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 20:

Met Arg Leu Val Phe Pro Ser Leu
 1               5

(2) INFORMATION FOR SEQ ID NO: 21:

(i) SEQUENCE CHARACTERISTICS:
        (A) LENGTH: 5 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 21:

Val Lys Ser Asn Met
 1               5

(2) INFORMATION FOR SEQ ID NO: 22:

(i) SEQUENCE CHARACTERISTICS:
        (A) LENGTH: 26 amino acids
        (B) TYPE: amino acid
```

(C) STRANDEDNESS: single
        (D) TOPOLOGY: Not Relevant (ii) MOLECULE TYPE: peptide (xi) SEQUENCE DESCRIPTION: SEQ ID NO: 22:

Ile Ala Phe Gly Asn Ser Ser Ser Gln Ala Leu Thr Leu Ile Thr Val
1               5                   10                  15

Cys Asp Cys His Phe Phe Pro Arg Pro Val
            20                  25

(2) INFORMATION FOR SEQ ID NO: 23:

(i) SEQUENCE CHARACTERISTICS:
        (A) LENGTH: 41 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 23:

Gly Cys Phe Ile Leu Lys Val Leu Thr Ser Gly Ser Lys Phe Ser Lys
1               5                   10                  15

Phe Trp Lys Gln Tyr Ser Tyr Phe Ser Ser Ile Leu Tyr His Val Glu
            20                  25                  30

Val Lys Phe Gly Phe Ser Thr Lys Phe
        35                  40

(2) INFORMATION FOR SEQ ID NO: 24:

(i) SEQUENCE CHARACTERISTICS:
        (A) LENGTH: 31 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 24:

Ile Cys Arg His Thr Cys Thr Leu Thr Cys Pro Gln Met Pro Pro Leu
1               5                   10                  15

Ser Ser Phe Phe Ser Pro Thr Gln Ala Val Phe Phe Tyr Ser Gln
            20                  25                  30

(2) INFORMATION FOR SEQ ID NO: 25:

(i) SEQUENCE CHARACTERISTICS:
        (A) LENGTH: 25 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 25:

Gly Ser Ser Val Xaa Val Ala Asp Gly Pro Ile Ile Leu Gly Ser Tyr
1               5                   10                  15

Ser Leu Tyr Asp Glu Lys Asn Val Leu
            20                  25

(2) INFORMATION FOR SEQ ID NO: 26:

(i) SEQUENCE CHARACTERISTICS:
        (A) LENGTH: 27 amino acids
        (B) TYPE: amino acid (C) STRANDEDNESS: single
                    (D) TOPOLOGY: Not Relevant (ii) MOLECULE TYPE: peptide (xi) SEQUENCE DESCRIPTION: SEQ ID NO: 26:

```
Ile Gly Ala Val Ser Pro Ala Val Arg Pro Ser Ser Thr Ala Asn Glu
1               5                   10                  15

Met Tyr Ala Gln Ser Gly Arg Ile Lys Glu Glu
            20                  25
```

(2) INFORMATION FOR SEQ ID NO: 27:

(i) SEQUENCE CHARACTERISTICS:
            (A) LENGTH: 2765 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION:249..1649

(xi) SEQUENCE DESCRIPTION: SEQ ID NO: 27:

```
TGGGACAGGC AGCTCCGGGG TCCGCGGTTT CACATCGGAA ACAAAACAGC GGCTGGTCTG      60

GAAGGAACCT GAGCTACGAG CCGCGGCGGC AGCGGGGCGG CGGGGAAGCG TATACCTAAT     120

CTGGGAGCCT GCAAGTGACA ACAGCCTTTG CGGTCCTTAG ACAGCTTGGC CTGGAGGAGA     180

ACACATGAAA GAAAGAACCT CAAGAGGCTT TGTTTTCTGT GAAACAGTAT TTCTATACAG     240

TTGCTCCA ATG ACA GAG TTA CCT GCA CCG TTG TCC TAC TTC CAG AAT GCA     290
         Met Thr Glu Leu Pro Ala Pro Leu Ser Tyr Phe Gln Asn Ala
             1               5                   10

CAG ATG TCT GAG GAC AAC CAC CTG AGC AAT ACT GTA CGT AGC CAG AAT     338
Gln Met Ser Glu Asp Asn His Leu Ser Asn Thr Val Arg Ser Gln Asn
 15                  20                  25                  30

GAC AAT AGA GAA CGG CAG GAG CAC AAC GAC AGA CGG AGC CTT GGC CAC     386
Asp Asn Arg Glu Arg Gln Glu His Asn Asp Arg Arg Ser Leu Gly His
                 35                  40                  45

CCT GAG CCA TTA TCT AAT GGA CGA CCC CAG GGT AAC TCC CGG CAG GTG     434
Pro Glu Pro Leu Ser Asn Gly Arg Pro Gln Gly Asn Ser Arg Gln Val
             50                  55                  60

GTG GAG CAA GAT GAG GAA GAA GAT GAG GAG CTG ACA TTG AAA TAT GGC     482
Val Glu Gln Asp Glu Glu Glu Asp Glu Glu Leu Thr Leu Lys Tyr Gly
         65                  70                  75

GCC AAG CAT GTG ATC ATG CTC TTT GTC CCT GTG ACT CTC TGC ATG GTG     530
Ala Lys His Val Ile Met Leu Phe Val Pro Val Thr Leu Cys Met Val
     80                  85                  90

GTG GTC GTG GCT ACC ATT AAG TCA GTC AGC TTT TAT ACC CGG AAG GAT     578
Val Val Val Ala Thr Ile Lys Ser Val Ser Phe Tyr Thr Arg Lys Asp
 95                  100                 105                 110

GGG CAG CTA ATC TAT ACC CCA TTC ACA GAA GAT ACC GAG ACT GTG GGC     626
Gly Gln Leu Ile Tyr Thr Pro Phe Thr Glu Asp Thr Glu Thr Val Gly
                 115                 120                 125

CAG AGA GCC CTG CAC TCA ATT CTG AAT GCT GCC ATC ATG ATC AGT GTC     674
Gln Arg Ala Leu His Ser Ile Leu Asn Ala Ala Ile Met Ile Ser Val
             130                 135                 140

ATT GTT GTC ATG ACT ATC CTC CTG GTG GTT CTG TAT AAA TAC AGG TGC     722
Ile Val Val Met Thr Ile Leu Leu Val Val Leu Tyr Lys Tyr Arg Cys
         145                 150                 155

TAT AAG GTC ATC CAT GCC TGG CTT ATT ATA TCA TCT CTA TTG TTG CTG     770
```

```
                Tyr Lys Val Ile His Ala Trp Leu Ile Ile Ser Ser Leu Leu Leu Leu
                    160                 165                 170

TTC TTT TTT TCA TTC ATT TAC TTG GGG GAA GTG TTT AAA ACC TAT AAC                  818
Phe Phe Phe Ser Phe Ile Tyr Leu Gly Glu Val Phe Lys Thr Tyr Asn
175                 180                 185                 190

GTT GCT GTG GAC TAC ATT ACT GTT GCA CTC CTG ATC TGG AAT TTT GGT                  866
Val Ala Val Asp Tyr Ile Thr Val Ala Leu Leu Ile Trp Asn Phe Gly
                    195                 200                 205

GTG GTG GGA ATG ATT TCC ATT CAC TGG AAA GGT CCA CTT CGA CTC CAG                  914
Val Val Gly Met Ile Ser Ile His Trp Lys Gly Pro Leu Arg Leu Gln
                210                 215                 220

CAG GCA TAT CTC ATT ATG ATT AGT GCC CTC ATG GCC CTG GTG TTT ATC                  962
Gln Ala Tyr Leu Ile Met Ile Ser Ala Leu Met Ala Leu Val Phe Ile
            225                 230                 235

AAG TAC CTC CCT GAA TGG ACT GCG TGG CTC ATC TTG GCT GTG ATT TCA                 1010
Lys Tyr Leu Pro Glu Trp Thr Ala Trp Leu Ile Leu Ala Val Ile Ser
        240                 245                 250

GTA TAT GAT TTA GTG GCT GTT TTG CGT CCG AAA GGT CCA CTT CGT ATG                 1058
Val Tyr Asp Leu Val Ala Val Leu Arg Pro Lys Gly Pro Leu Arg Met
255                 260                 265                 270

CTG GTT GAA ACA GCT CAG GAG AGA AAT GAA ACG CTT TTT CCA GCT CTC                 1106
Leu Val Glu Thr Ala Gln Glu Arg Asn Glu Thr Leu Phe Pro Ala Leu
                    275                 280                 285

ATT TAC TCC TCA ACA ATG GTG TGG TTG GTG AAT ATG GCA GAA GGA GAC                 1154
Ile Tyr Ser Ser Thr Met Val Trp Leu Val Asn Met Ala Glu Gly Asp
                290                 295                 300

CCG GAA GCT CAA AGG AGA GTA TCC AAA AAT TCC AAG CAT AAT GCA GAA                 1202
Pro Glu Ala Gln Arg Arg Val Ser Lys Asn Ser Lys His Asn Ala Glu
            305                 310                 315

AGC ACA GAA AGG GAG TCA CAA GAC ACT GTT GCA GAG AAT GAT GAT GGC                 1250
Ser Thr Glu Arg Glu Ser Gln Asp Thr Val Ala Glu Asn Asp Asp Gly
        320                 325                 330

GGG TTC AGT GAG GAA TGG GAA GCC CAG AGG GAC AGT CAT CTA GGG CCT                 1298
Gly Phe Ser Glu Glu Trp Glu Ala Gln Arg Asp Ser His Leu Gly Pro
335                 340                 345                 350

CAT CGC TCT ACA CCT GAG TCA CGA GCT GCT GTC CAG GAA CTT TCC AGC                 1346
His Arg Ser Thr Pro Glu Ser Arg Ala Ala Val Gln Glu Leu Ser Ser
                    355                 360                 365

AGT ATC CTC GCT GGT GAA GAC CCA GAG GAA AGG GGA GTA AAA CTT GGA                 1394
Ser Ile Leu Ala Gly Glu Asp Pro Glu Glu Arg Gly Val Lys Leu Gly
                370                 375                 380

TTG GGA GAT TTC ATT TTC TAC AGT GTT CTG GTT GGT AAA GCC TCA GCA                 1442
Leu Gly Asp Phe Ile Phe Tyr Ser Val Leu Val Gly Lys Ala Ser Ala
            385                 390                 395

ACA GCC AGT GGA GAC TGG AAC ACA ACC ATA GCC TGT TTC GTA GCC ATA                 1490
Thr Ala Ser Gly Asp Trp Asn Thr Thr Ile Ala Cys Phe Val Ala Ile
        400                 405                 410

TTA ATT GGT TTG TGC CTT ACA TTA TTA CTC CTT GCC ATT TTC AAG AAA                 1538
Leu Ile Gly Leu Cys Leu Thr Leu Leu Leu Ala Ile Phe Lys Lys
415                 420                 425                 430

GCA TTG CCA GCT CTT CCA ATC TCC ATC ACC TTT GGG CTT GTT TTC TAC                 1586
Ala Leu Pro Ala Leu Pro Ile Ser Ile Thr Phe Gly Leu Val Phe Tyr
                    435                 440                 445

TTT GCC ACA GAT TAT CTT GTA CAG CCT TTT ATG GAC CAA TTA GCA TTC                 1634
Phe Ala Thr Asp Tyr Leu Val Gln Pro Phe Met Asp Gln Leu Ala Phe
                450                 455                 460

CAT CAA TTT TAT ATC TAGCATATTT GCGGTTAGAA TCCCATGGAT GTTTCTTCTT                 1689
His Gln Phe Tyr Ile
            465
```

-continued

```
TGACTATAAC CAAATCTGGG GAGGACAAAG GTGATTTTCC TGTGTCCACA TCTAACAAAG      1749

TCAAGATTCC CGGCTGGACT TTTGCAGCTT CCTTCCAAGT CTTCCTGACC ACCTTGCACT      1809

ATTGGACTTT GGAAGGAGGT GCCTATAGAA AACGATTTTG AACATACTTC ATCGCAGTGG      1869

ACTGTGTCCC TCGGTGCAGA AACTACCAGA TTTGAGGGAC GAGGTCAAGG AGATATGATA      1929

GGCCCGGAAG TTGCTGTGCC CCATCAGCAG CTTGACGCGT GGTCACAGGA CGATTTCACT      1989

GACACTGCGA ACTCTCAGGA CTACCGGTTA CCAAGAGGTT AGGTGAAGTG GTTTAAACCA      2049

AACGGAACTC TTCATCTTAA ACTACACGTT GAAAATCAAC CCAATAATTC TGTATTAACT      2109

GAATTCTGAA CTTTTCAGGA GGTACTGTGA GGAAGAGCAG GCACCAGCAG CAGAATGGGG      2169

AATGGAGAGG TGGGCAGGGG TTCCAGCTTC CCTTTGATTT TTTGCTGCAG ACTCATCCTT      2229

TTTAAATGAG ACTTGTTTTC CCCTCTCTTT GAGTCAAGTC AAATATGTAG ATTGCCTTTG      2289

GCAATTCTTC TTCTCAAGCA CTGACACTCA TTACCGTCTG TGATTGCCAT TTCTTCCCAA      2349

GGCCAGTCTG AACCTGAGGT TGCTTTATCC TAAAAGTTTT AACCTCAGGT TCCAAATTCA      2409

GTAAATTTTG GAAACAGTAC AGCTATTTCT CATCAATTCT CTATCATGTT GAAGTCAAAT      2469

TTGGATTTTC CACCAAATTC TGAATTTGTA GACATACTTG TACGCTCACT TGCCCCCAGA      2529

TGCCTCCTCT GTCCTCATTC TTCTCTCCCA CACAAGCAGT CTTTTTCTAC AGCCAGTAAG      2589

GCAGCTCTGT CRTGGTAGCA GATGGTCCCA TTATTCTAGG GTCTTACTCT TTGTATGATG      2649

AAAAGAATGT GTTATGAATC GGTGCTGTCA GCCCTGCTGT CAGACCTTCT TCCACAGCAA      2709

ATGAGATGTA TGCCCAAAGC GGTAGAATTA AGAAGAGTA AATGGCTGT TGAAGC           2765
```

(2) INFORMATION FOR SEQ ID NO: 28:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO: 28:

```
Met Thr Glu Leu Pro Ala Pro Leu Ser Tyr Phe Gln Asn Ala Gln Met
 1               5                  10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
```

```
                    165                 170                 175
Phe Ser Phe Ile Tyr Leu Gly Glu Val Phe Lys Thr Tyr Asn Val Ala
                180                 185                 190
Val Asp Tyr Ile Thr Val Ala Leu Leu Ile Trp Asn Phe Gly Val Val
            195                 200                 205
Gly Met Ile Ser Ile His Trp Lys Gly Pro Leu Arg Leu Gln Gln Ala
        210                 215                 220
Tyr Leu Ile Met Ile Ser Ala Leu Met Ala Leu Val Phe Ile Lys Tyr
225                 230                 235                 240
Leu Pro Glu Trp Thr Ala Trp Leu Ile Leu Ala Val Ile Ser Val Tyr
                245                 250                 255
Asp Leu Val Ala Val Leu Arg Pro Lys Gly Pro Leu Arg Met Leu Val
            260                 265                 270
Glu Thr Ala Gln Glu Arg Asn Glu Thr Leu Phe Pro Ala Leu Ile Tyr
        275                 280                 285
Ser Ser Thr Met Val Trp Leu Val Asn Met Ala Glu Gly Asp Pro Glu
    290                 295                 300
Ala Gln Arg Arg Val Ser Lys Asn Ser Lys His Asn Ala Glu Ser Thr
305                 310                 315                 320
Glu Arg Glu Ser Gln Asp Thr Val Ala Glu Asn Asp Asp Gly Gly Phe
                325                 330                 335
Ser Glu Glu Trp Glu Ala Gln Arg Asp Ser His Leu Gly Pro His Arg
            340                 345                 350
Ser Thr Pro Glu Ser Arg Ala Ala Val Gln Glu Leu Ser Ser Ser Ile
        355                 360                 365
Leu Ala Gly Glu Asp Pro Glu Glu Arg Gly Val Lys Leu Gly Leu Gly
370                 375                 380
Asp Phe Ile Phe Tyr Ser Val Leu Val Gly Lys Ala Ser Ala Thr Ala
385                 390                 395                 400
Ser Gly Asp Trp Asn Thr Thr Ile Ala Cys Phe Val Ala Ile Leu Ile
                405                 410                 415
Gly Leu Cys Leu Thr Leu Leu Leu Leu Ala Ile Phe Lys Lys Ala Leu
            420                 425                 430
Pro Ala Leu Pro Ile Ser Ile Thr Phe Gly Leu Val Phe Tyr Phe Ala
        435                 440                 445
Thr Asp Tyr Leu Val Gln Pro Phe Met Asp Gln Leu Ala Phe His Gln
450                 455                 460
Phe Tyr Ile
465

(2) INFORMATION FOR SEQ ID NO: 29:

(i) SEQUENCE CHARACTERISTICS:
        (A) LENGTH: 2765 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:249..1649

(xi) SEQUENCE DESCRIPTION: SEQ ID NO: 29:

TGGGACAGGC AGCTCCGGGG TCCGCGGTTT CACATCGGAA ACAAACAGC GGCTGGTCTG      60

GAAGGAACCT GAGCTACGAG CCGCGGCGGC AGCGGGGCGG CGGGGAAGCG TATACCTAAT    120
```

```
CTGGGAGCCT GCAAGTGACA ACAGCCTTTG CGGTCCTTAG ACAGCTTGGC CTGGAGGAGA      180

ACACATGAAA GAAAGAACCT CAAGAGGCTT TGTTTTCTGT GAAACAGTAT TTCTATACAG      240

TTGCTCCA ATG ACA GAG TTA CCT GCA CCG TTG TCC TAC TTC CAG AAT GCA      290
         Met Thr Glu Leu Pro Ala Pro Leu Ser Tyr Phe Gln Asn Ala
          1               5                          10

CAG ATG TCT GAG GAC AAC CAC CTG AGC AAT ACT GTA CGT AGC CAG AAT       338
Gln Met Ser Glu Asp Asn His Leu Ser Asn Thr Val Arg Ser Gln Asn
 15              20                  25                      30

GAC AAT AGA GAA CGG CAG GAG CAC AAC GAC AGA CGG AGC CTT GGC CAC       386
Asp Asn Arg Glu Arg Gln Glu His Asn Asp Arg Arg Ser Leu Gly His
             35                  40                      45

CCT GAG CCA TTA TCT AAT GGA CGA CCC CAG GGT AAC TCC CGG CAG GTG       434
Pro Glu Pro Leu Ser Asn Gly Arg Pro Gln Gly Asn Ser Arg Gln Val
             50                  55                      60

GTG GAG CAA GAT GAG GAA GAA GAT GAG GAG CTG ACA TTG AAA TAT GGC       482
Val Glu Gln Asp Glu Glu Glu Asp Glu Glu Leu Thr Leu Lys Tyr Gly
             65                  70                      75

GCC AAG CAT GTG ATC ATG CTC TTT GTC CCT GTG ACT CTC TGC ATG GTG       530
Ala Lys His Val Ile Met Leu Phe Val Pro Val Thr Leu Cys Met Val
         80                  85                      90

GTG GTC GTG GCT ACC ATT AAG TCA GTC AGC TTT TAT ACC CGG AAG GAT       578
Val Val Val Ala Thr Ile Lys Ser Val Ser Phe Tyr Thr Arg Lys Asp
 95                 100                 105                     110

GGG CAG CTA ATC TAT ACC CCA TTC ACA GAA GAT ACC GAG ACT GTG GGC       626
Gly Gln Leu Ile Tyr Thr Pro Phe Thr Glu Asp Thr Glu Thr Val Gly
                115                 120                     125

CAG AGA GCC CTG CAC TCA ATT CTG AAT GCT GCC ATC ATG ATC AGT GTC       674
Gln Arg Ala Leu His Ser Ile Leu Asn Ala Ala Ile Met Ile Ser Val
                130                 135                     140

ATT GTT GTC ATG ACT ATC CTC CTG GTG GTT CTG TAT AAA TAC AGG TGC       722
Ile Val Val Met Thr Ile Leu Leu Val Val Leu Tyr Lys Tyr Arg Cys
                145                 150                     155

TAT AAG GTC ATC CAT GCC TGG CTT ATT ATA TCA TCT CTA TTG TTG CTG       770
Tyr Lys Val Ile His Ala Trp Leu Ile Ile Ser Ser Leu Leu Leu Leu
        160                 165                     170

TTC TTT TTT TCA TTC ATT TAC TTG GGG GAA GTG TTT AAA ACC TAT AAC       818
Phe Phe Phe Ser Phe Ile Tyr Leu Gly Glu Val Phe Lys Thr Tyr Asn
175                 180                     185                 190

GTT GCT GTG GAC TAC ATT ACT GTT GCA CTC CTG ATC TGG AAT TTT GGT       866
Val Ala Val Asp Tyr Ile Thr Val Ala Leu Leu Ile Trp Asn Phe Gly
                195                 200                     205

GTG GTG GGA ATG ATT TCC ATT CAC TGG AAA GGT CCA CTT CGA CTC CAG       914
Val Val Gly Met Ile Ser Ile His Trp Lys Gly Pro Leu Arg Leu Gln
                210                 215                     220

CAG GCA TAT CTC ATT ATG ATT AGT GCC CTC ATG GCC CTG GTG TTT ATC       962
Gln Ala Tyr Leu Ile Met Ile Ser Ala Leu Met Ala Leu Val Phe Ile
                225                 230                     235

AAG TAC CTC CCT GAA TGG ACT GCG TGG CTC ATC TTG GCT GTG ATT TCA      1010
Lys Tyr Leu Pro Glu Trp Thr Ala Trp Leu Ile Leu Ala Val Ile Ser
        240                 245                     250

GTA TAT GAT TTA GTG GCT GTT TTG TGT CTG AAA GGT CCA CTT CGT ATG      1058
Val Tyr Asp Leu Val Ala Val Leu Cys Leu Lys Gly Pro Leu Arg Met
255                 260                     265                 270

CTG GTT GAA ACA GCT CAG GAG AGA AAT GAA ACG CTT TTT CCA GCT CTC      1106
Leu Val Glu Thr Ala Gln Glu Arg Asn Glu Thr Leu Phe Pro Ala Leu
                275                 280                     285

ATT TAC TCC TCA ACA ATG GTG TGG TTG GTG AAT ATG GCA GAA GGA GAC      1154
Ile Tyr Ser Ser Thr Met Val Trp Leu Val Asn Met Ala Glu Gly Asp
```

```
                    290                 295                 300
CCG GAA GCT CAA AGG AGA GTA TCC AAA AAT TCC AAG CAT AAT GCA GAA        1202
Pro Glu Ala Gln Arg Arg Val Ser Lys Asn Ser Lys His Asn Ala Glu
            305                 310                 315

AGC ACA GAA AGG GAG TCA CAA GAC ACT GTT GCA GAG AAT GAT GAT GGC        1250
Ser Thr Glu Arg Glu Ser Gln Asp Thr Val Ala Glu Asn Asp Asp Gly
        320                 325                 330

GGG TTC AGT GAG GAA TGG GAA GCC CAG AGG GAC AGT CAT CTA GGG CCT        1298
Gly Phe Ser Glu Glu Trp Glu Ala Gln Arg Asp Ser His Leu Gly Pro
335                 340                 345                 350

CAT CGC TCT ACA CCT GAG TCA CGA GCT GCT GTC CAG GAA CTT TCC AGC        1346
His Arg Ser Thr Pro Glu Ser Arg Ala Ala Val Gln Glu Leu Ser Ser
                355                 360                 365

AGT ATC CTC GCT GGT GAA GAC CCA GAG GAA AGG GGA GTA AAA CTT GGA        1394
Ser Ile Leu Ala Gly Glu Asp Pro Glu Glu Arg Gly Val Lys Leu Gly
            370                 375                 380

TTG GGA GAT TTC ATT TTC TAC AGT GTT CTG GTT GGT AAA GCC TCA GCA        1442
Leu Gly Asp Phe Ile Phe Tyr Ser Val Leu Val Gly Lys Ala Ser Ala
        385                 390                 395

ACA GCC AGT GGA GAC TGG AAC ACA ACC ATA GCC TGT TTC GTA GCC ATA        1490
Thr Ala Ser Gly Asp Trp Asn Thr Thr Ile Ala Cys Phe Val Ala Ile
    400                 405                 410

TTA ATT GGT TTG TGC CTT ACA TTA TTA CTC CTT GCC ATT TTC AAG AAA        1538
Leu Ile Gly Leu Cys Leu Thr Leu Leu Leu Leu Ala Ile Phe Lys Lys
415                 420                 425                 430

GCA TTG CCA GCT CTT CCA ATC TCC ATC ACC TTT GGG CTT GTT TTC TAC        1586
Ala Leu Pro Ala Leu Pro Ile Ser Ile Thr Phe Gly Leu Val Phe Tyr
                435                 440                 445

TTT GCC ACA GAT TAT CTT GTA CAG CCT TTT ATG GAC CAA TTA GCA TTC        1634
Phe Ala Thr Asp Tyr Leu Val Gln Pro Phe Met Asp Gln Leu Ala Phe
            450                 455                 460

CAT CAA TTT TAT ATC TAGCATATTT GCGGTTAGAA TCCCATGGAT GTTTCTTCTT        1689
His Gln Phe Tyr Ile
            465

TGACTATAAC CAAATCTGGG GAGGACAAAG GTGATTTTCC TGTGTCCACA TCTAACAAAG     1749

TCAAGATTCC CGGCTGGACT TTTGCAGCTT CCTTCCAAGT CTTCCTGACC ACCTTGCACT     1809

ATTGGACTTT GGAAGGAGGT GCCTATAGAA AACGATTTTG AACATACTTC ATCGCAGTGG     1869

ACTGTGTCCC TCGGTGCAGA AACTACCAGA TTTGAGGGAC GAGGTCAAGG AGATATGATA     1929

GGCCCGGAAG TTGCTGTGCC CCATCAGCAG CTTGACGCGT GGTCACAGGA CGATTTCACT     1989

GACACTGCGA ACTCTCAGGA CTACCGGTTA CCAAGAGGTT AGGTGAAGTG GTTTAAACCA     2049

AACGGAACTC TTCATCTTAA ACTACACGTT GAAAATCAAC CCAATAATTC TGTATTAACT     2109

GAATTCTGAA CTTTTCAGGA GGTACTGTGA GGAAGAGCAG GCACCAGCAG CAGAATGGGG     2169

AATGGAGAGG TGGGCAGGGG TTCCAGCTTC CCTTTGATTT TTTGCTGCAG ACTCATCCTT     2229

TTTAAATGAG ACTTGTTTTC CCCTCTCTTT GAGTCAAGTC AAATATGTAG ATTGCCTTTG     2289

GCAATTCTTC TTCTCAAGCA CTGACACTCA TTACCGTCTG TGATTGCCAT TCTTCCCAA      2349

GGCCAGTCTG AACCTGAGGT TGCTTTATCC TAAAAGTTTT AACCTCAGGT TCCAAATTCA     2409

GTAAATTTTG GAAACAGTAC AGCTATTTCT CATCAATTCT CTATCATGTT GAAGTCAAAT     2469

TTGGATTTTC CACCAAATTC TGAATTTGTA GACATACTTG TACGCTCACT TGCCCCCAGA     2529

TGCCTCCTCT GTCCTCATTC TTCTCTCCCA CACAAGCAGT CTTTTTCTAC AGCCAGTAAG     2589

GCAGCTCTGT CRTGGTAGCA GATGGTCCCA TTATTCTAGG GTCTTACTCT TTGTATGATG     2649

AAAAGAATGT GTTATGAATC GGTGCTGTCA GCCCTGCTGT CAGACCTTCT TCCACAGCAA     2709
```

ATGAGATGTA TGCCCAAAGC GGTAGAATTA AAGAAGAGTA AAATGGCTGT TGAAGC    2765

(2) INFORMATION FOR SEQ ID NO: 30:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO: 30:

```
Met Thr Glu Leu Pro Ala Pro Leu Ser Tyr Phe Gln Asn Ala Gln Met
 1               5                  10                  15

Ser Glu Asp Asn His Leu Ser Asn Thr Val Arg Ser Gln Asn Asp Asn
             20                  25                  30

Arg Glu Arg Gln Glu His Asn Asp Arg Arg Ser Leu Gly His Pro Glu
         35                  40                  45

Pro Leu Ser Asn Gly Arg Pro Gln Gly Asn Ser Arg Gln Val Val Glu
     50                  55                  60

Gln Asp Glu Glu Asp Glu Glu Leu Thr Leu Lys Tyr Gly Ala Lys
 65                  70                  75                  80

His Val Ile Met Leu Phe Val Pro Val Thr Leu Cys Met Val Val Val
                 85                  90                  95

Val Ala Thr Ile Lys Ser Val Ser Phe Tyr Thr Arg Lys Asp Gly Gln
                100                 105                 110

Leu Ile Tyr Thr Pro Phe Thr Glu Asp Thr Glu Thr Val Gly Gln Arg
            115                 120                 125

Ala Leu His Ser Ile Leu Asn Ala Ala Ile Met Ile Ser Val Ile Val
        130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
                180                 185                 190

Val Asp Tyr Ile Thr Val Ala Leu Leu Ile Trp Asn Phe Gly Val Val
            195                 200                 205

Gly Met Ile Ser Ile His Trp Lys Gly Pro Leu Arg Leu Gln Gln Ala
        210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Leu Lys Gly Pro Leu Arg Met Leu Val
                260                 265                 270

Glu Thr Ala Gln Glu Arg Asn Glu Thr Leu Phe Pro Ala Leu Ile Tyr
            275                 280                 285

Ser Ser Thr Met Val Trp Leu Val Asn Met Ala Glu Gly Asp Pro Glu
        290                 295                 300

Ala Gln Arg Arg Val Ser Lys Asn Ser Lys His Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
```

-continued

```
                   340                 345                 350
Ser Thr Pro Glu Ser Arg Ala Ala Val Gln Glu Leu Ser Ser Ser Ile
        355                 360                 365

Leu Ala Gly Glu Asp Pro Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Ala Ile Phe Lys Lys Ala Leu
                420                 425                 430

Pro Ala Leu Pro Ile Ser Ile Thr Phe Gly Leu Val Phe Tyr Phe Ala
            435                 440                 445

Thr Asp Tyr Leu Val Gln Pro Phe Met Asp Gln Leu Ala Phe His Gln
        450                 455                 460

Phe Tyr Ile
465

(2) INFORMATION FOR SEQ ID NO: 31:

(i) SEQUENCE CHARACTERISTICS:
        (A) LENGTH: 2765 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:249..1649

(xi) SEQUENCE DESCRIPTION: SEQ ID NO: 31:

TGGGACAGGC AGCTCCGGGG TCCGCGGTTT CACATCGGAA ACAAAACAGC GGCTGGTCTG      60

GAAGGAACCT GAGCTACGAG CCGCGGCGGC AGCGGGGCGG CGGGGAAGCG TATACCTAAT    120

CTGGGAGCCT GCAAGTGACA ACAGCCTTTG CGGTCCTTAG ACAGCTTGGC CTGGAGGAGA    180

ACACATGAAA GAAAGAACCT CAAGAGGCTT TGTTTTCTGT GAAACAGTAT TTCTATACAG    240

TTGCTCCA ATG ACA GAG TTA CCT GCA CCG TTG TCC TAC TTC CAG AAT GCA    290
         Met Thr Glu Leu Pro Ala Pro Leu Ser Tyr Phe Gln Asn Ala
             1               5                  10

CAG ATG TCT GAG GAC AAC CAC CTG AGC AAT ACT GTA CGT AGC CAG AAT    338
Gln Met Ser Glu Asp Asn His Leu Ser Asn Thr Val Arg Ser Gln Asn
 15              20                  25                  30

GAC AAT AGA GAA CGG CAG GAG CAC AAC GAC AGA CGG AGC CTT GGC CAC    386
Asp Asn Arg Glu Arg Gln Glu His Asn Asp Arg Arg Ser Leu Gly His
                35                  40                  45

CCT GAG CCA TTA TCT AAT GGA CGA CCC CAG GGT AAC TCC CGG CAG GTG    434
Pro Glu Pro Leu Ser Asn Gly Arg Pro Gln Gly Asn Ser Arg Gln Val
            50                  55                  60

GTG GAG CAA GAT GAG GAA GAA GAT GAG GAG CTG ACA TTG AAA TAT GGC    482
Val Glu Gln Asp Glu Glu Glu Asp Glu Glu Leu Thr Leu Lys Tyr Gly
        65                  70                  75

GCC AAG CAT GTG ATC ATG CTC TTT GTC CCT GTG ACT CTC TGC ATG GTG    530
Ala Lys His Val Ile Met Leu Phe Val Pro Val Thr Leu Cys Met Val
    80                  85                  90

GTG GTC GTG GCT ACC ATT AAG TCA GTC AGC TTT TAT ACC CGG AAG GAT    578
Val Val Val Ala Thr Ile Lys Ser Val Ser Phe Tyr Thr Arg Lys Asp
 95                 100                 105                 110
```

-continued

| | |
|---|---|
| GGG CAG CTA ATC TAT ACC CCA TTC ACA GAA GAT ACC GAG ACT GTG GGC<br>Gly Gln Leu Ile Tyr Thr Pro Phe Thr Glu Asp Thr Glu Thr Val Gly<br>              115                    120                  125 | 626 |
| CAG AGA GCC CTG CAC TCA ATT CTG AAT GCT GCC ATC ATG ATC AGT GTC<br>Gln Arg Ala Leu His Ser Ile Leu Asn Ala Ala Ile Met Ile Ser Val<br>        130                    135                    140 | 674 |
| ATT GTT GTC ATG ACT ATC CTC CTG GTG GTT CTG TAT AAA TAC AGG TGC<br>Ile Val Val Met Thr Ile Leu Leu Val Val Leu Tyr Lys Tyr Arg Cys<br>            145                    150                    155 | 722 |
| TAT AAG GTC ATC CAT GCC TGG CTT ATT ATA TCA TCT CTA TTG TTG CTG<br>Tyr Lys Val Ile His Ala Trp Leu Ile Ile Ser Ser Leu Leu Leu Leu<br>        160                    165                    170 | 770 |
| TTC TTT TTT TCA TTC ATT TAC TTG GGG GAA GTG TTT AAA ACC TAT AAC<br>Phe Phe Phe Ser Phe Ile Tyr Leu Gly Glu Val Phe Lys Thr Tyr Asn<br>175                    180                    185                    190 | 818 |
| GTT GCT GTG GAC TAC ATT ACT GTT GCA CTC CTG ATC TGG AAT TTT GGT<br>Val Ala Val Asp Tyr Ile Thr Val Ala Leu Leu Ile Trp Asn Phe Gly<br>                  195                    200                    205 | 866 |
| GTG GTG GGA ATG ATT TCC ATT CAC TGG AAA GGT CCA CTT CGA CTC CAG<br>Val Val Gly Met Ile Ser Ile His Trp Lys Gly Pro Leu Arg Leu Gln<br>            210                    215                    220 | 914 |
| CAG GCA TAT CTC ATT ATG ATT AGT GCC CTC ATG GCC CTG GTG TTT ATC<br>Gln Ala Tyr Leu Ile Met Ile Ser Ala Leu Met Ala Leu Val Phe Ile<br>                225                    230                    235 | 962 |
| AAG TAC CTC CCT GAA TGG ACT GCG TGG CTC ATC TTG GCT GTG ATT TCA<br>Lys Tyr Leu Pro Glu Trp Thr Ala Trp Leu Ile Leu Ala Val Ile Ser<br>        240                    245                    250 | 1010 |
| GTA TAT GAT TTA GTG GCT GTT TTG TGT CCG AAA GGT CCA CTT CAT ATG<br>Val Tyr Asp Leu Val Ala Val Leu Cys Pro Lys Gly Pro Leu His Met<br>255                    260                    265                    270 | 1058 |
| CTG GTT GAA ACA GCT CAG GAG AGA AAT GAA ACG CTT TTT CCA GCT CTC<br>Leu Val Glu Thr Ala Gln Glu Arg Asn Glu Thr Leu Phe Pro Ala Leu<br>                275                    280                    285 | 1106 |
| ATT TAC TCC TCA ACA ATG GTG TGG TTG GTG AAT ATG GCA GAA GGA GAC<br>Ile Tyr Ser Ser Thr Met Val Trp Leu Val Asn Met Ala Glu Gly Asp<br>            290                    295                    300 | 1154 |
| CCG GAA GCT CAA AGG AGA GTA TCC AAA AAT TCC AAG CAT AAT GCA GAA<br>Pro Glu Ala Gln Arg Arg Val Ser Lys Asn Ser Lys His Asn Ala Glu<br>        305                    310                    315 | 1202 |
| AGC ACA GAA AGG GAG TCA CAA GAC ACT GTT GCA GAG AAT GAT GAT GGC<br>Ser Thr Glu Arg Glu Ser Gln Asp Thr Val Ala Glu Asn Asp Asp Gly<br>        320                    325                    330 | 1250 |
| GGG TTC AGT GAG GAA TGG GAA GCC CAG AGG GAC AGT CAT CTA GGG CCT<br>Gly Phe Ser Glu Glu Trp Glu Ala Gln Arg Asp Ser His Leu Gly Pro<br>335                    340                    345                    350 | 1298 |
| CAT CGC TCT ACA CCT GAG TCA CGA GCT GCT GTC CAG GAA CTT TCC AGC<br>His Arg Ser Thr Pro Glu Ser Arg Ala Ala Val Gln Glu Leu Ser Ser<br>                355                    360                    365 | 1346 |
| AGT ATC CTC GCT GGT GAA GAC CCA GAG GAA AGG GGA GTA AAA CTT GGA<br>Ser Ile Leu Ala Gly Glu Asp Pro Glu Glu Arg Gly Val Lys Leu Gly<br>            370                    375                    380 | 1394 |
| TTG GGA GAT TTC ATT TTC TAC AGT GTT CTG GTT GGT AAA GCC TCA GCA<br>Leu Gly Asp Phe Ile Phe Tyr Ser Val Leu Val Gly Lys Ala Ser Ala<br>        385                    390                    395 | 1442 |
| ACA GCC AGT GGA GAC TGG AAC ACA ACC ATA GCC TGT TTC GTA GCC ATA<br>Thr Ala Ser Gly Asp Trp Asn Thr Thr Ile Ala Cys Phe Val Ala Ile<br>        400                    405                    410 | 1490 |
| TTA ATT GGT TTG TGC CTT ACA TTA TTA CTC CTT GCC ATT TTC AAG AAA<br>Leu Ile Gly Leu Cys Leu Thr Leu Leu Leu Ala Ile Phe Lys Lys<br>415                    420                    425                    430 | 1538 |

```
GCA TTG CCA GCT CTT CCA ATC TCC ATC ACC TTT GGG CTT GTT TTC TAC     1586
Ala Leu Pro Ala Leu Pro Ile Ser Ile Thr Phe Gly Leu Val Phe Tyr
            435                 440                 445

TTT GCC ACA GAT TAT CTT GTA CAG CCT TTT ATG GAC CAA TTA GCA TTC     1634
Phe Ala Thr Asp Tyr Leu Val Gln Pro Phe Met Asp Gln Leu Ala Phe
            450                 455                 460

CAT CAA TTT TAT ATC TAGCATATTT GCGGTTAGAA TCCCATGGAT GTTTCTTCTT     1689
His Gln Phe Tyr Ile
            465

TGACTATAAC CAAATCTGGG GAGGACAAAG GTGATTTTCC TGTGTCCACA TCTAACAAAG    1749

TCAAGATTCC CGGCTGGACT TTTGCAGCTT CCTTCCAAGT CTTCCTGACC ACCTTGCACT    1809

ATTGGACTTT GGAAGGAGGT GCCTATAGAA AACGATTTTG AACATACTTC ATCGCAGTGG    1869

ACTGTGTCCC TCGGTGCAGA AACTACCAGA TTTGAGGGAC GAGGTCAAGG AGATATGATA    1929

GGCCCGGAAG TTGCTGTGCC CCATCAGCAG CTTGACGCGT GGTCACAGGA CGATTTCACT    1989

GACACTGCGA ACTCTCAGGA CTACCGGTTA CCAAGAGGTT AGGTGAAGTG GTTTAAACCA    2049

AACGGAACTC TTCATCTTAA ACTACACGTT GAAAATCAAC CCAATAATTC TGTATTAACT    2109

GAATTCTGAA CTTTTCAGGA GGTACTGTGA GGAAGAGCAG GCACCAGCAG CAGAATGGGG    2169

AATGGAGAGG TGGGCAGGGG TTCCAGCTTC CCTTTGATTT TTTGCTGCAG ACTCATCCTT    2229

TTTAAATGAG ACTTGTTTTC CCCTCTCTTT GAGTCAAGTC AAATATGTAG ATTGCCTTTG    2289

GCAATTCTTC TTCTCAAGCA CTGACACTCA TTACCGTCTG TGATTGCCAT TCTTCCCAA     2349

GGCCAGTCTG AACCTGAGGT TGCTTTATCC TAAAAGTTTT AACCTCAGGT TCCAAATTCA    2409

GTAAATTTTG GAAACAGTAC AGCTATTTCT CATCAATTCT CTATCATGTT GAAGTCAAAT    2469

TTGGATTTTC CACCAAATTC TGAATTTGTA GACATACTTG TACGCTCACT TGCCCCCAGA    2529

TGCCTCCTCT GTCCTCATTC TTCTCTCCCA CACAAGCAGT CTTTTTCTAC AGCCAGTAAG    2589

GCAGCTCTGT CRTGGTAGCA GATGGTCCCA TTATTCTAGG GTCTTACTCT TTGTATGATG    2649

AAAAGAATGT GTTATGAATC GGTGCTGTCA GCCCTGCTGT CAGACCTTCT TCCACAGCAA    2709

ATGAGATGTA TGCCCAAAGC GGTAGAATTA AAGAAGAGTA AATGGCTGT TGAAGC         2765

(2) INFORMATION FOR SEQ ID NO: 32:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO: 32:

Met Thr Glu Leu Pro Ala Pro Leu Ser Tyr Phe Gln Asn Ala Gln Met
  1               5                  10                  15

Ser Glu Asp Asn His Leu Ser Asn Thr Val Arg Ser Gln Asn Asp Asn
                 20                  25                  30

Arg Glu Arg Gln Glu His Asn Asp Arg Arg Ser Leu Gly His Pro Glu
             35                  40                  45

Pro Leu Ser Asn Gly Arg Pro Gln Gly Asn Ser Arg Gln Val Val Glu
         50                  55                  60

Gln Asp Glu Glu Glu Asp Glu Glu Leu Thr Leu Lys Tyr Gly Ala Lys
 65                  70                  75                  80

His Val Ile Met Leu Phe Val Pro Val Thr Leu Cys Met Val Val Val
                 85                  90                  95
```

-continued

```
Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu His Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
    290                 295                 300

Ala Gln Arg Arg Val Ser Lys Asn Ser Lys His Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
        355                 360                 365

Leu Ala Gly Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Ala Ile Phe Lys Lys Ala Leu
            420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465
```